United States Patent
Cottrell et al.

(10) Patent No.: US 7,906,550 B2
(45) Date of Patent: *Mar. 15, 2011

(54) INHIBITORS OF SERINE PROTEASES, PARTICULARLY HCV NS3-NS4A PROTEASE

(75) Inventors: Kevin M. Cottrell, Cambridge, MA (US); John Maxwell, Quincy, MA (US); Robert B. Perni, Marlborough, MA (US); Janos Pitlik, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/026,705

(22) Filed: Feb. 6, 2008

(65) Prior Publication Data

US 2008/0125376 A1    May 29, 2008

Related U.S. Application Data

(62) Division of application No. 10/821,663, filed on Apr. 9, 2004, now Pat. No. 7,365,092.

(60) Provisional application No. 60/510,317, filed on Oct. 10, 2003.

(51) Int. Cl.
*A61K 31/4025* (2006.01)
*C07D 207/30* (2006.01)

(52) U.S. Cl. ......... 514/423; 548/413; 548/517; 548/518; 514/408; 514/422

(58) Field of Classification Search .................. 548/413, 548/517, 518; 514/408, 422, 423
See application file for complete search history.

(56) References Cited

U.S. PATENT DOCUMENTS

| 7,241,796 B2 * | 7/2007 | Farmer et al. ........... 514/411 |
| 7,273,885 B2 * | 9/2007 | Pitlik et al. ............. 514/414 |
| 7,365,092 B2 * | 4/2008 | Cottrell et al. .......... 514/422 |

* cited by examiner

*Primary Examiner* — Golam M Shameem
(74) *Attorney, Agent, or Firm* — Susan C. Kelly

(57) ABSTRACT

The present invention relates to compounds of formula I:

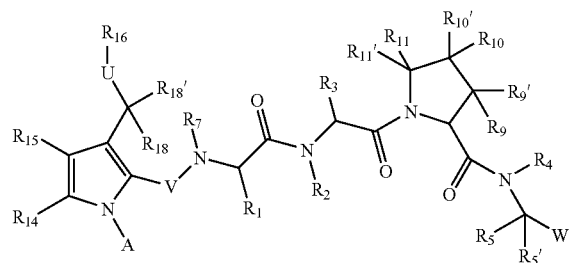

or pharmaceutically acceptable salts thereof that inhibit serine protease activity, particularly the activity of hepatitis C virus NS3-NS4A protease. As such, they act by interfering with the life cycle of the hepatitis C virus and are useful as antiviral agents. The invention further relates to pharmaceutically acceptable compositions comprising said compounds either for ex vivo use or for administration to a patient suffering from HCV infection and to processes for preparing the compounds. The invention also relates to methods of treating an HCV infection in a patient by administering a pharmaceutical composition comprising a compound of this invention.

4 Claims, No Drawings

INHIBITORS OF SERINE PROTEASES, PARTICULARLY HCV NS3-NS4A PROTEASE

CROSS REFERENCE TO RELATED APPLICATIONS

This application is a divisional application of U.S. Ser. No. 10/821,663, filed Apr. 9, 2004, now U.S. Pat. No. 7,365,092 entitled "Inhibitors of Serine Proteases, Particularly HCV NS3-NS4A Protease", which claims the benefit of U.S. Provisional Application No. 60/510,317, filed Oct. 10, 2003, entitled "Inhibitors of Serine Proteases, Particularly HCV NS3-NS4A Protease", the entire contents of these applications are hereby incorporated by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to pharmaceutical compositions comprising these compounds either for ex vivo use or for administration to a patient suffering from HCV infection. The invention also relates to processes for preparing the compounds and methods of treating an HCV infection in a patient by administering a pharmaceutical composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States, Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man, indicating that interrupting this stage of the viral life cycle results in therapeutically active agents. Consequently HCV NS3 serine protease is also an attractive target for drug discovery.

Several potential HCV protease inhibitors have been described [PCT publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., Bioorg. Med. Chem. Lett., 8, pp. 1713-18 (1998); W. Han et al., Bioorg. Med. Chem. Lett., 10, 711-13 (2000); R. Dunsdon et al., Bioorg. Med. Chem. Lett., 10, pp. 1571-79 (2000); M. Llinas-Brunet et al., Bioorg. Med. Chem. Lett., 10, pp. 2267-70 (2000); and S. LaPlante et al., Bioorg. Med. Chem. Lett., 10, pp. 2271-74 (2000)].

Furthermore, the current understanding of HCV has not led to any other satisfactory anti-HCV agents or treatments. Until recently, the only established therapy for HCV disease was interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-Intron® and Pegasys®) and the combination therapy of ribavirin and pegylated interferon (Rebetrol®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides a compound of formula I:

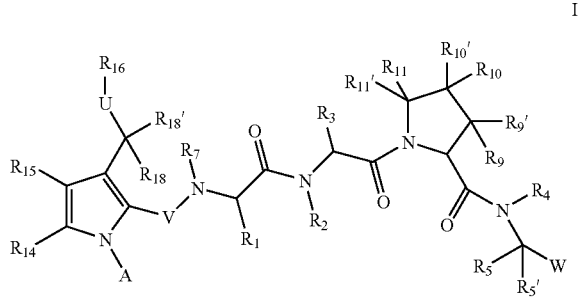

I or a pharmaceutically acceptable salt thereof,
wherein:
$R_9$ and $R_{9'}$ are each independently:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;
    wherein up to three aliphatic carbon atoms in each of $R_9$ and $R_{9'}$ are optionally replaced by O, N, NH, S, SO, or $SO_2$ in a chemically stable arrangement;
    wherein each of $R_9$ and $R_{9'}$ is independently and optionally substituted with up to 3 substituents independently selected from J;
      J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O) OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R') CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');
wherein;
each R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
  wherein up to 5 atoms in R' are optionally and independently substituted with J;
  wherein two R' groups bound to the same atom optionally form a 5- to 6-membered aromatic or a 3- to 7-membered saturated or partially unsaturated ring system having up to 3 heteroatoms independently selected from N, NH, O, S, SO, and $SO_2$, wherein said ring is optionally fused to a (C6-C10) aryl, (C5-C10)heteroaryl, (C3-C10)cycloalkyl, or a (C3-C10)heterocyclyl, wherein any ring has up to 3 substituents selected independently from J;
$R_{10}$, $R_{10'}$, $R_{11}$, and $R_{11'}$, are each independently:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
  wherein any ring is optionally fused to a (C6-C10)aryl, (C5-C10)heteroaryl, (C3-C10)cycloalkyl, or (C3-C10)heterocyclyl;
  wherein up to 3 aliphatic carbon atoms in each of $R_{10}$, $R_{10'}$, $R_{11}$, and $R_{11'}$ are optionally replaced by a heteroatom selected from O, NH, S, SO, or $SO_2$ in a chemically stable arrangement;
  wherein each of $R_{10}$, $R_{10'}$, $R_{11}$, and $R_{11'}$ is independently and optionally substituted with up to 3 substituents independently selected from J; or
$R_{10}$ is —OR' and $R_{10'}$ is H; or
$R_{10}$ and $R_{10'}$ are both —OR' or —SR'; or
$R_{10}$ and $R_{10'}$ are both fluorine; or
$R_{10}$ and $R_{10'}$ are optionally taken together with the carbon atom to which they are bound to form a 5- to 7-membered saturated or partially unsaturated ring system;
  wherein the $R_{10}$ and $R_{10'}$ atoms bound to the carbon atom are independently C(H), N, NH, O, S, SO, or $SO_2$;
  wherein said ring optionally contains up to 4 heteroatoms independently selected from N, NH, O, S, SO, and $SO_2$;
  wherein any atom is optionally singly or multiply substituted with up to 2 substituents selected independently from J; and
  wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J; or R₉ and R₁₀ are optionally taken together with the ring atoms to which they are bound to form a 5- to 6-membered aromatic or a 3- to 7-membered saturated or partially unsaturated ring system up to 3 heteroatoms independently selected from N, NH, O, S, SO, or SO₂; wherein said ring system is optionally substituted with up to 3 substituents selected independently from J; or R₁₀ and R₁₁ are optionally taken together with the ring atoms to which they are bound to form a 5- to 6-membered aromatic or a 3- to 7-membered saturated or partially unsaturated ring system having up to 3 heteroatoms independently selected from N, NH, O, S, SO, or SO₂; wherein said ring is optionally substituted with up to 3 substituents selected independently from J; or R₉ and R₁₁ are optionally taken together with the ring atoms to which they are bound to form a bridged bicyclic saturated or partially unsaturated carbocyclic or heterocyclic ring system containing up to 10 atoms; wherein said ring system is optionally substituted with up to 3 substituents selected independently from J; wherein each heteroatom in the heterocyclic ring system is selected from the group consisting of N, NH, O, S, SO, or SO₂;

R₁ and R₃ are each independently:
  (C1-C12)-aliphatic-,
  (C3-C10)-cycloalkyl- or -cycloalkenyl-,
  [(C3-C10)-cycloalkyl- or -cycloalkenyl]-(C1-C12)-aliphatic-,
  (C6-C10)-aryl-(C1-C12)aliphatic-, or
  (C5-C10)-heteroaryl-(C1-C12)-aliphatic-;
    wherein up to 3 aliphatic carbon atoms in each of R₁ and R₃ are optionally replaced by a heteroatom selected from O, N, NH, S, SO, or SO₂ in a chemically stable arrangement;
    wherein each of R₁ and R₃ is independently and optionally substituted with up to 3 substituents independently selected from J;

R₂, R₄, and R₇ are each independently:
  hydrogen-,
  (C1-C12)-aliphatic-,
  (C3-C10)-cycloalkyl-(C1-C12)-aliphatic-, or
  (C6-C10)-aryl-(C1-C12)-aliphatic-;
    wherein up to two aliphatic carbon atoms in each of R₂, R₄, and R₇ are optionally replaced by a heteroatom selected from O, N, NH, S, SO, and SO₂ in a chemically stable arrangement;
    wherein each of R₂, R₄, and R₇ is optionally substituted with up to 3 substituents independently selected from J;

R₅ and R₅' are each independently hydrogen or (C1-C12)-aliphatic, wherein any hydrogen is optionally replaced with halogen; wherein any terminal carbon atom of R₅ is optionally substituted with sulfhydryl or hydroxy; or R₅ is Ph or —CH₂Ph and R₅' is H, wherein said Ph or —CH₂Ph group is optionally substituted with up to 3 substituents independently selected from J; or R₅ and R₅' together with the atom to which they are bound optionally form a 3- to 6-membered saturated or partially unsaturated ring having up to 2 heteroatoms selected from N, NH, O, SO, and SO₂; wherein said ring is optionally substituted with up to 2 substituents selected independently from J;

W is:

[chemical structures]

wherein m is 0 or 1;
wherein each R₆ is independently:
  hydrogen-,
  (C1-C12)-aliphatic-,
  (C6-C10)-aryl-,
  (C6-C10)-aryl-(C1-C12)aliphatic-,
  (C3-C10)-cycloalkyl- or cycloalkenyl-,
  [(C3-C10)-cycloalkyl- or cycloalkenyl]-(C1-C12)-aliphatic-,
  (C3-C10)-heterocyclyl-,
  (C3-C10)-heterocyclyl-(C1-C12)-aliphatic-,
  (C5-C10)-heteroaryl-, or
  (C5-C10)-heteroaryl-(C1-C12)-aliphatic-;
  wherein up to 3 aliphatic carbon atoms in each R₆ is optionally replaced by a heteroatom selected from O, NH, S, SO, or SO₂ in a chemically stable arrangement;
  wherein R₆ is optionally substituted with up to 3 J substituents; or
  two R₆ groups, together with the nitrogen atom to which they are bound, optionally form a 5- to 6-membered aromatic or a 3- to 7-membered saturated or partially unsaturated ring system having up to 3 heteroatoms independently selected from N, NH, O, S, SO, and SO₂, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;

wherein each $R_8$ is independently —OR'; or the $R_8$ groups together with the boron atom, is a (C3-C10)-membered heterocyclic ring having in addition to the boron up to 3 additional heteroatoms selected from N, NR', O, SO, and $SO_2$;

V is —C(O)—, —C(S)—, —S(O)—, or —S(O)$_2$, —;

A is hydrogen or —C($R_{12}$)($R_{12'}$)-T-$R_{13}$;

T is oxygen or a bond;

$R_{12}$ and $R_{12'}$ are each independently:
  hydrogen-, or
  (C1-C6)-aliphatic-;
    wherein up to two aliphatic carbon atoms in each of $R_{12}$ and $R_{12'}$ are optionally replaced by a heteroatom selected from O, N, NH, S, SO, and $SO_2$ in a chemically stable arrangement; or
$R_{12}$ is absent and $R_{12'}$ is =O;

$R_{13}$ is —C(O)R', —P(O)(OR')$_2$, —SO$_3$R', —R', or $R_{19}$;

$R_{19}$ is:
  hydrogen,
  (C1-C12)-aliphatic-,
  (C6-C10)-aryl-(C1-C12)aliphatic-, or
  (C5-C10)-heteroaryl-(C1-C12)-aliphatic-;
    wherein $R_{19}$ is optionally substituted with up to 3 J substituents;
    wherein up to 3 aliphatic carbon atoms in each $R_{19}$ are optionally replaced by a heteroatom selected from O, $NR_{19}$, S, SO, or $SO_2$ in a chemically stable arrangement;
    wherein up to 3 aliphatic carbon atoms in each $R_{19}$ are optionally replaced with —C(O)—;
    wherein $R_{19}$ is optionally substituted with up to 3 J substituents;
    wherein any $NR_{19}$, taken together with the nitrogen and a carbon adjacent to the nitrogen, optionally forms a 5- to 7-membered ring system, wherein said ring system optionally contains up to three additional heteroatoms selected from O, N, NH, S, SO, and $SO_2$ in a chemically stable arrangement;

$R_{14}$ and $R_{15}$ are independently halogen, —OR', —OC(O)N(R')$_2$, —NO$_2$, —CN, —CF$_3$, —OCF$_3$, —R', 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, or —(CH$_2$)$_{0-2}$NHC(O)R';

$R_{16}$ is R', —C(O)R', —P(O)(OR')$_2$, or —SO$_3$R';

U is O, N, or a bond;

$R_{18}$ and $R_{18'}$ are optionally taken together with the carbon atom to which they are bound to form a 5- to 7-membered saturated or partially unsaturated ring system;
  wherein the $R_{18}$ and $R_{18'}$ atoms bound to the carbon atom are independently O or N;
  wherein said ring optionally contains up to 1 additional heteroatom selected from N, NH, O, S, SO, and $SO_2$;
  wherein any substitutable atom is optionally singly or multiply substituted with up to 2 substituents selected independently from J;
  wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;
  provided that when $R_{18}$ and $R_{18'}$ are optionally taken together with the carbon atom to which they are bound to form a 5- to 7-membered saturated or partially unsaturated ring system, then $R_{16}$ is R'; or $R_{18'}$ is =O, =CH$_2$, =N(R'), or =N(OR') and $R_{18}$ is absent, provided that when $R_{18}$ is absent and $R_{18'}$ is =CH$_2$, then U is oxygen; and provided that when $R_{18}$ is absent and $R_{18'}$ is =O, =N(R') or =N(OR'), then U is a bond and $R_{16}$ is R'.

The invention also relates to processes for preparing the above compounds and to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

DETAILED DESCRIPTION OF THE INVENTION

The present invention provides a compound of formula I:

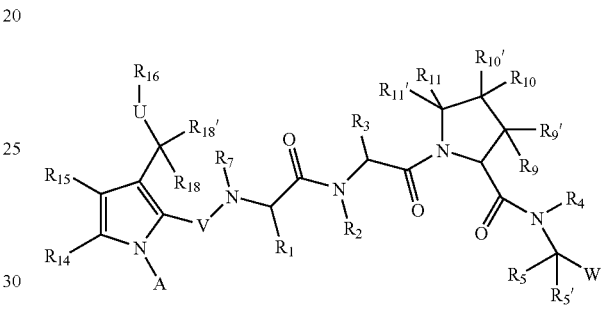

I or a pharmaceutically acceptable salt thereof, wherein:

$R_9$ and $R_{9'}$ are each independently:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;
    wherein up to three aliphatic carbon atoms in each of $R_9$ and $R_{9'}$ are optionally replaced by O, N, NH, S, SO, or $SO_2$ in a chemically stable arrangement;
    wherein each of $R_9$ and $R_{9'}$ is independently and optionally substituted with up to 3 substituents independently selected from J;

J is halogen, —OR', —NO$_2$, —CN, —CF$_3$, —OCF$_3$, —R', oxo, thioxo, =N(R'), =N(OR'), 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');
  wherein;

each R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom optionally form a 5- to 6-membered aromatic or a 3- to 7-membered saturated or partially unsaturated ring system having up to 3 heteroatoms independently selected from N, NH, O, S, SO, and $SO_2$, wherein said ring is optionally fused to a (C6-C10) aryl, (C5-C10)heteroaryl, (C3-C10)cycloalkyl, or a (C3-C10)heterocyclyl, wherein any ring has up to 3 substituents selected independently from J;

$R_{10}$, $R_{10'}$, $R_{11}$, and $R_{11'}$ are each independently:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein any ring is optionally fused to a (C6-C10)aryl, (C5-C10)heteroaryl, (C3-C10)cycloalkyl, or (C3-C10)heterocyclyl;
wherein up to 3 aliphatic carbon atoms in each of $R_{10}$, $R_{10'}$, $R_{11}$, and $R_{11'}$ are optionally replaced by a heteroatom selected from O, NH, S, SO, or $SO_2$ in a chemically stable arrangement;
wherein each of $R_{10}$, $R_{10'}$, $R_{11}$, and $R_{11'}$ is independently and optionally substituted with up to 3 substituents independently selected from J; or $R_{10}$ is —OR' and $R_{10'}$ is H; or
$R_{10}$ and $R_{10'}$ are both —OR' or —SR'; or
$R_{10}$ and $R_{10'}$ are both fluorine; or
$R_{10}$ and $R_{10'}$ are optionally taken together with the carbon atom to which they are bound to form a 5- to 7-membered saturated or partially unsaturated ring system;
wherein the $R_{10}$ and $R_{10'}$ atoms bound to the carbon atom are independently C(H), N, NH, O, S, SO, or $SO_2$;
wherein said ring optionally contains up to 4 heteroatoms independently selected from N, NH, O, S, SO, and $SO_2$;
wherein any atom is optionally singly or multiply substituted with up to 2 substituents selected independently from J; and
wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J; or $R_9$ and $R_{10}$ are optionally taken together with the ring atoms to which they are bound to form a 5- to 6-membered aromatic or a 3- to 7-membered saturated or partially unsaturated ring system up to 3 heteroatoms independently selected from N, NH, O, S, SO, or $SO_2$; wherein said ring system is optionally substituted with up to 3 substituents selected independently from J; or $R_{10}$ and $R_{11}$ are optionally taken together with the ring atoms to which they are bound to form a 5- to 6-membered aromatic or a 3- to 7-membered saturated or partially unsaturated ring system having up to 3 heteroatoms independently selected from N, NH, O, S, SO, or $SO_2$; wherein said ring is optionally substituted with up to 3 substituents selected independently from J; or $R_9$ and $R_{11}$ are optionally taken together with the ring atoms to which they are bound to form a bridged bicyclic saturated or partially unsaturated carbocyclic or heterocyclic ring system containing up to 10 atoms; wherein said ring system is optionally substituted with up to 3 substituents independently from J; wherein each heteroatom in the heterocyclic ring system is selected from the group consisting of N, NH, O, S, SO, or $SO_2$;

$R_1$ and $R_3$ are each independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in each of $R_1$ and $R_3$ are optionally replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;

$R_2$, $R_4$, and $R_7$ are each independently:
hydrogen-,
(C1-C12)-aliphatic-,
(C3-C10)-cycloalkyl-(C1-C12)-aliphatic-, or
(C6-C10)-aryl-(C1-C12)-aliphatic-;
wherein up to two aliphatic carbon atoms in each of $R_2$, $R_4$, and $R_7$ are optionally replaced by a heteroatom selected from O, N, NH, S, SO, and $SO_2$ in a chemically stable arrangement;
wherein each of $R_2$, $R_4$, and $R_7$ is optionally substituted with up to 3 substituents independently selected from J;

$R_5$ and $R_{5'}$ are each independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or $R_5$ and $R_{5'}$ together with the atom to which they are bound optionally form a 3- to 6-membered saturated or partially unsaturated ring having up to 2 heteroatoms selected from N, NH, O, SO, and $SO_2$; wherein said ring is optionally substituted with up to 2 substituents selected independently from J;

W is:

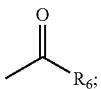 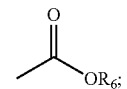 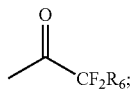

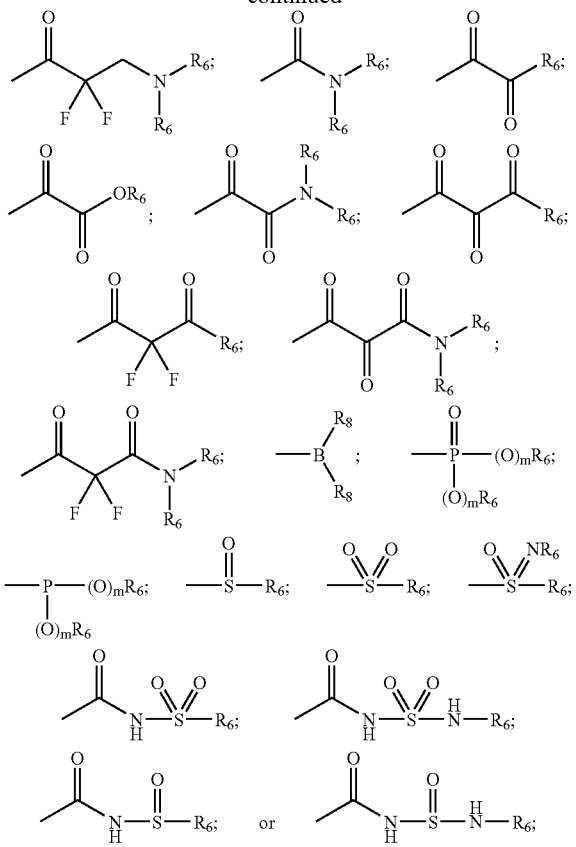

wherein m is 0 or 1;
wherein each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
  wherein up to 3 aliphatic carbon atoms in each $R_6$ is optionally replaced by a heteroatom selected from O, NH, S, SO, or $SO_2$ in a chemically stable arrangement;
  wherein $R_6$ is optionally substituted with up to 3 J substituents; or
  two $R_6$ groups, together with the nitrogen atom to which they are bound, optionally form a 5- to 6-membered aromatic or a 3- to 7-membered saturated or partially unsaturated ring system having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;
  wherein each $R_8$ is independently —OR'; or the $R_8$ groups together with the boron atom, is a (C3-C10)-membered heterocyclic ring having in addition to the boron up to 3 additional heteroatoms selected from N, NR', O, SO, and $SO_2$;

V is —C(O)—, —C(S)—, —S(O)—, or —S(O)$_2$—;
A is hydrogen or —C($R_{12}$)($R_{12'}$)-T-$R_{13}$;
T is oxygen or a bond;
$R_{12}$ and $R_{12'}$ are each independently:
  hydrogen-, or
  (C1-C6)-aliphatic-;
    wherein up to two aliphatic carbon atoms in each of $R_{12}$ and $R_{12'}$ are optionally replaced by a heteroatom selected from O, N, NH, S, SO, and $SO_2$ in a chemically stable arrangement; or
  $R_{12}$ is absent and $R_{12'}$ is =O;
$R_{13}$ is —C(O)R', —P(O)(OR')$_2$, —SO$_3$R', —R', or —$R_{19}$;
$R_{19}$ is:
  hydrogen,
  (C1-C12)-aliphatic-,
  (C6-C10)-aryl-(C1-C12)aliphatic-, or
  (C5-C10)-heteroaryl-(C1-C12)-aliphatic-;
    wherein up to 3 aliphatic carbon atoms in each $R_{19}$ are optionally replaced by a heteroatom selected from O, $NR_{19}$, S, SO, or $SO_2$ in a chemically stable arrangement;
    wherein up to 3 aliphatic carbon atoms in each $R_{19}$ are optionally replaced with —C(O)—;
    wherein $R_{19}$ is optionally substituted with up to 3 J substituents;
    wherein any $NR_{19}$, taken together with the nitrogen and a carbon adjacent to the nitrogen, optionally forms a 5- to 7-membered ring system, wherein said ring system optionally contains up to three additional heteroatoms selected from O, N, NH, S, SO, and $SO_2$ in a chemically stable arrangement;
$R_{14}$ and $R_{15}$ are independently halogen, —OR', —OC(O)N(R')$_2$, —NO$_2$, —CN, —CF$_3$, —OCF$_3$, —R', 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, or —(CH$_2$)$_{0-2}$NHC(O)R';
$R_{16}$ is R', —C(O)R', —P(O)(OR')$_2$, or —SO$_3$R';
U is O, N, or a bond; and
$R_{18}$ and $R_{18'}$ are optionally taken together with the carbon atom to which they are bound to form a 5- to 7-membered saturated or partially unsaturated ring system;
  wherein the $R_{18}$ and $R_{18'}$ atoms bound to the carbon atom are independently O or N;
  wherein said ring optionally contains up to 1 additional heteroatom selected from N, NH, O, S, SO, and $SO_2$;
  wherein any substitutable atom is optionally singly or multiply substituted with up to 2 substituents selected independently from J;
  wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;
  provided that when $R_{18}$ and $R_{18'}$ are optionally taken together with the carbon atom to which they are bound to form a 5- to 7-membered saturated or partially unsaturated ring system, then $R_{16}$ is R'; or
$R_{18'}$ is =O, =CH$_2$, =N(R'), or =N(OR') and $R_{18}$ is absent, provided that when $R_{18}$ is absent and $R_{18'}$ is =CH$_2$, then U is oxygen; and
  provided that when $R_{18}$ is absent and $R_{18'}$ is =O, =N(R') or =N(OR'), then U is a bond and $R_{16}$ is R'.

Definitions

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring.

The term "heterocyclyl" as used herein means a monocyclic or bicyclic non-aromatic ring system having 1 to 3 heteroatom or heteroatom groups in each ring selected from O, N, NH, S, SO, and $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a C5, C6, C7, C8, C9, and C10 monocyclic or bicyclic non-aromatic ring system having 1 to 3 heteroatom or heteroatom groups in each ring selected from O, N, NH, and S in a chemically stable arrangement.

The term "heteroaryl" as used herein means a monocyclic or bicyclic aromatic ring system having 1 to 3 heteroatom or heteroatom groups in each ring selected from O, N, NH, and S in a chemically stable arrangement. In such a bicyclic aromatic ring system embodiment of "heteroaryl":

one or both rings may be aromatic; and one or both rings may contain said heteroatom or heteroatom groups. It is understood that as used herein, the term "(C5-C10)-heteroaryl-" includes any one of a C5, C6, C7, C8, C9, and C10 monocyclic or bicyclic aromatic ring system having 1 to 3 heteroatom or heteroatom groups in each ring selected from O, N, NH, and S in a chemically stable arrangement.

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is also understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

Preferred Embodiments

According to an embodiment of compounds of formula I, V is —C(O)—.

According to another embodiment, the present invention provides a compound of formula IA:

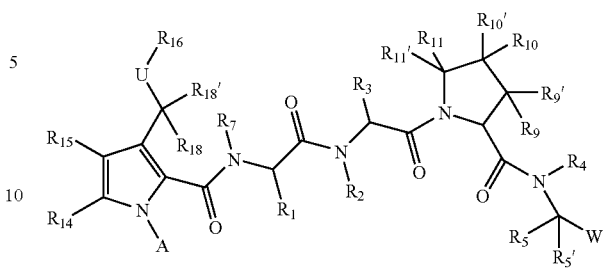

wherein:
$R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{14}$, $R_{15}$, $R_{16}$, $R_{18}$, $R_{18'}$, A, U, and W are as defined in any of the embodiments herein.

According to another embodiment of compounds of formula I,
A is —C($R_{12}$)($R_{12'}$)-T-$R_{13}$;
$R_{12}$ and $R_{12'}$ are both hydrogen;
T is oxygen;
$R_{13}$ is —C(O)R', —P(O)(OR')$_2$, —SO$_3$R', or —R';
$R_{14}$ and $R_{15}$ are both —R';
$R_{18'}$ is =O and $R_{18}$ is absent;
U is a bond; and
$R_{16}$ is R', wherein R' is selected from:
(C1-C12)-aliphatic-,
(C3-C10)-cycloalkyl- or -cycloalkenyl-,
[(C3-C10)-cycloalkyl or -cycloalkenyl]-(C1-C12)-aliphatic-;
wherein up to 5 atoms in R' are optionally and independently substituted with J.

According to another embodiment of compounds of formula I,
$R_{13}$ is —C(O)R', —P(O)(OR')$_2$, or —R';
$R_{14}$ and $R_{15}$ are both —R' and R' is (C1-C12)-aliphatic-; and
$R_{16}$ is R', wherein R' is (C1-C12)-aliphatic-.

According to another embodiment, the present invention provides a compound of formula IB:

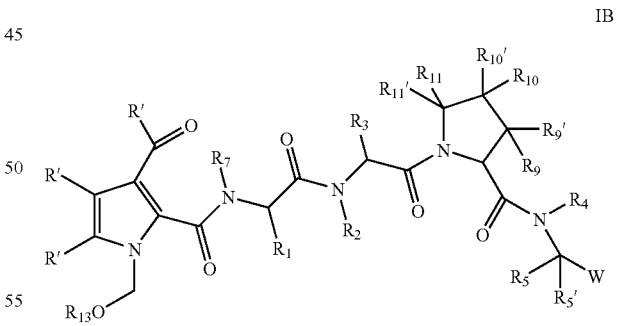

wherein:
R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{13}$, and W are as defined in any of the embodiments herein.

According to an embodiment of compounds of formula IB, $R_{16}$ is —R' wherein R' is preferably methyl; $R_{14}$ and $R_{15}$ are both —R' and R' is preferably methyl; $R_{13}$ is —C(O)R' or —P(O)(OR')$_2$, wherein R' is as defined in any of the embodiments herein; and $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to another embodiment of compounds of formula I,
A is —C($R_{12}$)($R_{12'}$)-T-$R_{13}$;
$R_{12}$ is hydrogen and $R_{12'}$ is (C1-C6)-aliphatic-;
    wherein up to two aliphatic carbon atoms in $R_{12'}$ are optionally replaced by a heteroatom selected from O, N, NH, S, SO, and $SO_2$ in a chemically stable arrangement;
T is oxygen;
$R_{13}$ is —C(O)R', —P(O)(OR')$_2$, —$SO_3$R', or —R';
$R_{14}$ and $R_{15}$ are both —R';
$R_{18'}$ is =O and $R_{18}$ is absent;
U is a bond; and
$R_{16}$ is R', wherein R' is selected from:
    (C1-C12)-aliphatic-,
    (C3-C10)-cycloalkyl- or -cycloalkenyl-,
    [(C3-C10)-cycloalkyl or -cycloalkenyl]-(C1-C12)-aliphatic-;
        wherein up to 5 atoms in R' are optionally and independently substituted with J.

According to another embodiment of compounds of formula I,
$R_{12'}$ is (C1-C6)-aliphatic-;
$R_{13}$ is —C(O)R', —P(O)(OR')$_2$, or —R';
$R_{14}$ and $R_{15}$ are both —R' and R' is (C1-C12)-aliphatic-;
$R_{16}$ is R', wherein R' is (C1-C12)-aliphatic-.

According to another embodiment, the present invention provides a compound of formula IC:

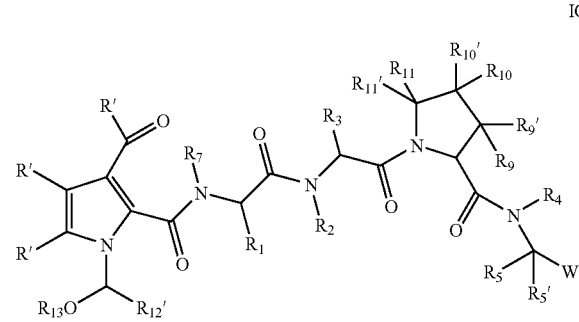

IC wherein:
    R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{12'}$, $R_{13}$, and W are as defined in any of the embodiments herein.

According to an embodiment of compounds of formula IC, $R_{16}$ is —R' wherein R' is preferably methyl; $R_{14}$ and $R_{15}$ are both —R' and R' is preferably methyl; $R_{13}$ is —C(O)R' or —P(O)(OR')$_2$, wherein R' is as defined in any of the embodiments herein; $R_{12'}$ is methyl and $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to another embodiment of compounds of formula I,
A is —C($R_{12}$)($R_{12'}$)-T-$R_{13}$;
$R_{12}$ is absent and $R_{12'}$ is =O;
T is oxygen or a bond;
$R_{13}$ is —$R_{19}$;
$R_{14}$ and $R_{15}$ are both —R';
$R_{18'}$ is =O and $R_{18}$ is absent;
U is a bond; and
$R_{16}$ is R', wherein R' is selected from:
    (C1-C12)-aliphatic-,
    (C3-C10)-cycloalkyl- or -cycloalkenyl-,
    [(C3-C10)-cycloalkyl or -cycloalkenyl]-(C1-C12)-aliphatic-;
    wherein up to 5 atoms in R' are optionally and independently substituted with J.

According to another embodiment, the present invention provides a compound of formula ID:

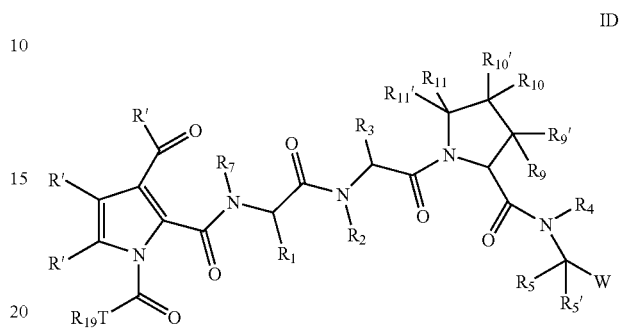

ID wherein:
    R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{12'}$, $R_{19}$, T, and W are as defined in any of the embodiments herein.

According to an embodiment of compounds of formula ID, $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein;
T is a bond;
$R_{16}$ is —R' wherein R' is preferably methyl;
$R_{14}$ and $R_{15}$ are both —R' and R' is preferably methyl;
$R_{13}$ is $R_{19}$, wherein $R_{19}$ is as defined in any of the embodiments herein.

According to another embodiment of compounds of formula ID, $R_{19}$ is:
    (C1-C12)-aliphatic-,
        wherein 1 to 2 aliphatic carbon atoms in each $R_{19}$ are optionally replaced by a heteroatom selected from O or $NR_{19}$, in a chemically stable arrangement;
        wherein 1 to 2 aliphatic carbon atoms in each $R_{19}$ is optionally replaced with —C(O)—;
        wherein $R_{19}$ is optionally substituted with up to 3 J substituents.

According to a preferred embodiment of compounds of formula ID, $R_{19}$ is:
    (C3-C6)-aliphatic-,
        wherein 1 to 2 aliphatic carbon atoms in each $R_{19}$ are optionally replaced by a heteroatom selected from O or $NR_{19}$, in a chemically stable arrangement;
        wherein 1 to 2 aliphatic carbon atoms in each $R_{19}$ is optionally replaced with —C(O)—;
        wherein $R_{19}$ is optionally substituted with up to 3 J substituents.

According to another embodiment of compounds of formula I,
$R_{18'}$ is =$CH_2$, and $R_{18}$ is absent;
U is oxygen;
$R_{16}$ is R', —C(O)R', —P(O)(OR')$_2$, or —$SO_3$R';
$R_{14}$ and $R_{15}$ are both —R'; and
A is hydrogen.

According to another embodiment of compounds of formula I,
$R_{16}$ is R', —C(O)R', or —P(O)(OR')$_2$;
$R_{14}$ and $R_{15}$ are both —R' and R' is (C1-C12)-aliphatic-.

According to another embodiment, the present invention provides a compound of formula IE:

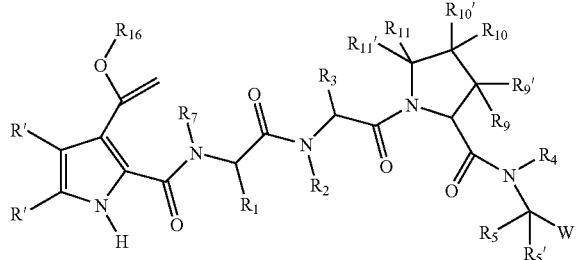

IE wherein:

R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{16}$, and W are as defined in any of the embodiments herein.

According to an embodiment of compounds of formula IE, $R_{16}$ is —C(O)R', —P(O)(OR')$_2$,; $R_{14}$ and $R_{15}$ are both —R' and R' is preferably methyl; A is hydrogen; and $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to an embodiment of compounds of formula I, $R_{18'}$ is =N(R') or =N(OR') and $R_{18}$ is absent;
U is a bond;
$R_{16}$ is R';
$R_{14}$ and $R_{15}$ are both —R'; and
A is hydrogen.

In another embodiment of compounds of formula I, U is —NR'—.

According to another embodiment of compounds of formula I, $R_{14}$ and $R_{15}$ are both —R' and R' is (C1-C12)-aliphatic-.

According to another embodiment, the present invention provides a compound of formula IF:

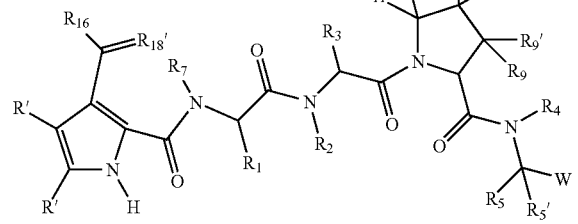

IF wherein:

R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, $R_{16}$, $R_{18'}$, and W are as defined in any of the embodiments herein.

According to an embodiment of compounds of formula IF, $R_{18'}$ is =N(R') or =N(OR') and $R_{18}$ is absent; $R_{16}$ is R'; $R_{14}$ and $R_{15}$ are both —R' and R' is preferably methyl; A is hydrogen; and $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to another embodiment of compounds of formula I,
$R_{18}$ and $R_{18'}$ are optionally taken together with the carbon atom to which they are bound to form a 5- to 7-membered saturated or partially unsaturated ring system;
wherein the $R_{18}$ and $R_{18'}$ atoms bound to the carbon atom are independently O or N;
wherein said ring optionally contains up to 1 additional heteroatom selected from N, NH, O, S, SO, and SO$_2$;
wherein any substitutable atom is optionally singly or multiply substituted with up to 2 substituents selected independently from J;
wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;
U is a bond;
$R_{16}$ is R';
$R_{14}$ and $R_{15}$ are both —R'; and
A is hydrogen.

According to another embodiment of compounds of formula I,
the $R_{18}$ and $R_{18'}$ atoms bound to the carbon atom are O and the ring formed when $R_{18}$ and $R_{18'}$ are optionally taken together with the carbon atom to which they are bound optionally contains up to 1 additional oxygen atom and is optionally substituted with up to 2 J substituents.

According to another embodiment, the present invention provides a compound of formula IG:

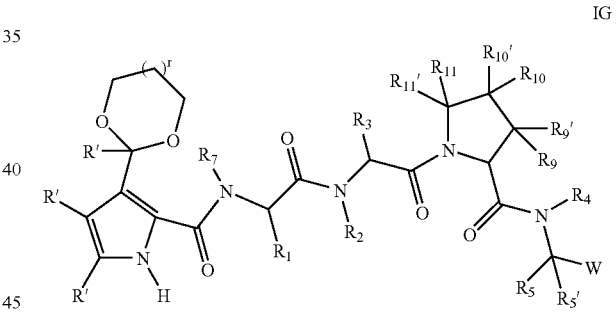

IG wherein:

r is 0, 1, or 2, $R_{16}$ is R', R', $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to an embodiment of compounds of formula IG, the $R_{18}$ and $R_{18'}$ atoms bound to the carbon atom are O; the ring formed when $R_{18}$ and $R_{18'}$ are optionally taken together with the carbon atom to which they are bound is a 5- or 6-membered ring system optionally substituted with up to 2 J substituents; $R_{16}$ is R'; $R_{14}$ and $R_{15}$ are both —R' and R' is preferably methyl; A is hydrogen; and $R_1$, $R_2$, $R_3$, $R_4$, $R_5$, $R_{5'}$, $R_7$, $R_9$, $R_{9'}$, $R_{10}$, $R_{10'}$, $R_{11}$, $R_{11'}$, and W are as defined in any of the embodiments herein.

According to another embodiment, this invention does not include compounds wherein T is 3-acetyl-4,5-dimethyl-1H-pyrrole (e.g., see compounds 63-64 at page 95, and compounds 66-67 at page 96 of WO 03/087092).

According to another embodiment, this invention does not include compounds wherein:
V is —C(O)—, —C(S)—, —S(O)—, or —S(O)$_2$—; and radical T is:

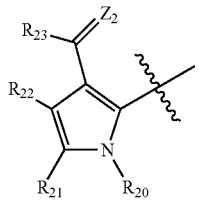

wherein:
R$_{20}$ is —H, —S(O)R$^O$, —S(O)$_2$R$^O$, —C(O)R$^O$, —C(O)OR$^O$, —C(O)N(R$^O$)$_2$, —N(R$^O$)C(O)R$^O$, —N(COR$^O$)COR$^O$, —SO$_2$N(R$^O$)$_2$, —SO$_3$R$^O$, —C(O)C(O)R$^O$, —C(O)CH$_2$C(O)R$^O$, —C(S)R$^O$, —C(S)N(R$^O$)$_2$, —(CH$_2$)$_{0-2}$NHC(O)R$^O$, —N(R$^O$)N(R$^O$)COR$^O$, —N(R$^O$)N(R$^O$)C(O)OR$^O$, —N(R$^O$)N(R$^O$)CON(R$^O$)$_2$, —N(R$^O$)SO$_2$R$^O$, —N(R$^O$)SO$_2$N(R$^O$)$_2$, —N(R$^O$)C(O)OR$^O$, —N(R$^O$)C(O)R$^O$, —N(R$^O$)C(S)R$^O$, —N(R$^O$)C(O)N(R$^O$)$_2$, —N(R$^O$)C(S)N(R$^O$)$_2$, —N(COR$^O$)COR$^O$, —N(OR$^O$)R$^O$, —C(=NH)N(R$^O$)$_2$, —C(O)N(OR$^O$)R$^O$, —C(=NOR$^O$)R$^O$, —OP(O)(OR$^O$)$_2$, —P(O)(R$^O$)$_2$, —P(O)(OR$^O$)$_2$, or —P(O)(H)(OR$^O$);

R$_{21}$ and R$_{22}$ are independently halogen, —OR$^O$, —OC(O)N(R$^O$)$_2$, —NO$_2$, —CN, —CF$_3$, —OCF$_3$, —R$^O$, oxo, 1,2-methylenedioxy, 1,2-ethylenedioxy, —N(R$^O$)$_2$, —SRO, —SOR$^O$, —SO$_2$R$^O$, —SO$_2$N(R$^O$)$_2$, —SO$_3$R$^O$, —C(O)R$^O$, —C(O)C(O)R$^O$, —C(O)CH$_2$C(O)R$^O$, —C(S)R$^O$, —C(O)OR$^O$, —OC(O)R$^O$, —C(O)N(R$^O$)$_2$, —OC(O)N(R$^O$)$_2$, —C(S)N(R$^O$)$_2$, —(CH$_2$)$_{0-2}$NHC(O)R$^O$;

Z$_2$ is =O, =NR$^O$, =NOR$^O$, or =CH$_2$;
R$_{23}$ is —OR$^O$, —CF$_3$, —OCF$_3$, —R$^O$, —N(R$^O$)$_2$, —C(O)R$^O$, or —N(R$^O$)COR$^O$;

two R$^O$ groups together with the atoms to which they are bound form a 3- to 10-membered aromatic or non-aromatic ring having up to 3 heteroatoms independently selected from N, NH, O, S, SO, or SO$_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J$_3$; or
each R$^O$ is independently selected from:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-,
wherein R$^O$ has up to 3 substituents selected independently from J$_3$; and J$_3$ is halogen, —OR$^O$, —OC(O)N(R$^O$)$_2$, —NO$_2$, —CN, —CF$_3$, —OCF$_3$, —R$^O$, oxo, thioxo, 1,2-methylenedioxy, —N(R$^O$)$_2$, —SR$^O$, —SOR$^O$, —SO$_2$R$^O$, —SO$_2$N(R$^O$)$_2$, —SO$_3$R$^O$, —C(O)R$^O$, —C(O)C(O)R$^O$, —C(O)CH$_2$C(O)R$^O$, —C(S)R$^O$, —C(O)OR$^O$, —OC(O)R$^O$, —C(O)N(R$^O$)$_2$, —OC(O)N(R$^O$)$_2$, —C(S)N(R$^O$)$_2$, —(CH$_2$)$_{0-2}$NHC(O)R$^O$, —N(R$^O$)N(R$^O$)COR$^O$, —N(R$^O$)N(R$^O$)C(O)OR$^O$, —N(R$^O$)N(R$^O$)CON(R$_2$, —N(R$^O$)SO$_2$R$^O$, —N(R$^O$)SO$_2$N(R$^O$)$_2$, —N(R$^O$)C(O)OR$^O$, —N(R$^O$)C(O)R$^O$, —N(R$^O$)C(S)R$^O$, —N(R$^O$)C(O)N(R$^O$)$_2$, —N(R$^O$)C(S)N(R$^O$)$_2$, —N(COR$^O$)COR$^O$, —N(OR$^O$)R$^O$, —CN, —C(=NH)N(R$^O$)$_2$, —C(O)N(OR$^O$)R$^O$, —C(=NOR$^O$)R$^O$, —OP(O)(OR$^O$)$_2$, —P(O)(R$^O$)$_2$, —P(O)(OR$^O$)$_2$, or —P(O)(H)(OR$^O$)(e.g., see compounds of formula II at page 22 of WO 03/087092).

According to another embodiment of compounds of formula I, when R$_{18'}$ is =O, R$_{18}$ is absent, U is a bond, and R$_{16}$ is R', then A is —C(R$_{12}$)(R$_{12'}$)-T-R$_{13}$.

According to another embodiment of compounds of formula I, when A is hydrogen, R$_{16}$ is R', —C(O)R', —P(O)(OR')$_2$, or —SO$_3$R';
U is O, or N, or a bond; and
R$_{18}$ and R$_{18'}$ are optionally taken together with the carbon atom to which they are bound to form a 5- to 7-membered saturated or partially unsaturated ring system;
wherein the R$_{18}$ and R$_{18'}$ atoms bound to the carbon atom are independently O or N;
wherein said ring optionally contains up to 1 additional heteroatom selected from N, NH, O, S, SO, and SO$_2$;
wherein any substitutable atom is optionally singly or multiply substituted with up to 2 substituents selected independently from J;
wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;
provided that when R$_{18}$ and R$_{18'}$ are optionally taken together with the carbon atom to which they are bound to form a 5- to 7-membered saturated or partially unsaturated ring system, then R$_{16}$ is R'; or
R$_{18'}$ is =O, =CH$_2$, =N(R'), or =N(OR') and R$_{18}$ is absent, provided that when R$_{18}$ is absent and R$_{18'}$ is =CH$_2$, then U is oxygen; and
provided that when R$_{18}$ is absent and R$_{18'}$ is =O, =N(R') or =N(OR'), then U is a bond and R$_{16}$ is R'.

According to another embodiment of compounds of formula I, the

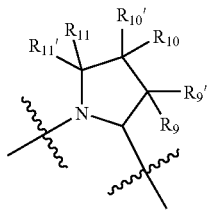

radical is:

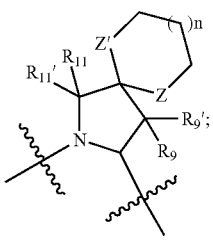

wherein:
n is 0, 1, or 2;
Z and Z' are independently C(H), N, NH, O, or S;

$R_9$, $R_{9'}$, $R_{11}$, and $R_{11'}$ are as defined in any of the embodiments herein; and the spirocyclic ring containing Z and Z' is optionally substituted with up to 3 J substituents, wherein J is as defined in any of the embodiments herein.

According to another embodiment the

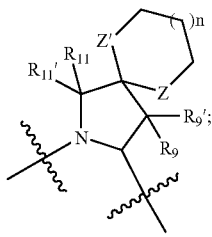

radical is:

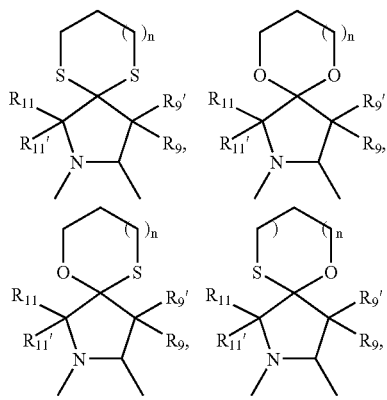

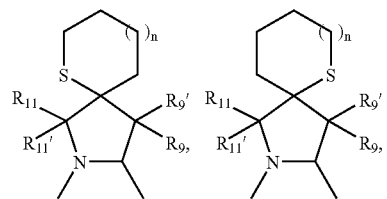

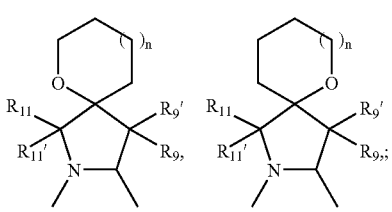

wherein:

$R_{11}$ and $R_{11'}$ are both H;

n is 0, 1, or 2;

$R_9$ and $R_{9'}$ are as defined in any of the embodiments herein; and the spirocyclic ring containing Z and Z' is optionally substituted with up to 3 J substituents, wherein J is as defined in any of the embodiments herein.

According to a preferred embodiment, the

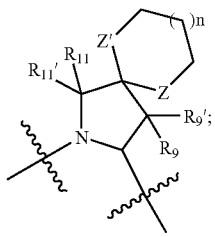

radical is:

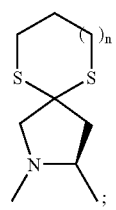

wherein:

n is 0 or 1.

According to another embodiment, the present invention provides a compound of formula IH:

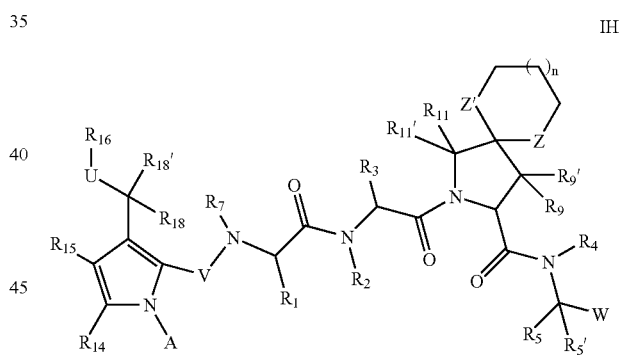

IH wherein:

$R_1$, $R_2$, $R_3$, $R_4$, $R_5$, $R_{5'}$, $R_7$, $R_9$, $R_{9'}$, $R_{11}$, $R_{11'}$, $R_{14}$, $R_{15}$, $R_{16}$, $R_{18}$, $R_{18'}$, n, V, A, U, Z, Z' and W are as defined in any of the embodiments herein.

According to another embodiment the

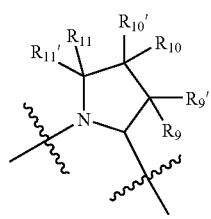

radical is:

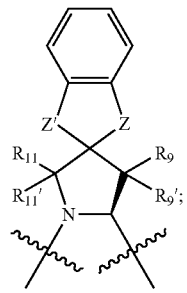

wherein:

Z and Z' are independently C(H), N, NH, O, or S;

$R_9$, $R_{9'}$, $R_{11}$, and $R_{11'}$ are as defined in any of the embodiments herein; and the fused benzo ring is optionally substituted with up to 3 J substituents, wherein J is as defined in any of the embodiments herein.

According to another embodiment, the present invention provides a compound of formula IJ:

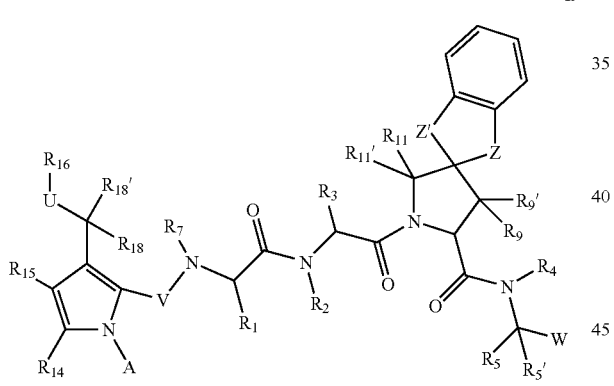

IJ wherein:

$R_1, R_2, R_3, R_4, R_5, R_{5'}, R_7, R_9, R_{9'}, R_{11}, R_{11'}, R_{14}, R_{15}, R_{16}, R_{18}, R_{18'}$, V, A, U, Z, Z' and W are as defined in any of the embodiments herein; and the fused benzo ring is optionally substituted with up to 3 J substituents, wherein J is as defined in any of the embodiments herein.

According to a preferred embodiment for compounds of formula IJ, Z and Z' are S, $R_9$ and $R_{9'}$ are H, $R_1, R_2, R_3, R_4, R_5, R_{5'}, R_7, R_{11}, R_{11'}, R_{14}, R_{15}, R_{16}, R_{18}, R_{18'}$ V, A, U, and W are as defined in any of the embodiments herein and the fused benzo ring is optionally substituted with up to 3 J substituents, wherein J is as defined in any of the embodiments herein.

According to another embodiment of compounds of formula I, the

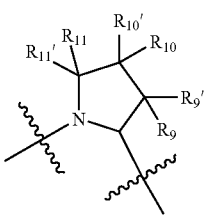

radical is:

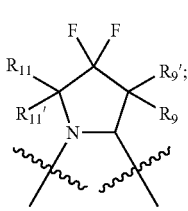

wherein:

$R_9, R_{9'}, R_{11}$, and $R_{11'}$ are H.

In a preferred embodiment, the

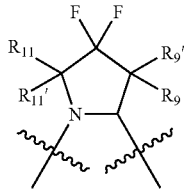

radical is:

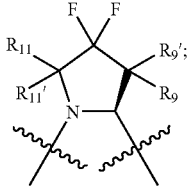

wherein:

$R_9, R_{9'}, R_{11}$, and $R_{11'}$ are H.

According to another embodiment, the present invention provides a compound of formula IK:

IK

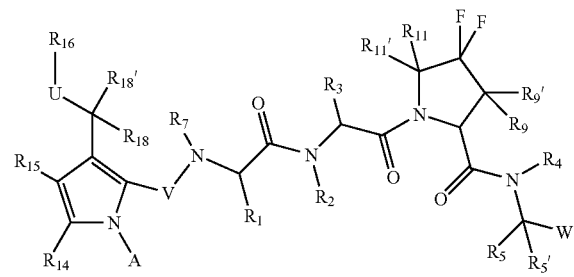

wherein:

$R_1, R_2, R_3, R_4, R_5, R_{5'}, R_7, R_9, R_{9'}, R_{11}, R_{11'}, R_{14}, R_{15}, R_{16}, R_{18}, R_{18'}$, V, A, U, and W are as defined in any of the embodiments herein.

According to another embodiment of compounds of formula I, in the

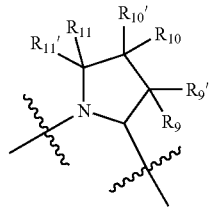

radical $R_9, R_{10}, R_{10'}, R_{11}$, and $R_{11'}$ are H; and $R_{9'}$ is:

(C1-C12)-aliphatic-, (C3-C10)-cycloalkyl- or -cycloalkenyl-;

wherein up to three aliphatic carbon atoms in $R_{9'}$ may be replaced by O, N, NH, S, SO, or $SO_2$;

wherein $R_{9'}$ is independently and optionally substituted with up to 3 substituents independently selected from J.

According to another embodiment of compounds of formula I, the

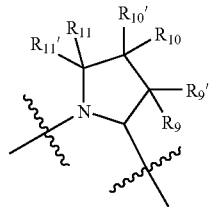

radical is:

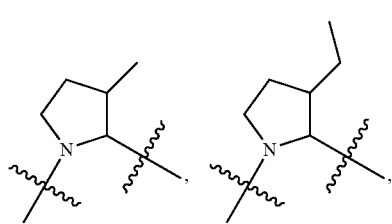

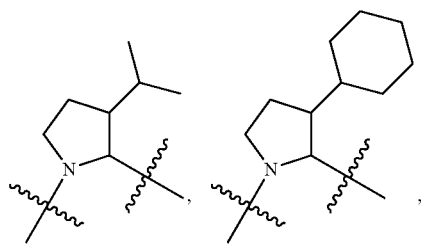

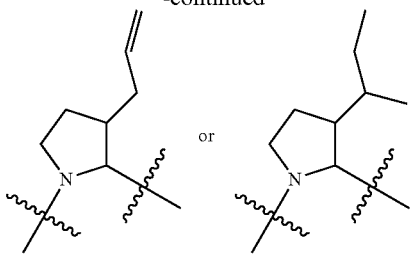

According to another embodiment of compounds of formula I, in the

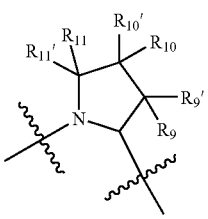

radical $R_9, R_{9'}, R_{10}, R_{11}$, and $R_{11'}$ are H; and $R_{10'}$ is:

(C1-C12)-aliphatic-, (C3-C10)-cycloalkyl- or -cycloalkenyl-, (C6-C10)-aryl-, wherein any ring is optionally fused to a (C6-C10)aryl, (C5-C10)heteroaryl, (C3-C10)cycloalkyl, or (C3-C10) heterocyclyl;

wherein up to 3 aliphatic carbon atoms in $R_{10'}$ may be replaced by a heteroatom selected from O, NH, S, SO, or $SO_2$ in a chemically stable arrangement;

wherein $R_{10'}$ is independently and optionally substituted with up to 3 substituents independently selected from J.

According to another embodiment of compounds of formula I, the

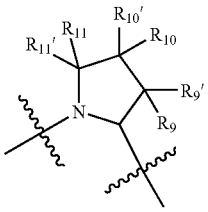

radical is:

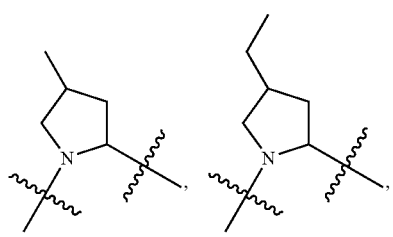

-continued

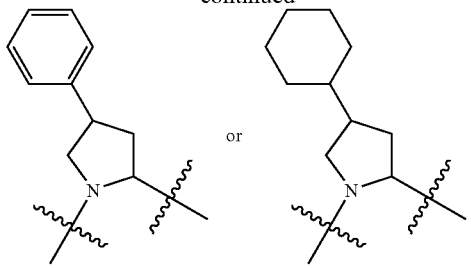

or

According to yet another embodiment of compounds of formula I, in the

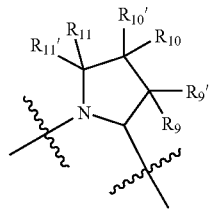

radical
$R_9$, $R_{9'}$, $R_{10}$, $R_{10'}$, and $R_{11}$ are H; and
$R_{11'}$ is:
(C1-C12)-aliphatic-,
(C3-C10)-cycloalkyl- or -cycloalkenyl-,
(C6-C10)-aryl-,
  wherein any ring is optionally fused to a (C6-C10)aryl, (C5-C10)heteroaryl, (C3-C10)cycloalkyl, or (C3-C10)heterocyclyl;
  wherein up to 3 aliphatic carbon atoms in $R_{11'}$ may be replaced by a heteroatom selected from O, NH, S, SO, or $SO_2$ in a chemically stable arrangement;
  wherein $R_{11'}$ is independently and optionally substituted with up to 3 substituents independently selected from J.

According to another embodiment of compounds of formula I, the

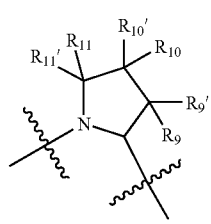

radical is:

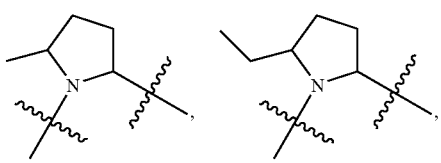

-continued

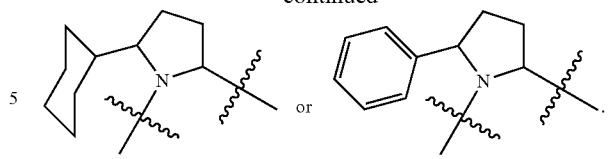

or

According to another embodiment of compounds of formula I, in the

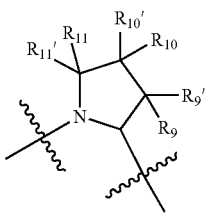

radical
$R_9$, $R_{10}$, $R_{11}$, and $R_{11'}$ are H; and
$R_{9'}$, and $R_{10'}$ are:
(C1-C12)-aliphatic-,
(C3-C10)-cycloalkyl- or -cycloalkenyl-,
  wherein up to 3 aliphatic carbon atoms in $R_{9'}$, and $R_{10'}$, may be replaced by a heteroatom selected from O, NH, S, SO, or $SO_2$ in a chemically stable arrangement;
  wherein $R_{9'}$, and $R_{10'}$ are independently and optionally substituted with up to 3 substituents independently selected from J.

According to another embodiment of compounds of formula I, the

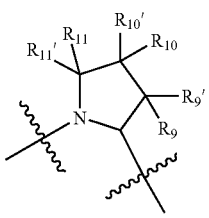

radical is:

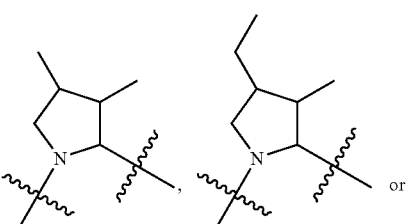

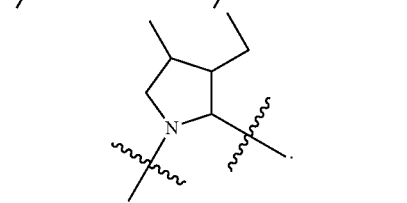

According to another embodiment of compounds of formula I, in the

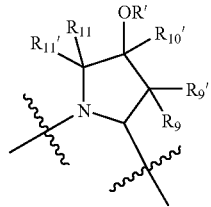

radical

R$_9$, R$_{9'}$, R$_{10'}$, R$_{11}$, and R$_{11'}$ are H; and

R' is selected from:

(C6-C10)-aryl-, (C6-C10)-aryl-(C1-C12)aliphatic-, (C3-C10)-heterocyclyl-, (C3-C10)-heterocyclyl-(C1-C12)aliphatic-, (C5-C10)-heteroaryl-, and (C5-C10)-heteroaryl-(C1-C12)-aliphatic-;

wherein up to 5 atoms in R' are optionally and independently substituted with J.

According to another embodiment of compounds of formula I, the

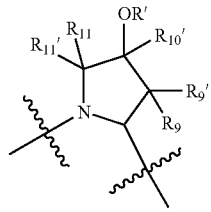

radical is:

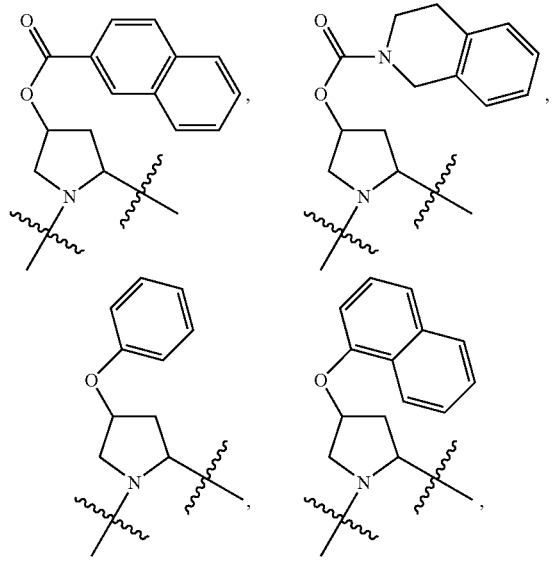

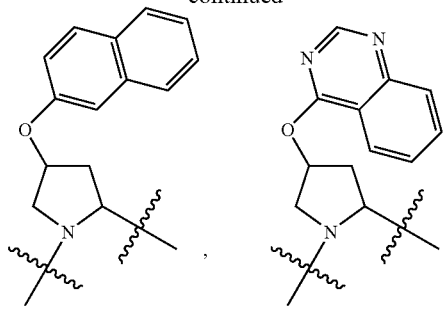

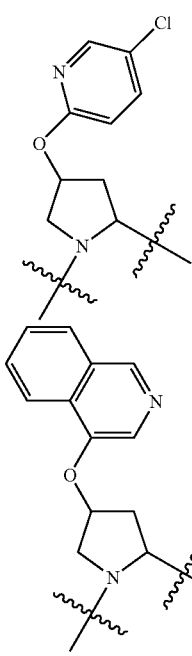

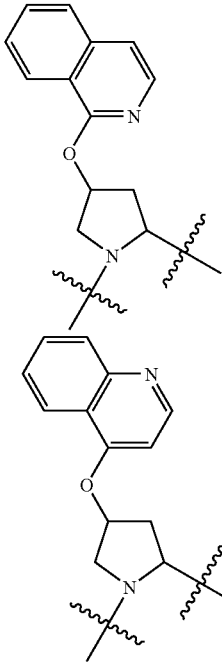

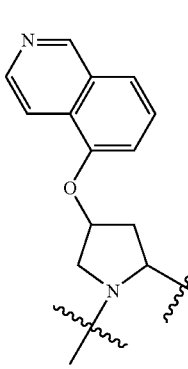

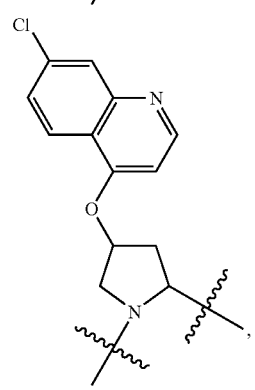

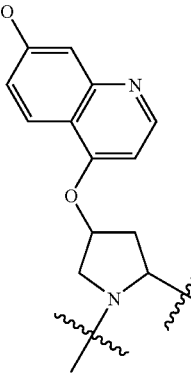

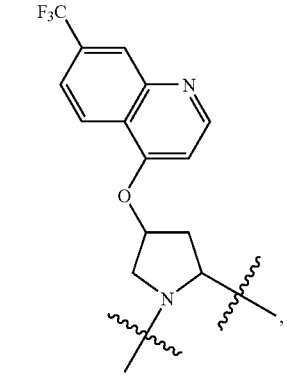

31
-continued
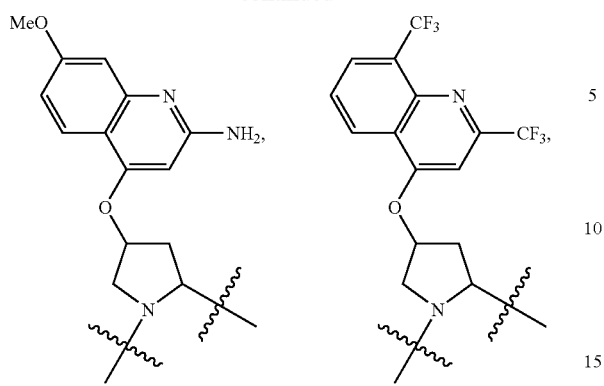
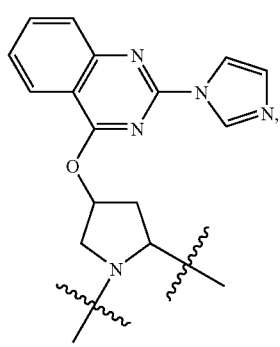
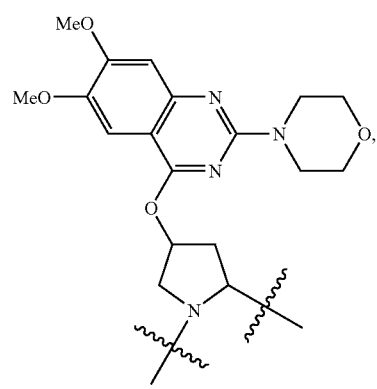
32
-continued
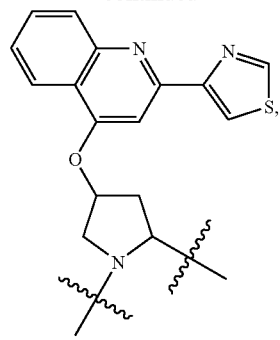
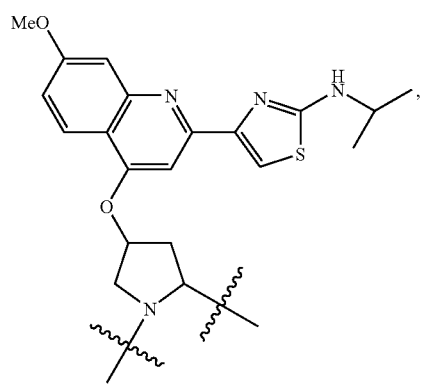
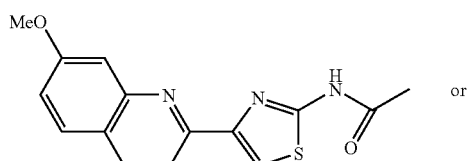
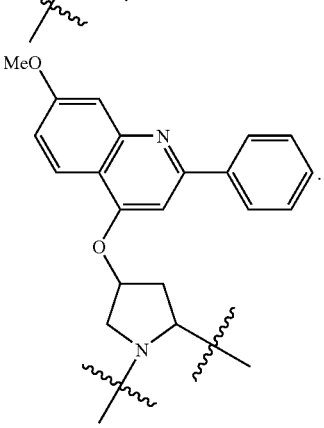
wherein up to 5 atoms in R' are optionally and independently substituted with J.

According to another embodiment of compounds of formula I, the

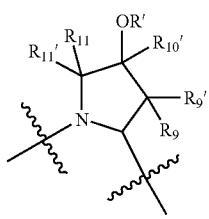

radical is:

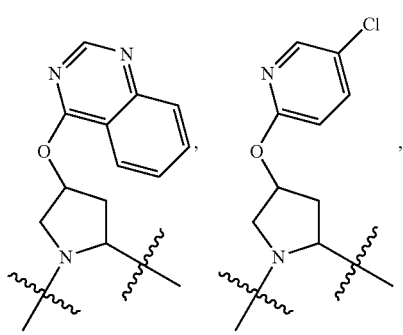

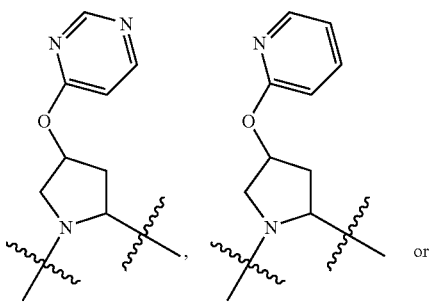

wherein up to 5 atoms in R' are optionally and independently substituted with J.

According to yet another embodiment of compounds of formula I, in the

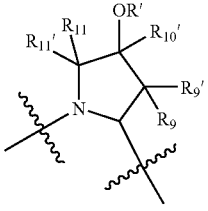

radical $R_9$, $R_{9'}$, $R_{10'}$, $R_{11}$, and $R_{11'}$ are H; and

R' is selected from:

(C6-C10)-aryl-(C1-C12)aliphatic-, (C3-C10)-heterocyclyl-(C1-C12)aliphatic-, and (C5-C10)-heteroaryl-(C1-C12)-aliphatic-;

wherein up to 5 atoms in R' are optionally and independently substituted with J.

According to a preferred embodiment of compounds of formula I, the

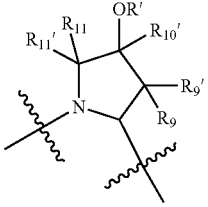

radical is:

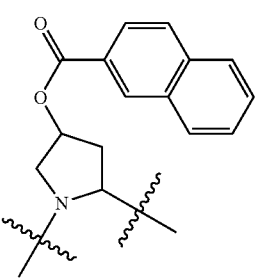 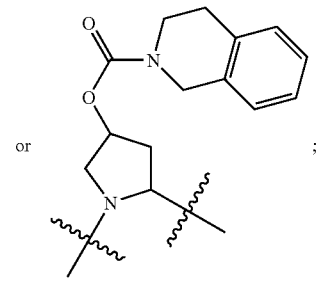

wherein up to 5 atoms in R' are optionally and independently substituted with J.

According to another embodiment, the present invention provides a compound of formula IL:

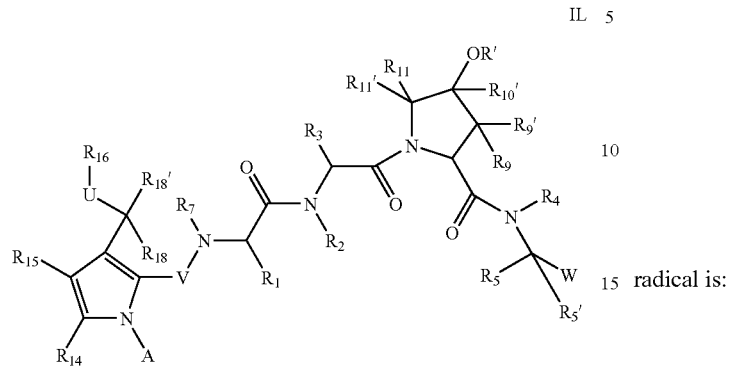

wherein:

R', $R_1$, $R_2$, $R_3$, $R_4$, $R_5$, $R_{5'}$, $R_7$, $R_9$, $R_{9'}$, $R_{11}$, $R_{11'}$, $R_{14}$, $R_{15}$, $R_{16}$, $R_{18}$, $R_{18'}$, V, A, U, and W are as defined in any of the embodiments herein.

According to another embodiment of compounds of formula I, the

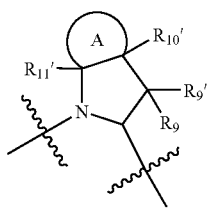

radical is:

wherein;

ring A is a 5- to 6-membered aromatic or a 3- to 7-membered non-aromatic ring system having up to 3 heteroatoms independently selected from N, NH, O, SO, or $SO_2$;

wherein said ring A is optionally fused to a (C6-C10)aryl, (C5-C10)heteroaryl, (C3-C10)cycloalkyl, or (C3-C10)heterocyclyl;

wherein any ring has up to 3 substituents selected independently from J; and $R_9$, $R_{9'}$, $R_{10'}$, and $R_{11'}$ are as defined in any of the embodiments herein.

According to another embodiment of compounds of formula I, the radical is:

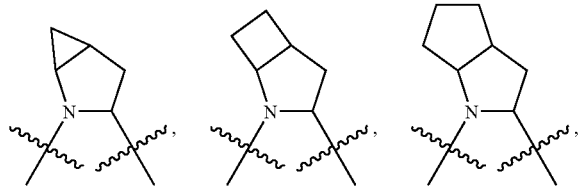

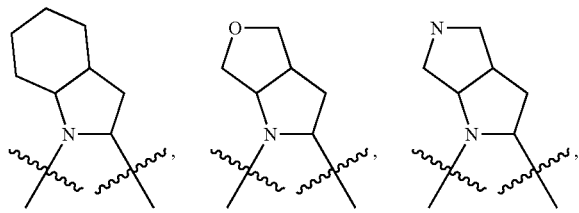

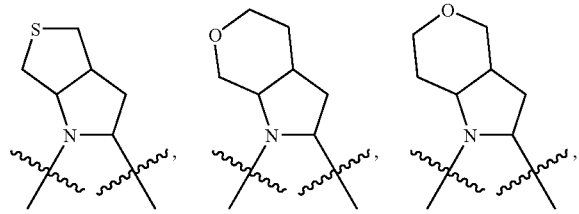

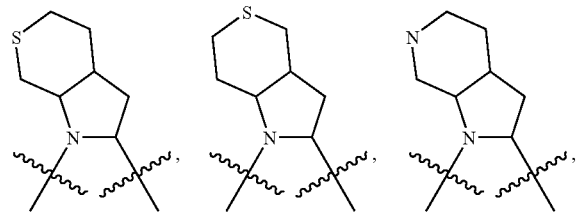

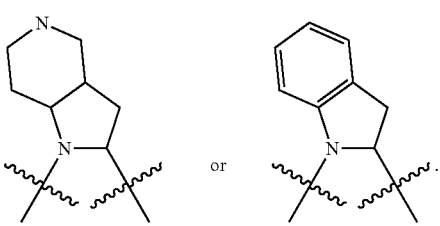

According to another embodiment of compounds of formula I, the

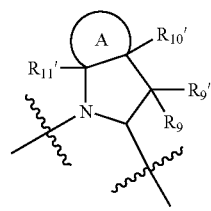

radical is:

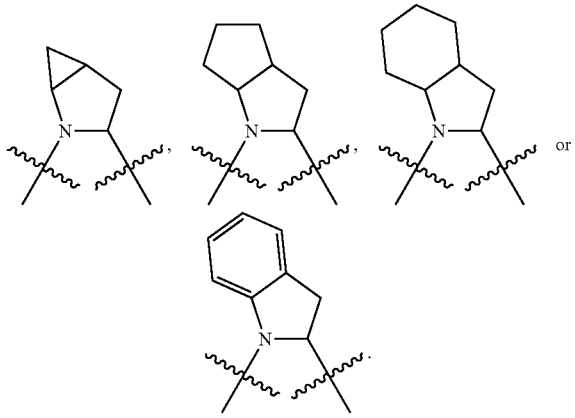

According to another embodiment of compounds of formula I, the

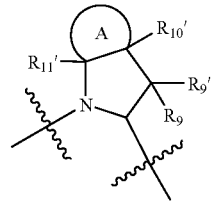

radical is:

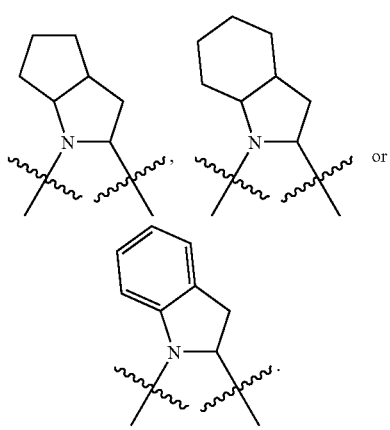

According to a preferred embodiment, the

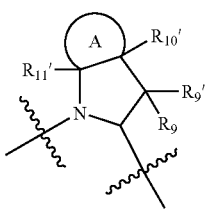

radical is:

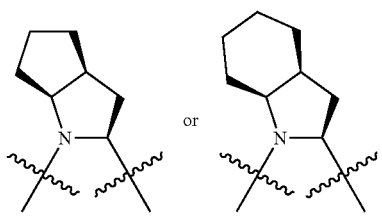

According to another embodiment, the present invention provides a compound of formula IM:

IM

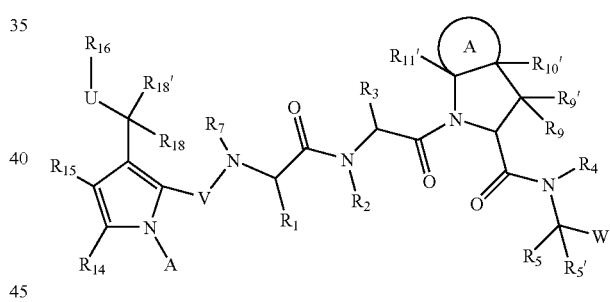

wherein:

$R_1$, $R_2$, $R_3$, $R_4$, $R_5$, $R_{5'}$, $R_7$, $R_9$, $R_{9'}$, $R_{10'}$, $R_{11'}$, $R_{14}$, $R_{15}$, $R_{16}$, $R_{18}$, $R_{18'}$, V, A, U, W, and ring A are as defined in any of the embodiments herein.

According to another embodiment of compounds of formula I, the

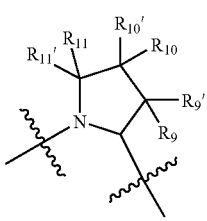

radical is:

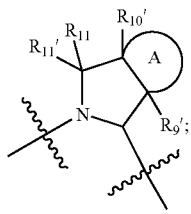

wherein;

ring A is a 5- to 6-membered aromatic or a 3- to 7-membered non-aromatic ring system having up to 3 heteroatoms independently selected from N, NH, O, SO, or $SO_2$;

wherein said ring A is optionally fused to a (C6-C10)aryl, (C5-C10)heteroaryl, (C3-C10)cycloalkyl, or (C3-C10)heterocyclyl;

wherein any ring has up to 3 substituents selected independently from J; and $R_{9'}$, $R_{10'}$, $R_{11}$, and $R_{11'}$ are as defined in any of the embodiments herein.

According to another embodiment of compounds of formula I, the

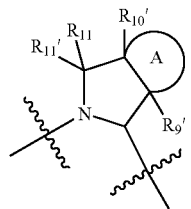

radical is:

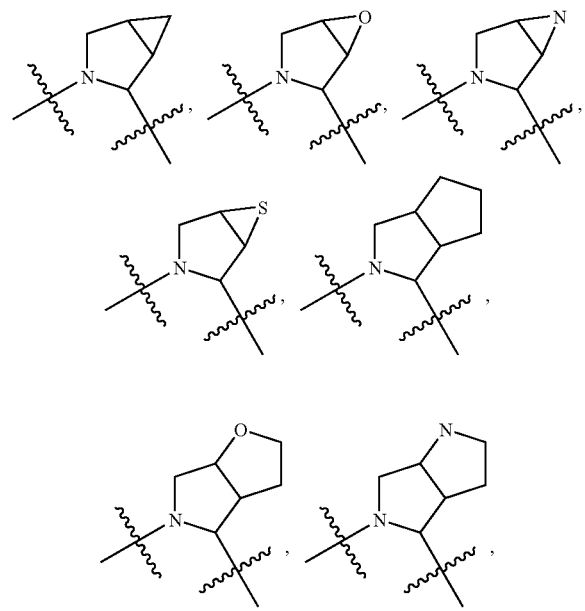

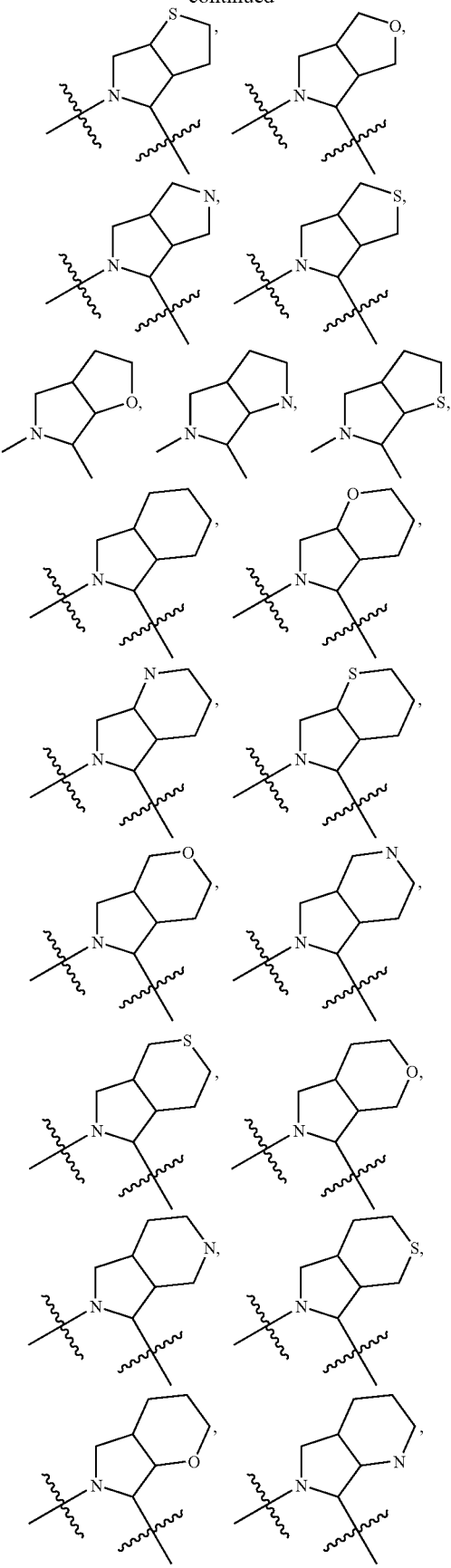

-continued

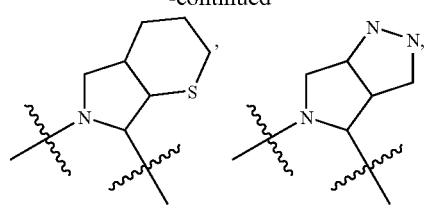
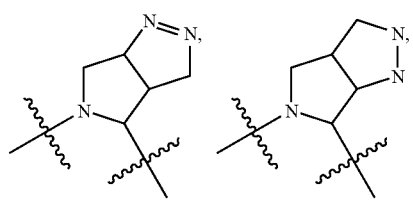
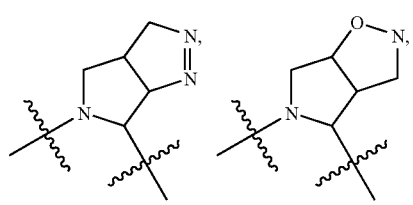
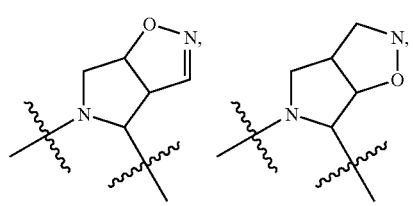
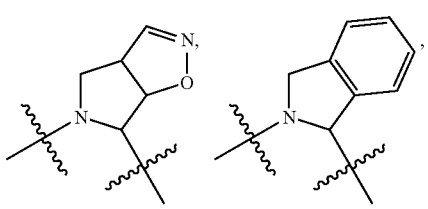
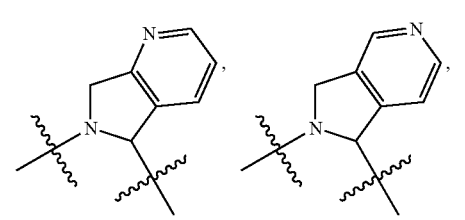
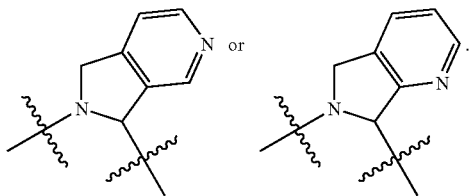

According to yet another embodiment of compounds of formula I, the

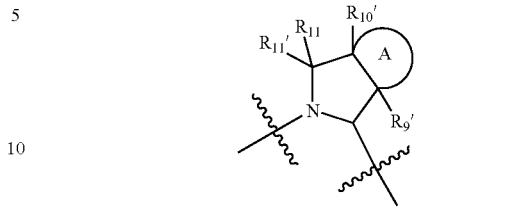

radical is:

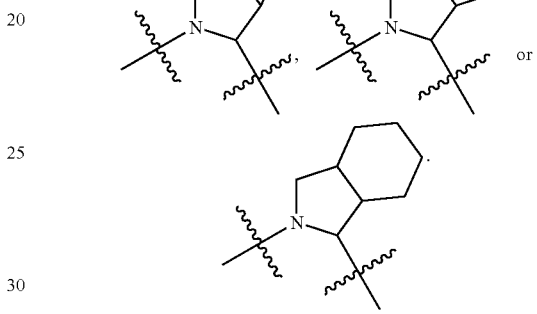

According to another embodiment, the present invention provides a compound of formula IN:

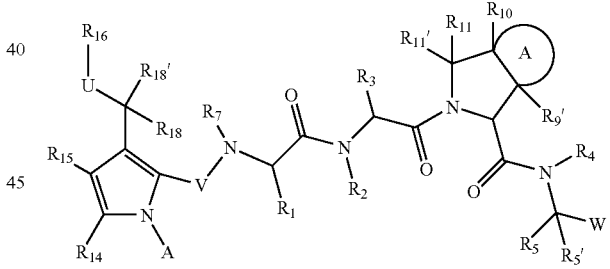

IN wherein:
$R_1$, $R_2$, $R_3$, $R_4$, $R_5$, $R_{5'}$, $R_7$, $R_9$, $R_{10'}$, $R_{11'}$, $R_{11}$, $R_{14}$, $R_{15}$, $R_{16}$, $R_{18}$, $R_{18'}$, V, A, U, W, and ring A are as defined in any of the embodiments herein.

According to another embodiment of compounds of formula I, the

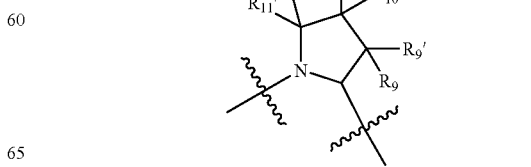

radical is:

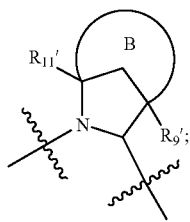

wherein:
ring B forms a 3- to a 20-membered carbocyclic or heterocyclic ring system;
wherein each ring B is either aromatic or nonaromatic;
wherein each heteroatom in the heterocyclic ring system is N, NH, O, SO, or $SO_2$;
wherein ring B is optionally fused to a (C6-C10)aryl, (C5-C10)heteroaryl, (C3-C10)cycloalkyl, or (C3-C10)heterocyclyl;
wherein each ring has up to 3 substituents selected independently from J; and
$R_9'$ and $R_{11'}$ are as defined in any of the embodiments herein.
According to another embodiment, the

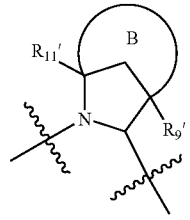

radical is:

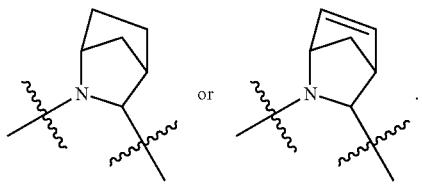

According to yet another embodiment, the present invention provides a compound of formula IO:

IO

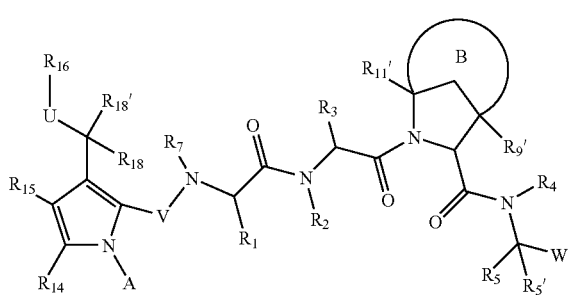

wherein:
$R_1$, $R_2$, $R_3$, $R_4$, $R_5$, $R_{5'}$, $R_7$, $R_{9'}$, $R_{11'}$, $R_{14}$, $R_{15}$, $R_{16}$, $R_{18}$, $R_{18'}$, V, A, U, W, and ring B are as defined in any of the embodiments herein.

According to another embodiment, W in compounds of formula I is:

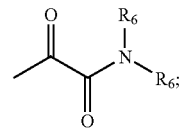

wherein in the W, the $NR_6R_6$ is selected from —NH—(C1-C6 aliphatic), —NH— (C3-C6 cycloalkyl), —NH—CH($CH_3$)-aryl, or —NH—CH($CH_3$)-heteroaryl, wherein said aryl or said heteroaryl is optionally substituted with up to 3 halogens.

According to another embodiment in compounds of formula I, the $NR_6R_6$ in the W radical is:

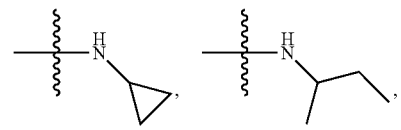

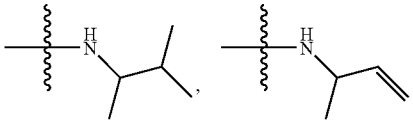

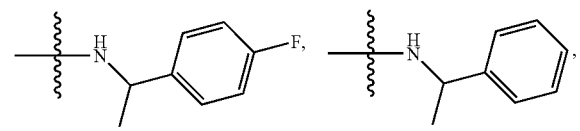

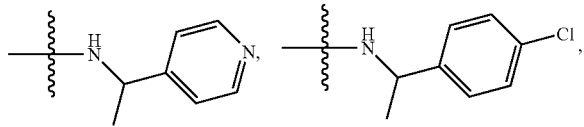

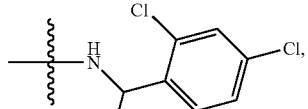

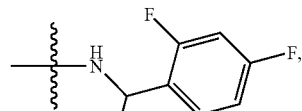

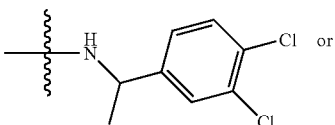

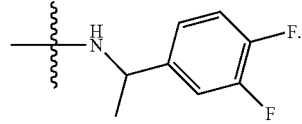

According to another embodiment in compounds of formula I, the $NR_6R_6$ in the W radical is:
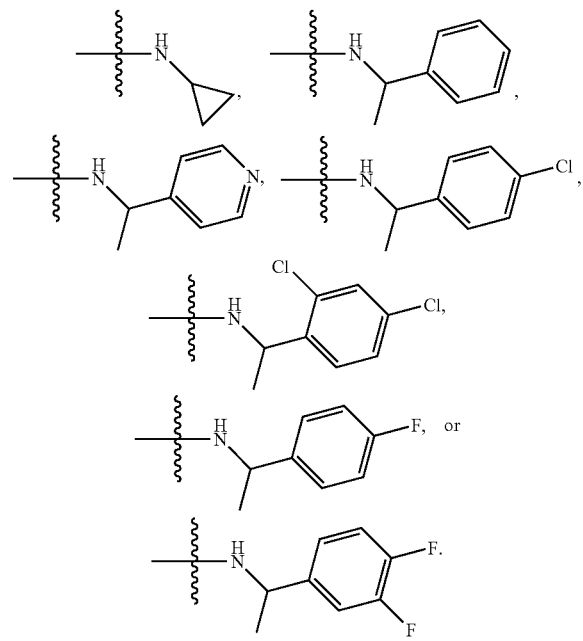
More preferably, in the W, the $NR_6R_6$ is:
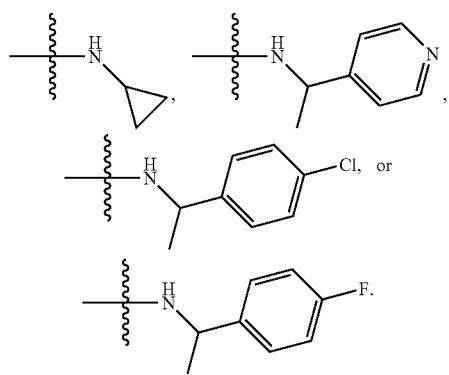
Even more preferably, in the W, the $NR_6R_6$ is:
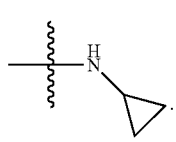
According to another embodiment in compounds of formula I, the $NR_6R_6$ in the W radical is:
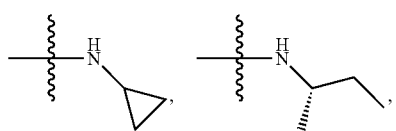
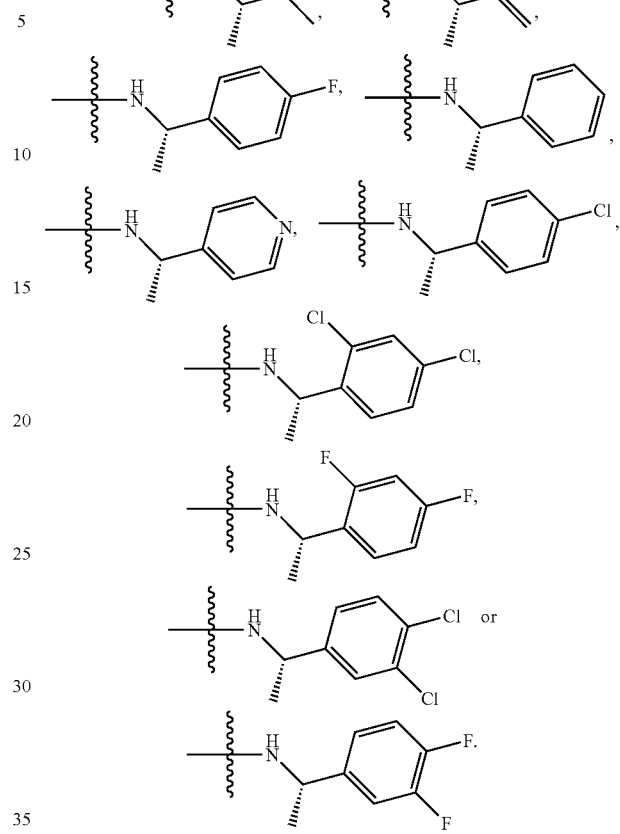
According to another embodiment in compounds of formula I, the $NR_6R_6$ in the W radical is:
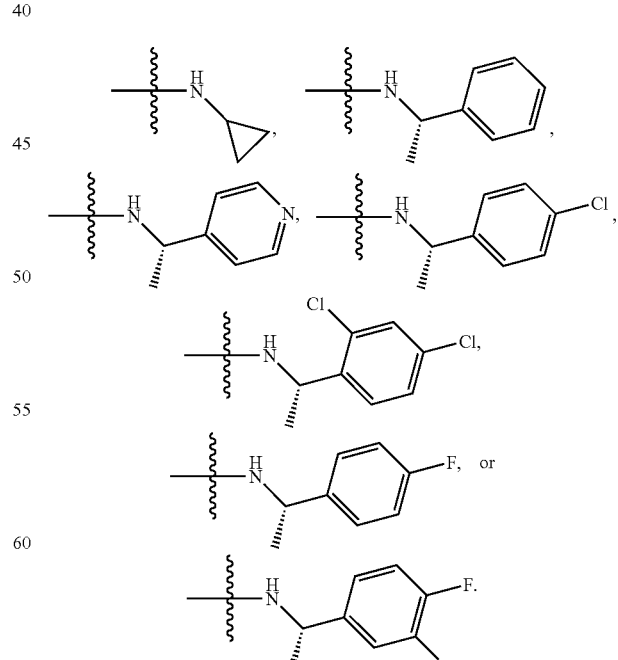

In yet another embodiment, in the W, the NR$_6$R$_6$ is:

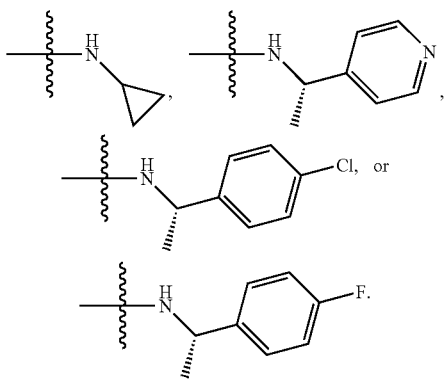

According to another embodiment, the present invention provides a compound of formula IP:

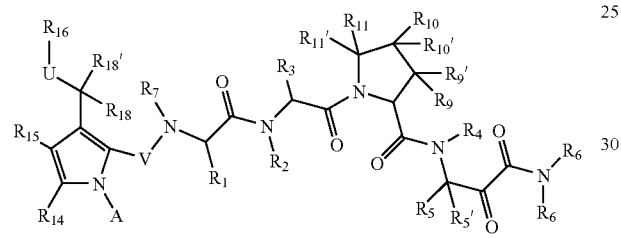

wherein:

R$_1$, R$_2$, R$_3$, R$_4$, R$_5$, R$_{5'}$, R$_6$, R$_7$, R$_9$, R$_{9'}$, R$_{10}$, R$_{10'}$, R$_{11}$, R$_{11'}$, R$_{14}$, R$_{15}$, R$_{16}$, R$_{18}$, R$_{18'}$, V, A, and U are as defined in any of the embodiments herein.

According to another embodiment W in compounds of formula I is:

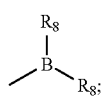

wherein R$_8$ is as defined above.

According to another embodiment for W in compounds of formula I, each R$_8$ together with the boron atom, is a (C5-C10)-membered heterocyclic ring having no additional heteroatoms other than the boron and the two oxygen atoms. Preferred groups are selected from:

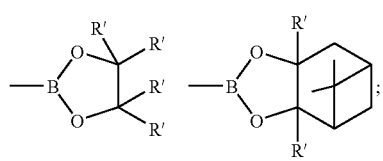

wherein R' is, preferably, (C1-C6)-aliphatic and is, more preferably, methyl.

According to another embodiment in compounds of formula I, R$_{5'}$ is hydrogen and R$_5$ is:

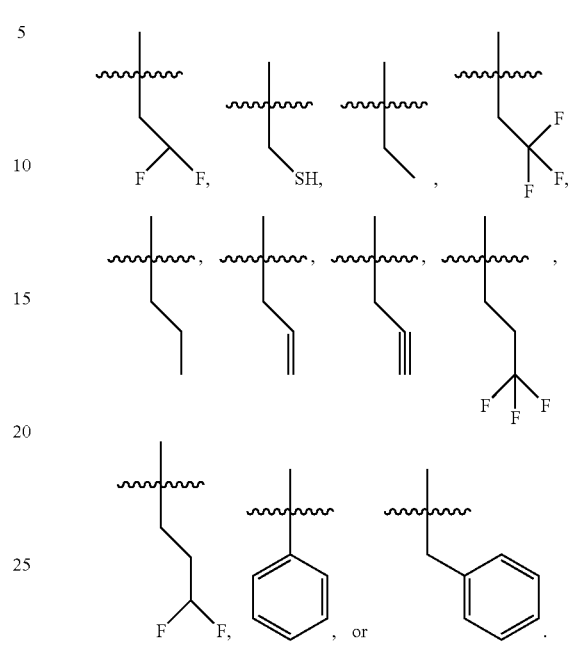

According to a preferred embodiment in compounds of formula I, R$_{5'}$ is hydrogen and R$_5$ is:

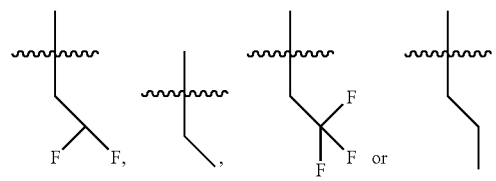

According to another embodiment, the present invention provides a compound of formula IQ:

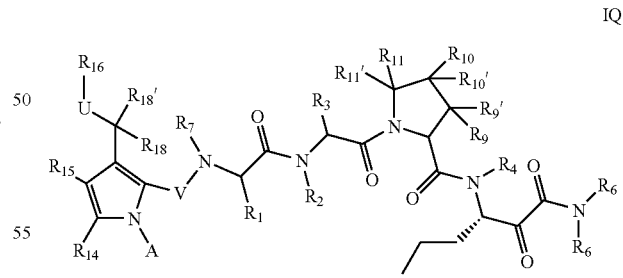

wherein:

R$_1$, R$_2$, R$_3$, R$_4$, R$_6$, R$_7$, R$_9$, R$_{9'}$, R$_{10}$, R$_{10'}$, R$_{11}$, R$_{11'}$, R$_{14}$, R$_{15}$, R$_{16}$, R$_{18}$, R$_{18'}$, V, A, and U are as defined in any of the embodiments herein.

According to a preferred embodiment for compounds of formula IQ, R$_1$, R$_2$, R$_3$, R$_4$, R$_7$, R$_9$, R$_{9'}$, R$_{10}$, R$_{10'}$, R$_{11}$, R$_{11'}$, R$_{14}$, R$_{15}$, R$_{16}$, R$_{18}$, R$_{18'}$, V, A, and U are as defined in any of the embodiments herein, and NR$_6$R$_6$ is:

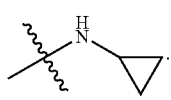

According to another embodiment in compounds of formula I, $R_{5'}$ and $R_5$ is:

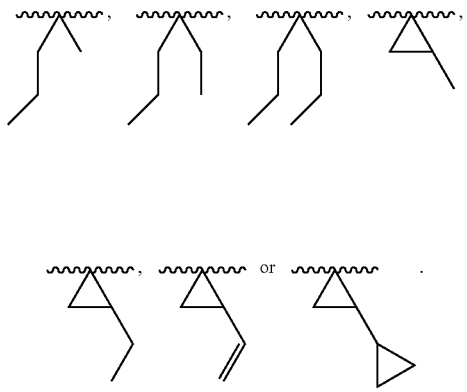

According to another embodiment for compounds of formula I, $R_2$, $R_4$, and $R_7$ are each independently H, methyl, ethyl, or propyl.

According to a preferred embodiment $R_2$, $R_4$, and $R_7$ are each H.

According to another embodiment, the present invention provides a compound of formula IR:

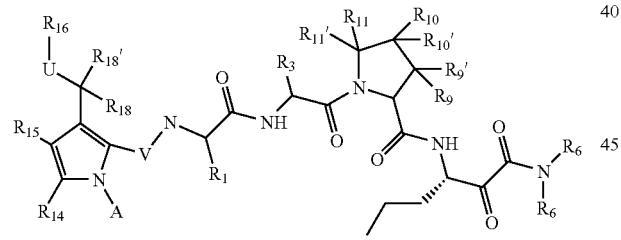

wherein:

$R_1$, $R_2$, $R_3$, $R_4$, $R_6$, $R_7$, $R_9$, $R_{9'}$, $R_{10}$, $R_{10'}$, $R_{11}$, $R_{11'}$, $R_{14}$, $R_{15}$, $R_{16}$, $R_{18}$, $R_{18'}$, V, A, and U are as defined in any of the embodiments herein.

According to a preferred embodiment for compounds of formula IR, $R_1$, $R_2$, $R_3$, $R_4$, $R_7$, $R_9$, $R_{9'}$, $R_{10}$, $R_{10'}$, $R_{11}$, $R_{11'}$, $R_{14}$, $R_{15}$, $R_{16}$, $R_{18}$, $R_{18'}$, V, A, and U are as defined in any of the embodiments herein, and $NR_6R_6$ is:

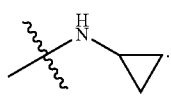

According to another embodiment in compounds of formula I, $R_3$ is:

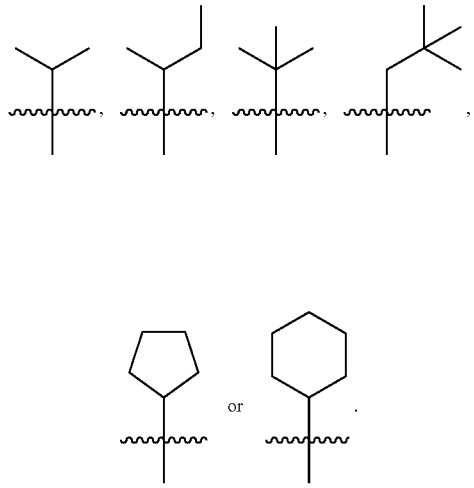

According to a preferred embodiment in compounds of formula I, $R_3$ is:

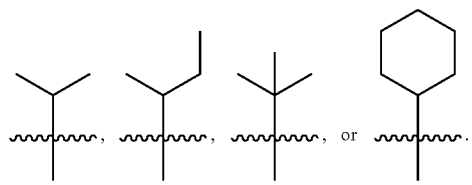

According to a more preferred embodiment in compounds of formula I, $R_3$ is:

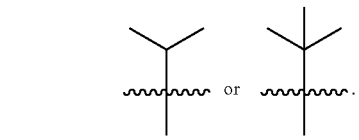

According to another embodiment, the present invention provides a compound of formula IS:

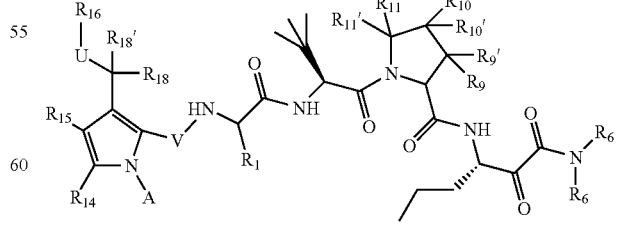

wherein:

$R_1$, $R_6$, $R_9$, $R_{9'}$, $R_{10}$, $R_{10'}$, $R_{11}$, $R_{11'}$, $R_{14}$, $R_{15}$, $R_{16}$, $R_{18}$, $R_{18'}$, V, A, and U are as defined in any of the embodiments herein.

According to another embodiment in compounds of formula I, $R_1$ is:

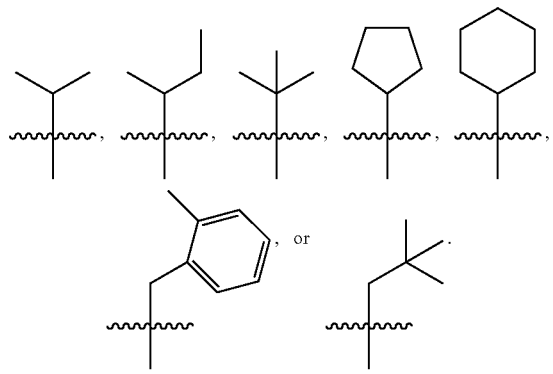

According to a preferred embodiment in compounds of formula I, $R_1$ is:

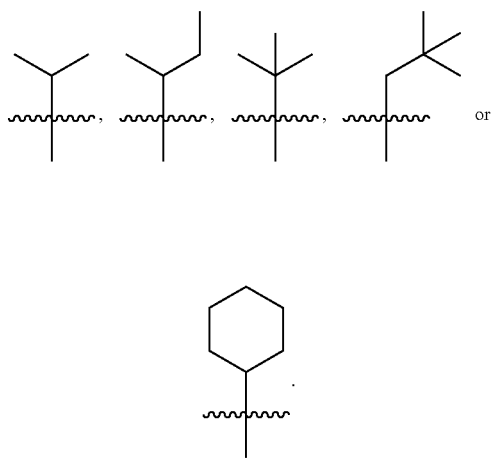

More preferably, $R_1$ is cyclohexyl.

According to another embodiment, the present invention provides a compound of formula IT:

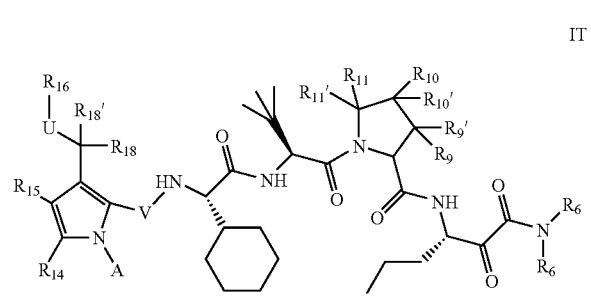

wherein:

$R_6$, $R_9$, $R_{9'}$, $R_{10}$, $R_{10'}$, $R_{11}$, $R_{11'}$, $R_{14}$, $R_{15}$, $R_{16}$, $R_{18}$, $R_{18'}$, V, A, and U are as defined in any of the embodiments herein.

According to another embodiment for compounds of formula IT, $R_6$, $R_9$, $R_{9'}$, $R_{10}$, $R_{10'}$, $R_{11}$, $R_{11'}$, and $R_{12}$ are as defined in any of the embodiments herein, and $NR_6R_6$ is:

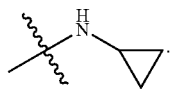

According to another embodiment for compounds of formulae I, and IA-IT, $R_{14}$ and $R_{15}$ are both —R' and R' is -(C1-C6 aliphatic). More preferably, $R_{14}$ and $R_{15}$ are both methyl.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Preferably, the compounds of this invention have the structure and stereochemistry depicted in formulae IA-IT.

Any of the preferred embodiments recited herein, including those embodiments in the above species, may define formula I individually or be combined to produce a preferred embodiment of this invention.

The compounds of this invention contain, and may be modified to contain, appropriate functionalities to enhance selective biological properties compared to the corresponding parent compound. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Without being bound by theory, we believe the compounds of this invention may enhance biological properties by behaving as prodrugs.

Chemical modifications of a drug into a bio- or chemically-reversible prodrug can confer temporary aqueous solubility to the drug substance that allows absorption following oral administration. See generally, Liu, S.; Han, C.; Wang, B. "Prodrug Derivatization as a Means to Enhance the Delivery of Peptide and Peptidomimetic Drugs" in *Frontiers of Biotechnology and Pharmaceuticals*, Ming Guo, ed, Science Press, New York, pp. 291-310 (2002) and Borchardt, R. T. and Wang, B. "Prodrug Strategies to Improve the Oral Absorption of Peptides and Peptide Mimetics" in *Controlled Drug Delivery. Designing Technologies for the Future*. Park. K. and Mrsny, R. J. Eds, American Chemical Society, Washington, D.C., pp. 36-45 (2000)

Prodrug strategies which rely on intramolecular cyclization to liberate a drug substance and a lactam derivative have been described where the liberated drugs are alcohols, phenols, and primary and secondary amines. For alcohols see, Saari et al., *J. Med. Chem.*, 33, pp. 2590-2595 (1990). For phenols see, Saari et al., *J. Med. Chem.*, 33, pp. 97-101 (1990). For amines see, Borchardt et al., Pharm. Sci., 86, pp. 757-767 (1997).

Any of the preferred embodiments recited herein, including those embodiments in the above species, may define formula (I) individually or be combined to produce a preferred embodiment of this invention.

Abbreviations which are used in the schemes, preparations and the examples that follow are:
THF: tetrahydrofuran
DMF: N,N,-dimethylformamide
EtOAc: ethyl acetate
AcOH: acetic acid
NMM: N-methylmorpholine NMP: N-methylpyyrolidinone
EtOH: ethanol
t-BuOH: tert-butanol
$Et_2O$: diethyl ether
DMSO: dimethyl sulfoxide
DCCA: dichloroacetic acid
DIEA: diisopropylethylamine
MeCN: acetonitrile
TFA: trifluoroacetic acid
DBU: 1,8-diazabicyclo[5.4.0]undec-7-ene
DEAD: diethyl azodicarboxylate
HOBt: 1-hydroxybenzotriazole hydrate
HOAt: 1-hydroxy-7-azabenzotriazole
EDC: 1-(3-dimethylaminopropyl)-3-ethylcarbodiimide hydrochloride
Boc: tert-butyloxycarbonyl
$Boc_2O$: di-tert-butyldicarbonate
Cbz: benzyloxycarbonyl
Cbz-Cl: benzyl chloroformate
Fmoc: 9-fluorenyl methyloxycarbonyl
SEM: silylethoxymethyl
TBAF: tetrabutylammonium fluoride
Chg: cyclohexylglycine
t-BG: tert-butylglycine
mCBPA: 3-chloroperoxybenzoic acid
DAST: (diethylamino)sulfur trifluoride
TEMPO: 2,2,6,6-tetramethyl-1-piperidinyloxy, free radical
PyBOP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
AIBN: 2,2'-azobisisobutyronitrile
rt or RT: room temperature
ON: overnight
ND: not determined
MS: mass spectrometry
LC: liquid chromatography General Synthetic Methodology:

The compounds of this invention may be prepared in general by methods known to those skilled in the art. Advantageously, these compounds are conveniently synthesized from readily available starting materials. Schemes 1-17 below illustrate synthetic routes to the compounds of the present invention.

As can be appreciated by the skilled artisan, the synthetic schemes shown are not intended to comprise a comprehensive list of all means by which the compounds described and claimed in this application may be synthesized. Other equivalent schemes, which will be readily apparent to the ordinary skilled organic chemist, may alternatively be used to synthesize various portions of the molecule as illustrated by the general schemes below. Additionally, the various synthetic steps described above may be performed in an alternate sequence or order to give the desired compounds. Other equivalent schemes, which will be readily apparent to the ordinary skilled organic chemist, may alternatively be used to synthesize various portions of the molecule as illustrated by the general schemes below, and the preparative examples that follow.

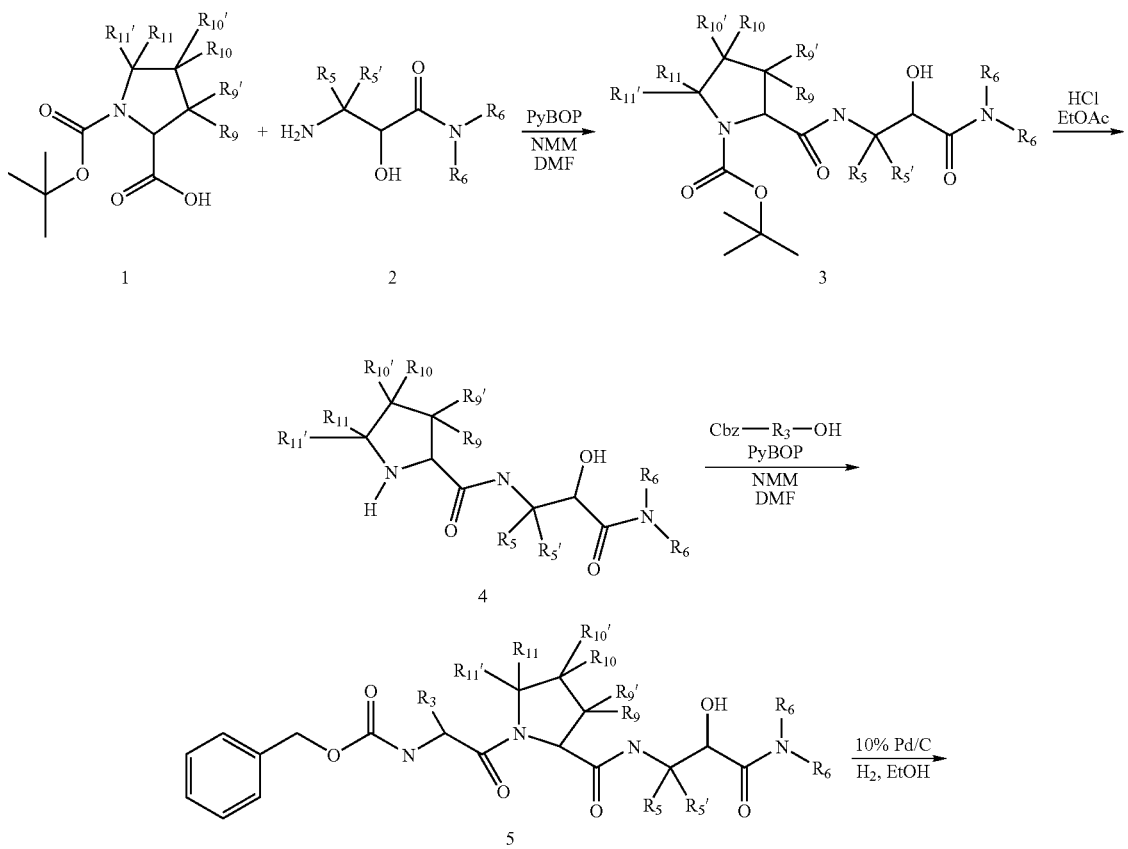

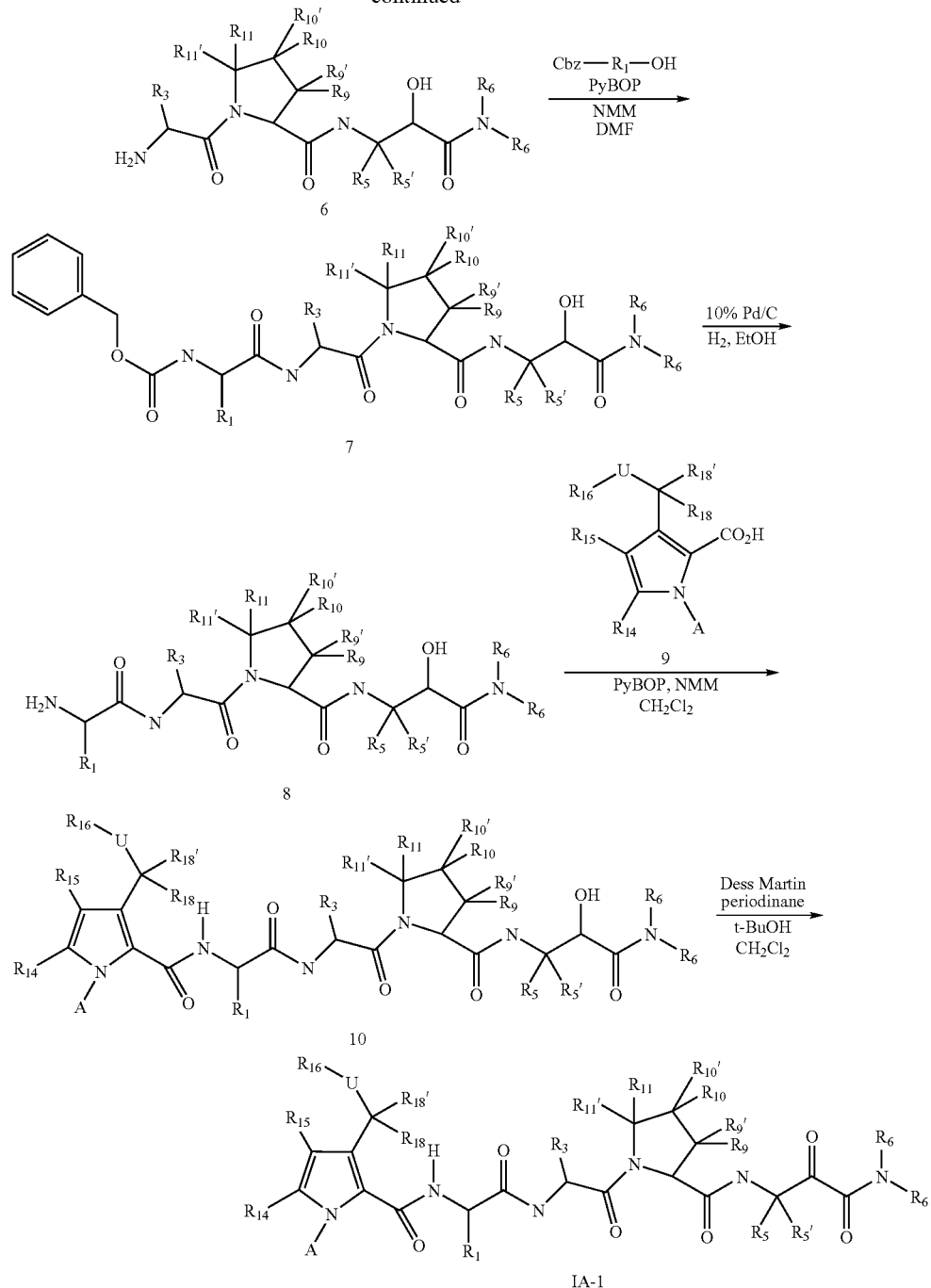

Scheme 1 above provides a general route for the preparation of compounds of formula I and IA-1, wherein V is —C(O), W is —C(O)C(O)—N(R$_6$)$_2$, R$_2$, R$_4$, and R$_7$ are H, and R$_1$, R$_3$, R$_5$, R$_5'$, R$_6$, R$_9$, R$_9'$, R$_{10}$R$_{10'}$, R$_{11}$, R$_{11'}$, R$_{12}$, R$_{12'}$, R$_{14}$, R$_{15}$, R$_{16}$, R$_{18}$, R$_{18'}$, A, and U are as described in any of the embodiments herein. As would be recognized by skilled practitioners, other suitable and commercially available coupling reagents may be used to prepare intermediates 3, 5, 7, and 10. Additionally, it will be recognized that the commercially available Cbz protected amino acids represented by, for instance, Cbz-R$_1$—OH, may alternatively be substituted with the commercial t-Boc protected amino acids. Suitable deprotection conditions to remove the Boc protecting groups are known to those skilled in the art. Likewise the oxidation of intermediate 10 to compounds of formula IA-1 may be accomplished using other suitable conditions known to the skilled artisan. Intermediate 2 may be prepared according to the procedures described by Schoellkopf, et al., *Justus Liebigs Ann. Chem.* GE, pp. 183-202 (1976) and Stemple et al., *Organic Letters,* 2(18), pp. 2769-2772 (2000). Intermediate pyrrole acid 9 may be prepared according to the methods described in the schemes below starting from commercially available starting materials.

Scheme 2:
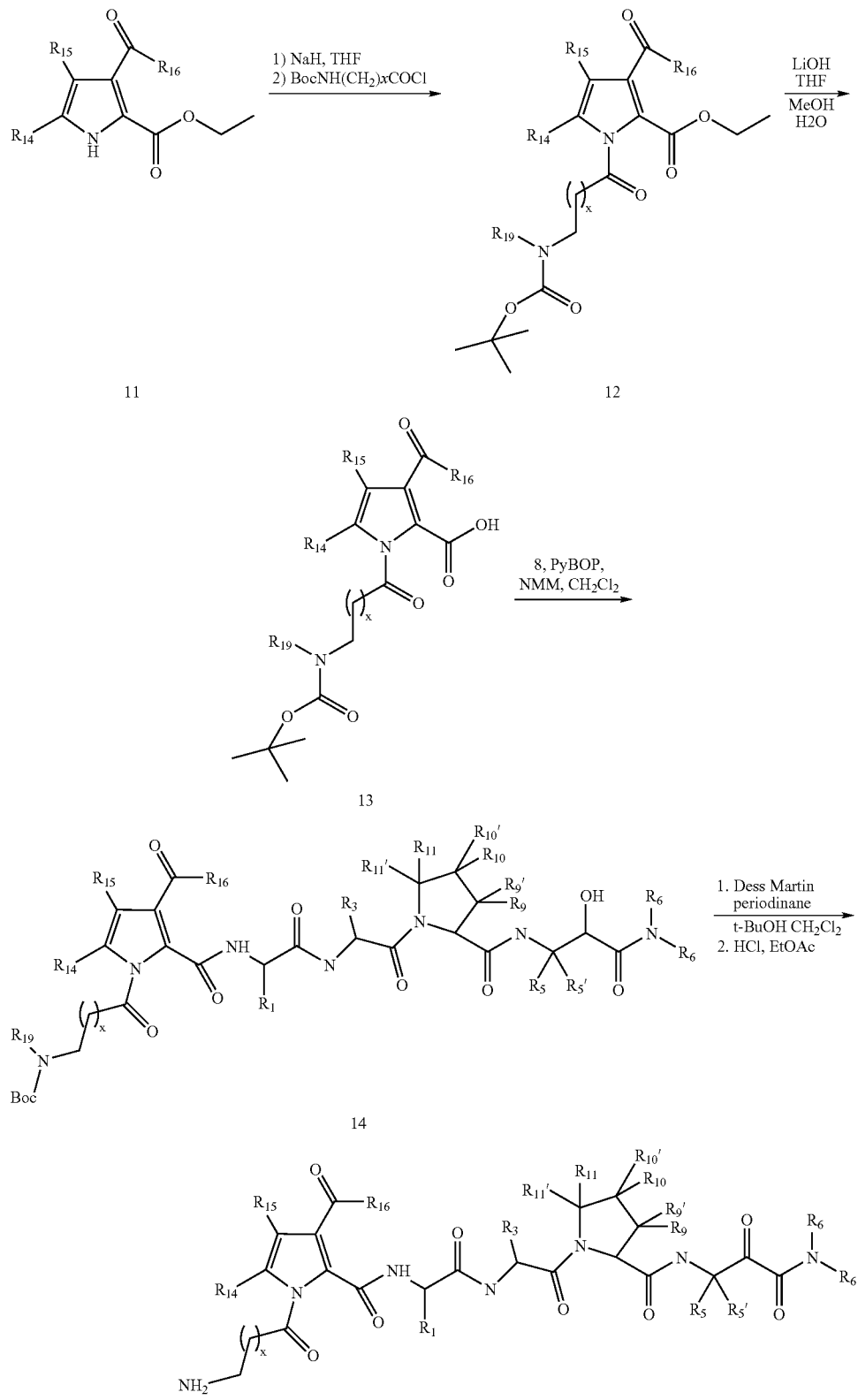

Scheme 2 above provides a general route for the preparation of compounds of formula I and IA-2 wherein V is —C(O), W is —C(O)C(O)—N(R$_6$)$_2$, R$_{18}$ is absent and R$_{18'}$ is =O, U is a bond, A is —C(R$_{12}$)(R$_{12'}$)-T-R$_{13}$ wherein R$_{12}$ is absent, R$_{12'}$ is =O, T is a bond and R$_{13}$ is R$_{19}$, R$_{19}$ is a (C1-C12)-aliphatic- with one carbon atom replaced by an NR$_{19}$ substituent, R$_{19}$ is hydrogen, x is preferably 2-4, R$_2$, R$_4$, and R$_7$ are H, and R$_1$, R$_3$, R$_5$, R$_{5'}$, R$_6$, R$_9$, R$_{9'}$, R$_{10}$, R$_{10'}$, R$_{11}$, R$_{11'}$, R$_{12}$, R$_{12'}$, R$_{14}$, R$_{15}$, and R$_{16}$ are as described in any of the embodiments herein. The preparation of compounds of formula I and IA-2, wherein R$_{13}$ is different than that depicted in scheme 2, may be accomplished in similar fashion by acylation of the pyrrole anion using other commercially available acid chlorides. As would be recognized by skilled practitioners, other suitable and commercially available coupling reagents may be used to prepare intermediate 14. Likewise the oxidation of intermediate 14 may be accomplished using other suitable conditions known to the skilled artisan.

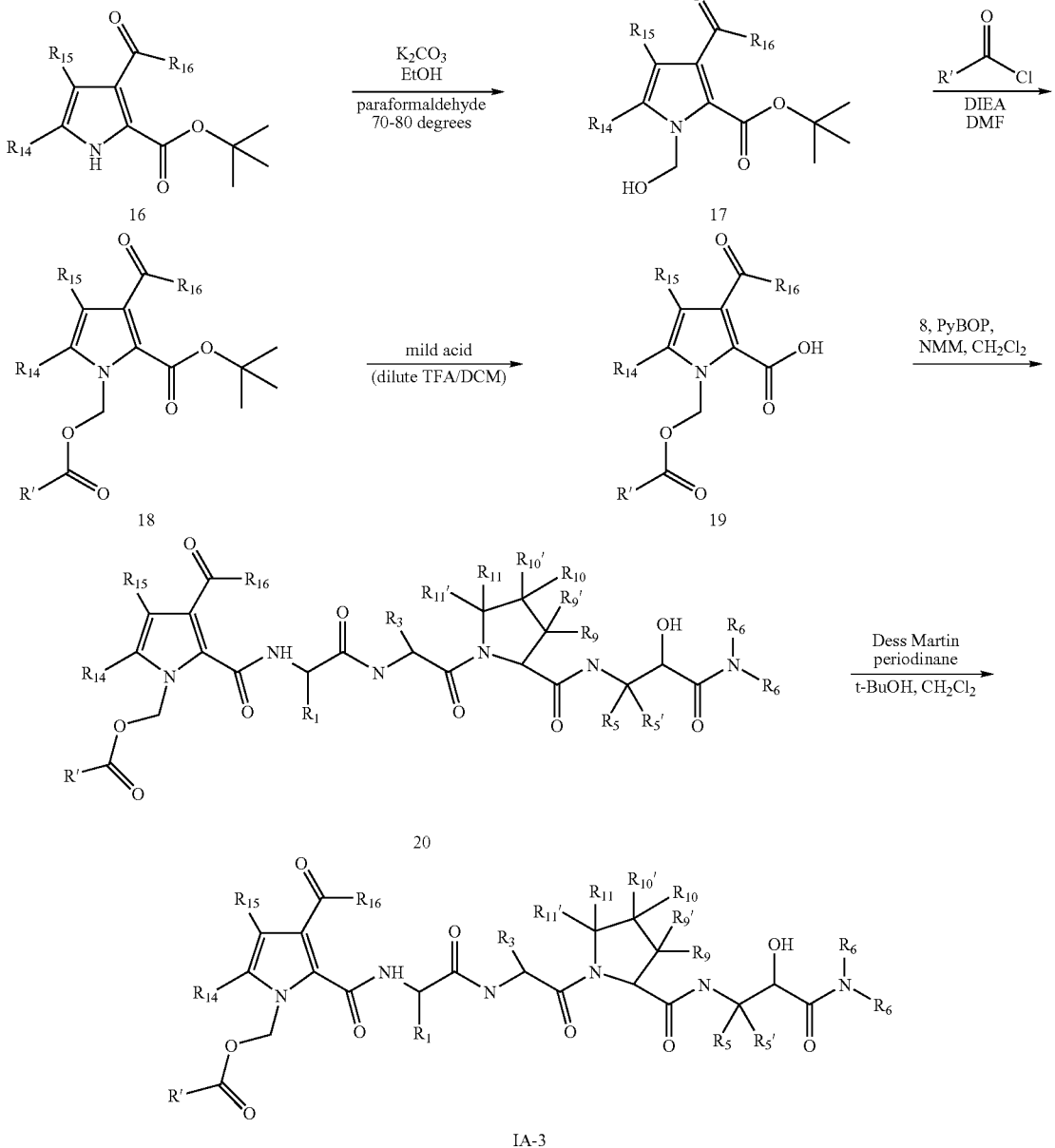

Scheme 3 above provides a general route for the preparation of compounds of formula I and IA-3 wherein V is —C(O), W is —C(O)C(O)—N(R$_6$)$_2$, R$_{18}$ is absent and R$_{18'}$ is =O, U is a bond, A is —C(R$_{12}$)(R$_{12'}$)-T-R$_{13}$ wherein R$_{12}$ is hydrogen, R$_{12'}$ is CH, T is oxygen and R$_{13}$ is —C(O)R', R$_2$, R$_4$, and R$_7$ are H, and R', R$_1$, R$_3$, R$_5$, R$_{5'}$, R$_6$, R$_9$, R$_{9'}$, R$_{10}$, R$_{10'}$, R$_{11}$, R$_{11'}$, R$_{12}$, R$_{12'}$, R$_{14}$, R$_{15}$, and R$_{16}$ are as described in any of the embodiments herein. Condensation of the pyrrole 16 with paraformaldehyde is accomplished according to the procedures listed in PCT publication WO 97/41132. The preparation of compounds of formula I and IA-2, wherein R$_{12}$ is hydrogen, R$_{12'}$ is (C2-C6)-aliphatic- may be accomplished in similar fashion by substituting the appropriate aldehyde for paraformaldehyde in the conversion of 16 to 17. As would be recognized by skilled practitioners, other suitable and commercially available coupling reagents may be used to prepare intermediate 20. Likewise the oxidation of intermediate 20 may be accomplished using other suitable conditions known to the skilled artisan.
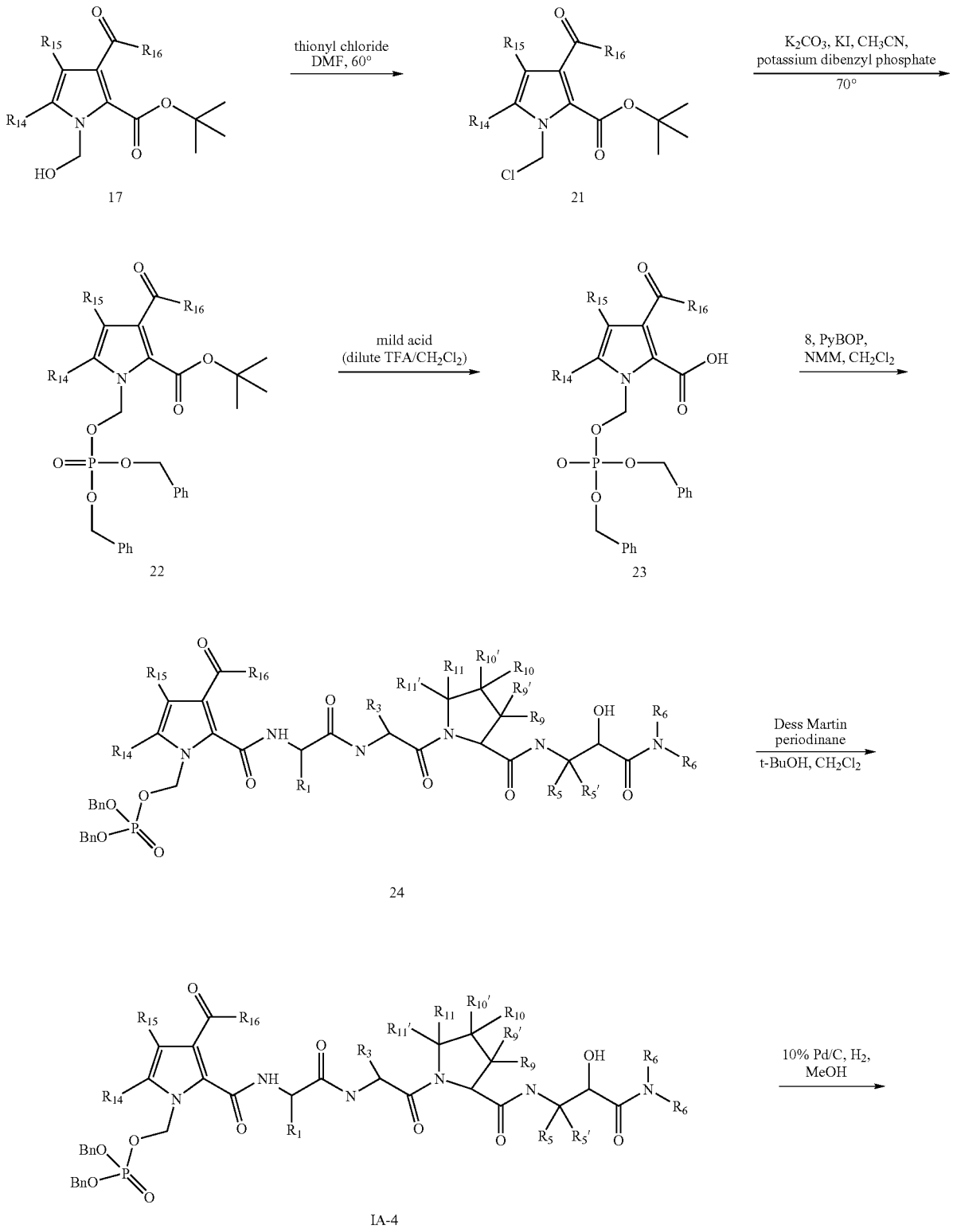

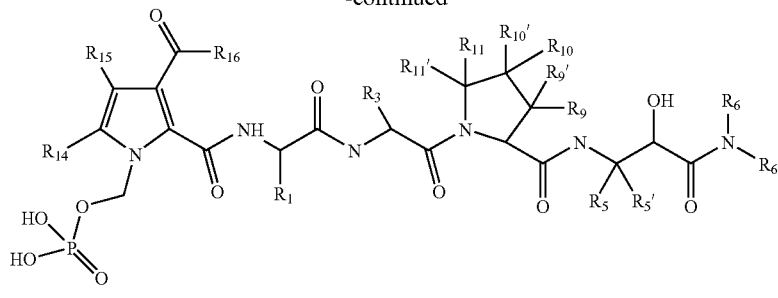

IA-5

Scheme 4 above provides a general route for the preparation of compounds of formula I and IA-4 and IA-5 wherein V is —C(O), W is —C(O)C(O)—N(R$_6$)$_2$, R$_{18}$ is absent and R$_{18'}$ is =O, U is a bond, A is —C(R$_{12}$)(R$_{12'}$)-T-R$_{13}$ wherein R$_{12}$ is hydrogen, R$_{12'}$ is CH, T is oxygen and R$_{13}$ is —P(O)(OR')$_2$, R' is benzyl (IA-4) or hydrogen (IA-5), R$_2$, R$_4$, and R$_7$ are H, and R', R$_1$, R$_3$, R$_5$, R$_{5'}$, R$_6$, R$_9$, R$_{9'}$, R$_{10}$, R$_{10'}$, R$_{11}$, R$_{11'}$, R$_{12}$, R$_{12'}$, R$_{14}$, R$_{15}$, and R$_{16}$ are as described in any of the embodiments herein. Pyrrole alcohol 17 (prepared by methods described above in scheme 3) is converted to chloride 18 with thionyl chloride followed by displacement with potassium dibenzyl phosphate to give phosphate ester 22 all according to the procedures listed in PCT publication WO 97/41132. Mild acid hydrolysis of the t-butyl ester followed by the coupling conditions and oxidation described in scheme 3 above gives compound IA-4. Hydrogenolysis of dibenzyl ester IA-4 using standard palladium catalysis gives free phosphonooxy acid IA-5. The preparation of compounds of formula IA-4, wherein R' is other than benzyl may be accomplished in similar fashion by using the appropriate phosphate reagent for the conversion of 21 to 22. As would be recognized by skilled practitioners, other suitable and commercially available coupling reagents may be used to prepare intermediate 24. Likewise the oxidation of intermediate 24 and the hydrogenolysis of IA-4 may be accomplished using other suitable conditions known to the skilled artisan.

Scheme 5:

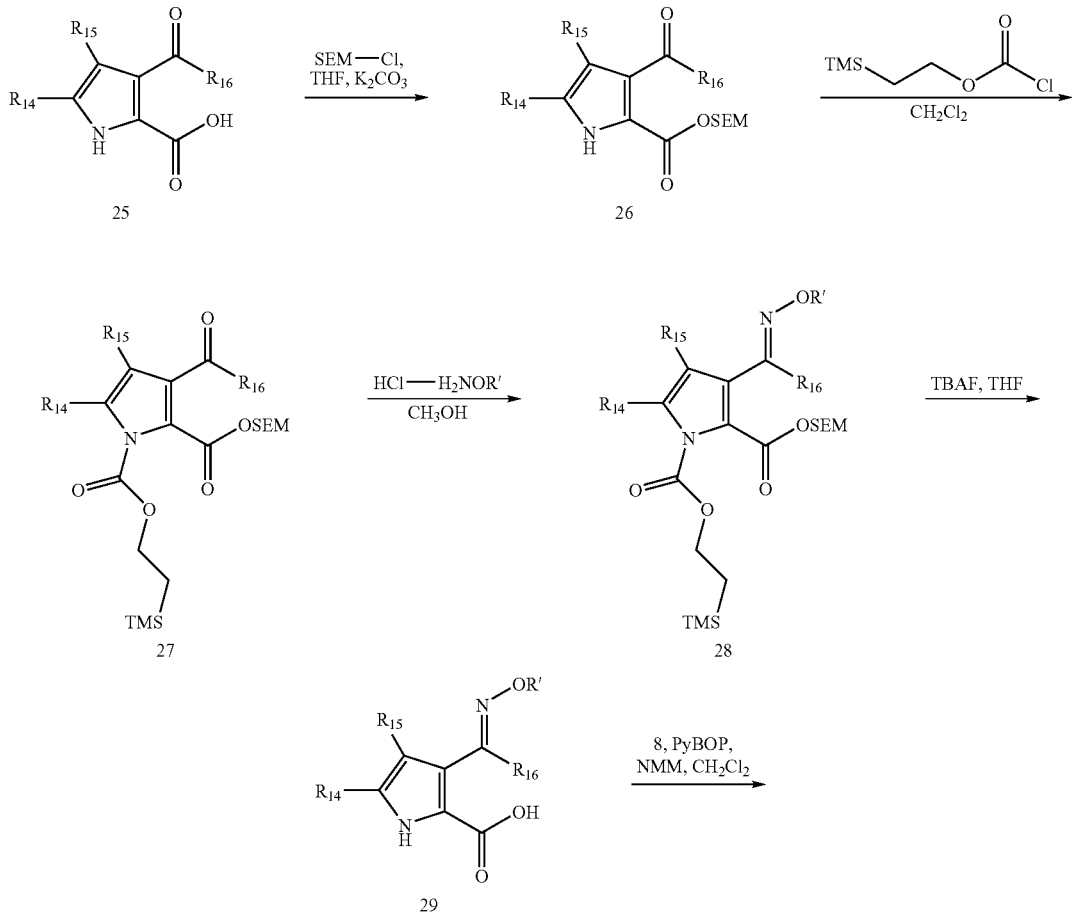

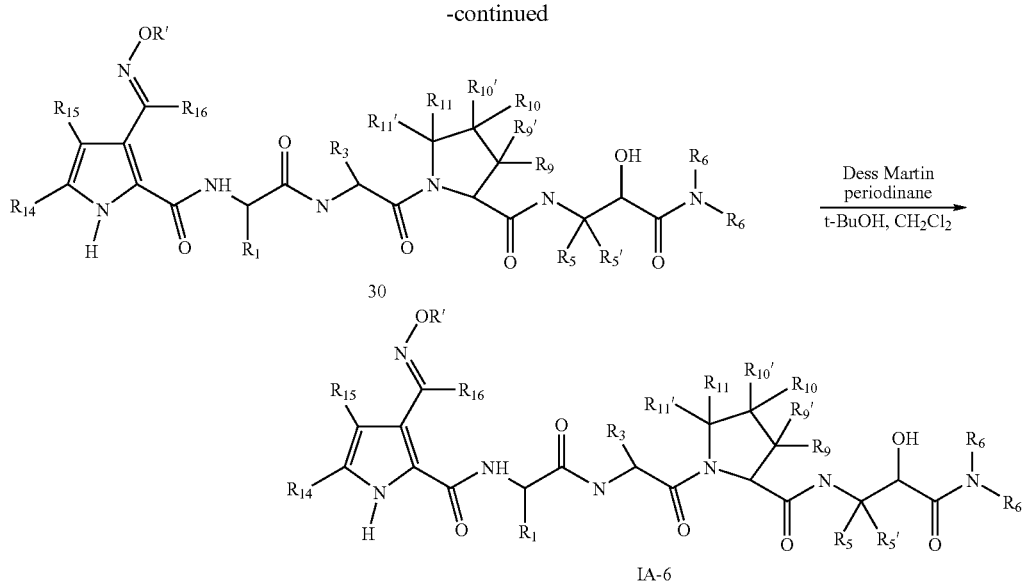

Scheme 5 above provides a general route for the preparation of compounds of formula I and IA-6 wherein V is —C(O), W is —C(O)C(O)—N($R_6$)$_2$, $R_{18}$ is absent and $R_{18'}$ is =N(OR'), U is a bond, $R_{16}$ is R', A is hydrogen, $R_2$, $R_4$, and $R_7$ are H, R', $R_1$, $R_3$, $R_5$, $R_{5'}$, $R_6$, $R_9$, $R_{9'}$, $R_{10}$, $R_{10'}$, $R_{11}$, $R_{11'}$, $R_{12}$, $R_{12'}$, $R_{14}$, and $R_{15}$, are as described in any of the embodiments herein. Pyrrole acid 25 (prepared by methods described above in scheme 3 and below in scheme 6) is esterfied to give SEM ester 26. Protection of the pyrrole nitrogen according to the procedure in J. Chem. Soc. Perkin Trans. 1, pp. 2181-2186 (1986) provides intermediate 27. Condensation with hydroxylamine (or alkylhydroxyl amine wherein $R_{18}$ is absent and $R_{18'}$ is =N(OR')), accomplished according to the procedure in J. Org. Chem., pp. 5917-5921 (1992), gives oxime 28. TBAF deprotection of both silyl based protecting groups according to the procedure described in J. Chem. Soc. Perkin Trans. (1), pp. 2181-2186 (1986), gives pyrrole oxime acid 29. Final coupling and oxidation are accomplished according to the procedures listed above in schemes 1, 3, and 5. As would be recognized by skilled practitioners, other suitable and commercially available coupling reagents may be used to prepare intermediate 30. Likewise the oxidation of intermediate 30 to IA-6 may be accomplished using other suitable conditions known to the skilled artisan.

Scheme 6:

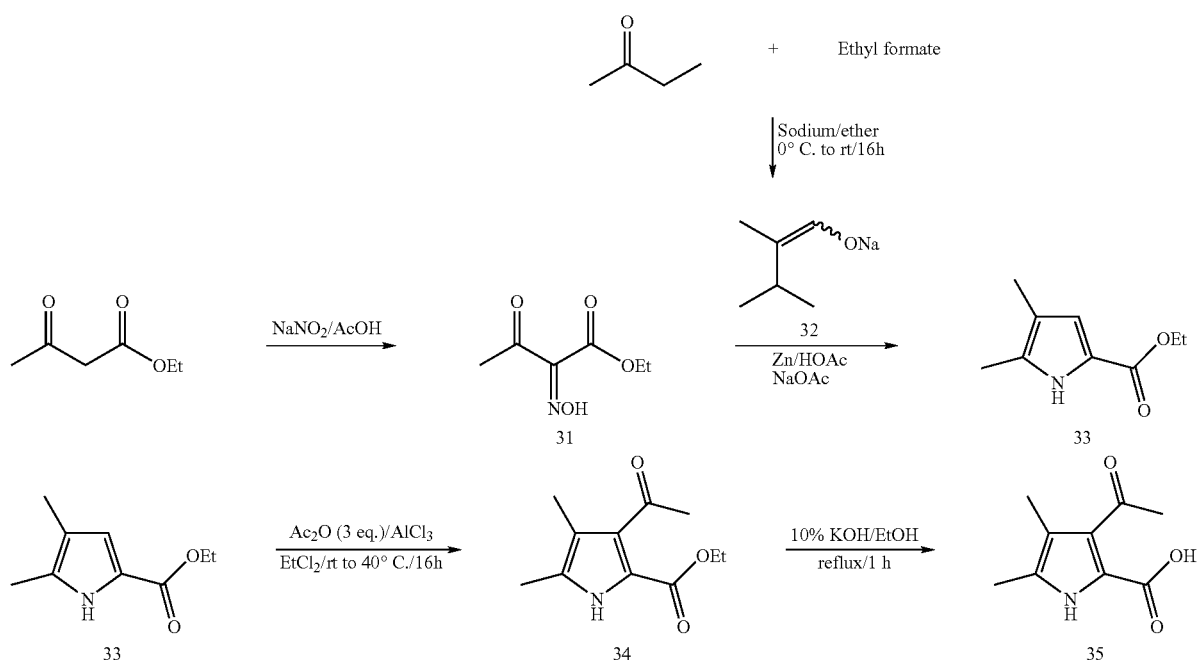

Scheme 6 above provides a general route for the preparation of starting pyrrole acid 35, wherein $R_{14}$ and $R_{15}$ are methyl, A is H, $R_{18}$ is absent, $R_{18'}$ is =O, U is a bond and $R_{16}$ is methyl. It will be appreciated by those skilled in the art that other pyrrole analogs of interest may be synthesized by modifications of scheme 6.

Scheme 7 above provides a general route for the preparation of compounds of formula I and IA-7 wherein V is —C(O), W is —C(O)C(O)—N($R_6$)$_2$, $R_{18}$ is absent and $R_{18'}$ is =N(R'), U is a bond, $R_{16}$ is R', A is hydrogen, $R_2$, $R_4$, and $R_7$ are H, R', $R_1$, $R_3$, $R_5$, $R_{5'}$, $R_6$, $R_9$, $R_{9'}$, $R_{10}$, $R_{10'}$, $R_{11}$, $R_{11'}$, $R_{12}$, $R_{12'}$, $R_{14}$, and $R_{15}$, are as described in any of the embodiments Scheme 7:

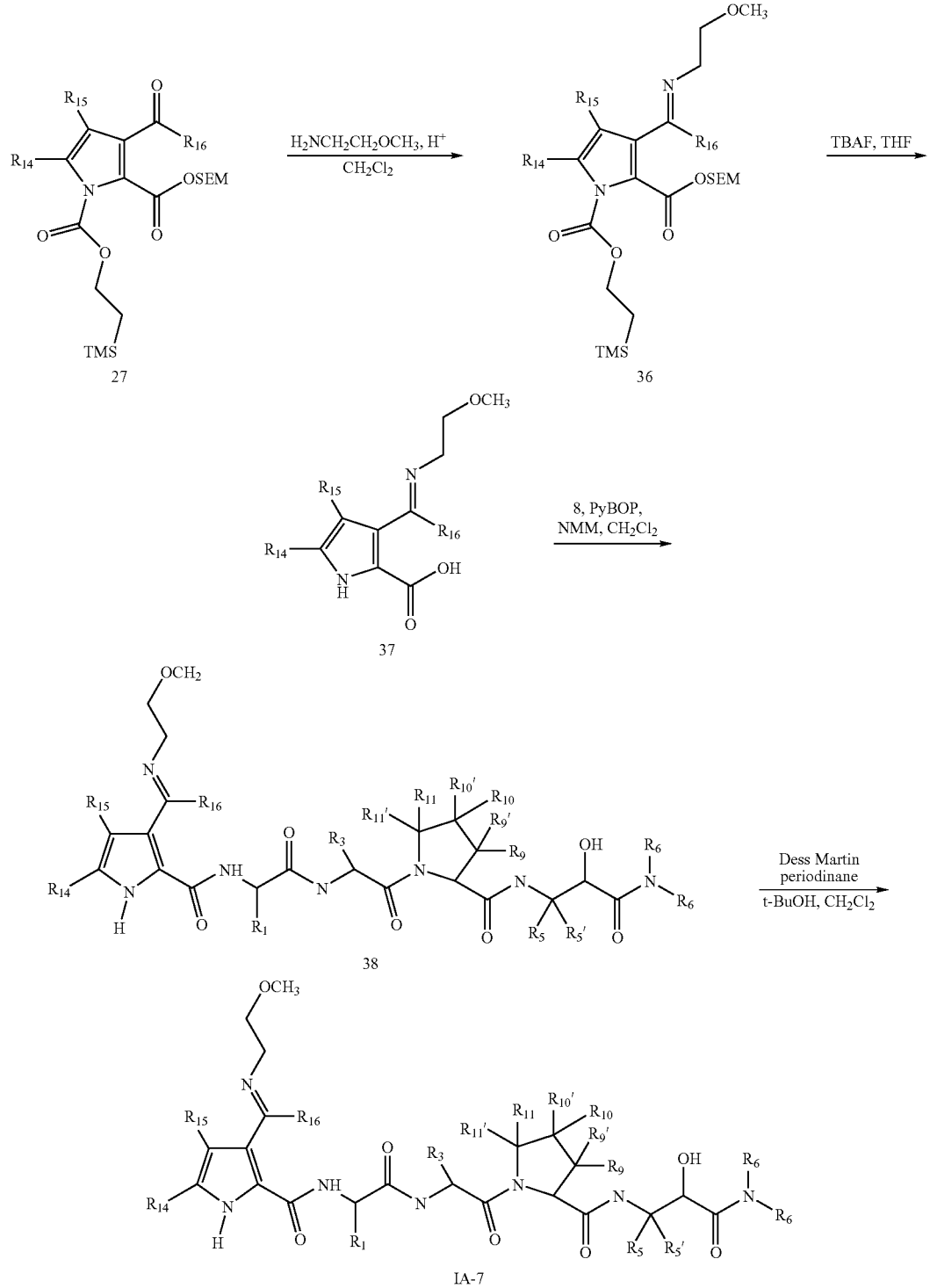

herein. Protected pyrrole ester 27 (prepared by methods described above in scheme 5 and scheme 6) is condensed with an appropriate amine, according to the procedure in *J. Chem. Soc. Chem. Commun.*, (6) pp. 634-635 (1986), to give imine 36. TBAF deprotection of both silyl based protecting groups according to the procedure described in *J. Chem. Soc. Perkin Trans.* (1), pp. 2181-2186 (1986), gives pyrrole imine acid 37.

Final coupling and oxidation are accomplished according to the procedures listed above in schemes 1, 3, and 5. As would be recognized by skilled practitioners, other suitable and commercially available coupling reagents may be used to prepare intermediate 38. Likewise the oxidation of intermediate 38 to IA-7 may be accomplished using other suitable conditions known to the skilled artisan.

Scheme 8:

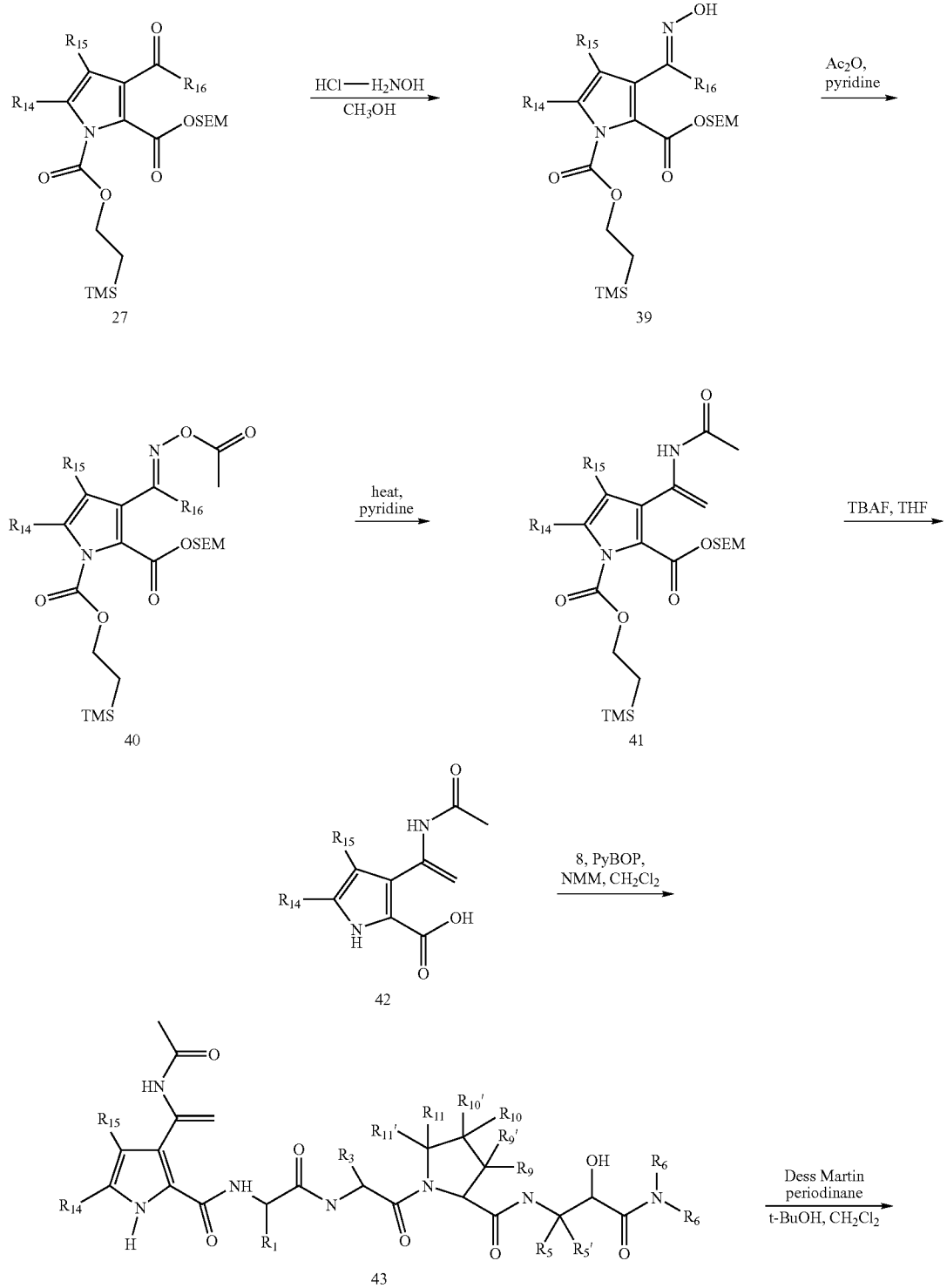

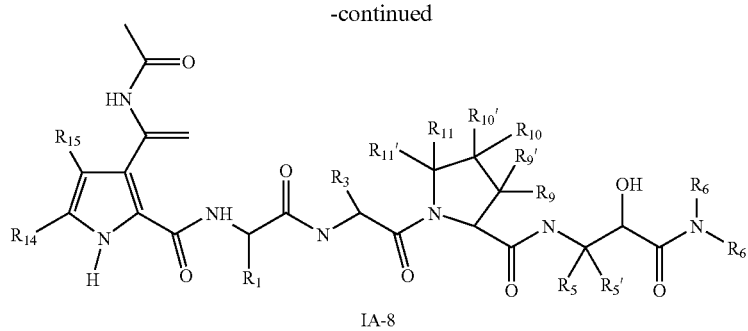

IA-8

Scheme 8 above provides a general route for the preparation of compounds of formula I and IA-8 wherein V is —C(O), W is —C(O)C(O)—N(R$_6$)$_2$, R$_{18}$ is absent and R$_{18'}$ is =CH$_2$, U is nitrogen, R$_{16}$ is R' wherein R' is acetyl, A is hydrogen, R$_2$, R$_4$, and R$_7$ are H, R$_1$, R$_3$, R$_5$, R$_{5'}$, R$_6$, R$_9$, R$_{9'}$, R$_{10}$, R$_{10'}$, R$_{11}$, R$_{11'}$, R$_{12}$, R$_{12'}$, R$_{14}$, and R$_{15}$, are as described in any of the embodiments herein. Condensation of 27 with hydroxylamine using the procedure described in *J. Org. Chem.*, pp. 5917-5921 (1992), gives oxime 39. Oxime acylation with acetic anhydride followed by thermal rearrangement in pyridine, according to the procedure described in *Leibigs Ann. Chem.*, (12), pp. 2065-2080 (1986), gives enamide 41. TBAF deprotection of both silyl based protecting groups according to the procedure described in *J. Chem. Soc. Perkin Trans.* (1), pp. 2181-2186 (1986), gives pyrrole acid 42. Final coupling and oxidation are accomplished according to the procedures listed above in schemes 1, 3, 5, and 7. As would be recognized by skilled practitioners, other suitable and commercially available coupling reagents may be used to prepare intermediate 43. Likewise the oxidation of intermediate 43 to IA-8 may be accomplished using other suitable conditions known to the skilled artisan.

Scheme 9:

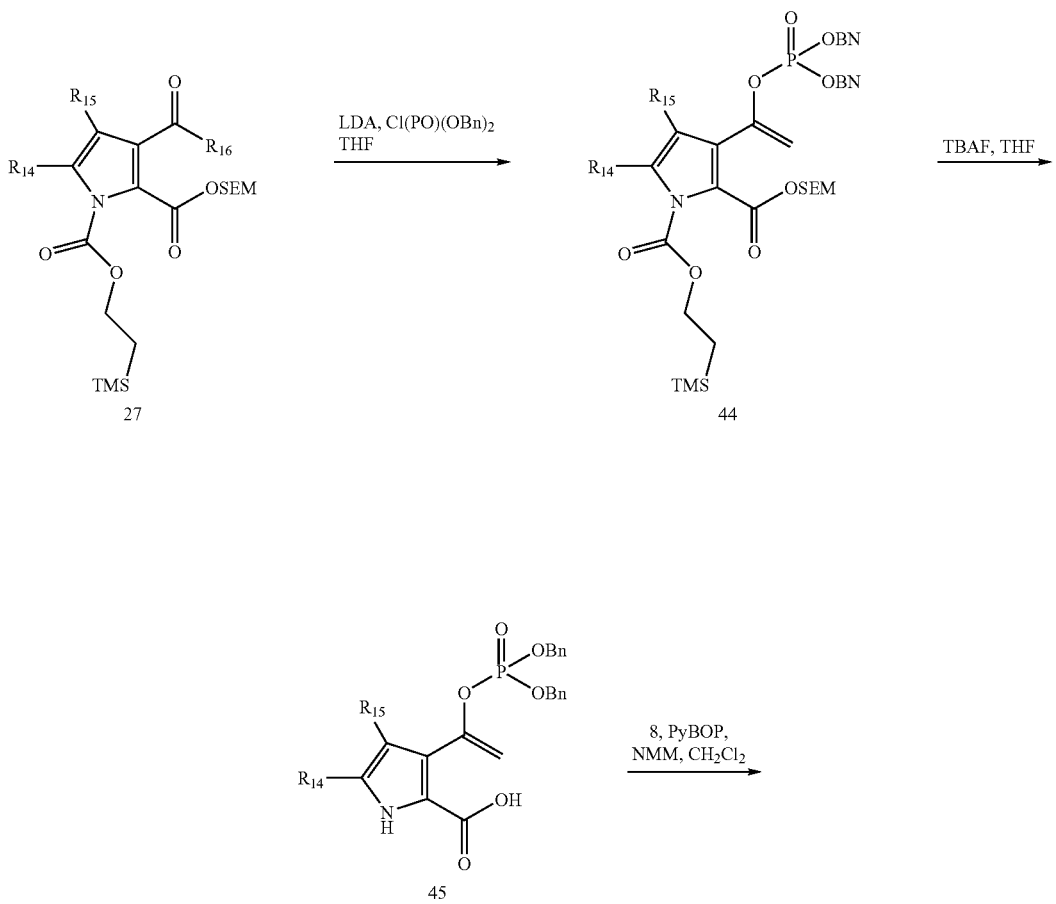

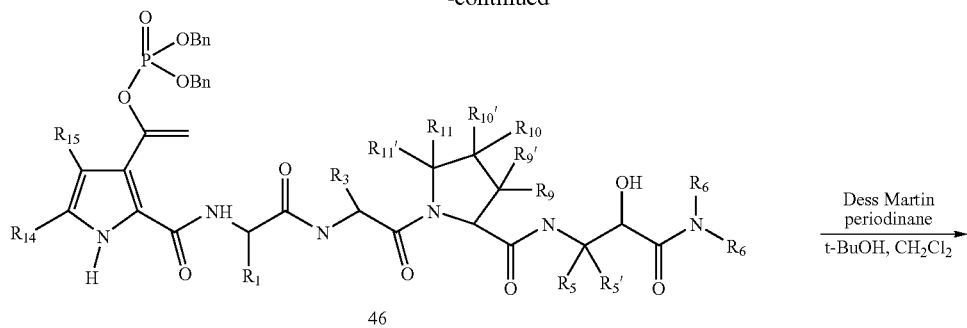

46

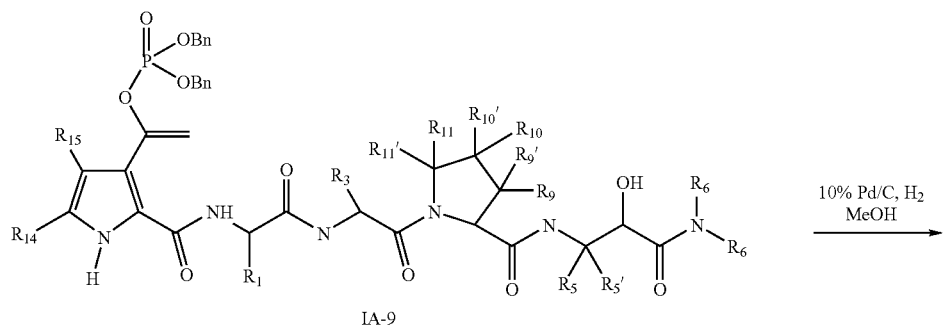

IA-9

IA-10

Scheme 9 above provides a general route for the preparation of compounds of formula I, IA-9, and IA-10 wherein V is —C(O), W is —C(O)C(O)—N($R_6$)$_2$, $R_{18}$ is absent and $R_{18'}$ is =$CH_2$, U is oxygen, $R_{16}$ is —P(O)(OR')$_2$ wherein R' is benzyl (IA-9) or hydrogen (IA-10), A is hydrogen, $R_2$, $R_4$, and $R_7$ are H, $R_1$, $R_3$, $R_5$, $R_{5'}$, $R_6$, $R_9$, $R_{9'}$, $R_{10}$, $R_{10'}$, $R_{11}$, $R_{11'}$, $R_{12}$, $R_{12'}$, $R_{14}$, and $R_{15}$, are as described in any of the embodiments herein. The enolate of protected pyrrole ester 27 (prepared as described in the preceding schemes wherein $R_{16}$ is methyl) is generated with LDA and reacted with dibenzylchlorophosphate according to the method described in *Tet. Lett.*, pp. 4275-4277 (2003) to give enol phosphate 44. It will be appreciated by those skilled in the art that other enol phosphates of interest may be prepared by the same procedure by adjusting the starting chlorophosphate reagent used. TBAF deprotection of both Silyl based protecting groups according to the procedure described in *J. Chem. Soc. Perkin Trans.* (1), pp. 2181-2186 (1986), gives pyrrole acid 45. Final coupling and oxidation are accomplished according to the procedures listed in any of the schemes above. As would be recognized by skilled practitioners, other suitable and commercially available coupling reagents may be used to prepare intermediate 46. Hydrogenolysis of dibenzyl ester IA-9 using standard palladium catalysis gives free enol phosphonooxy acid IA-10. Likewise the oxidation of intermediate 24 and the deprotection of IA-9 may be accomplished using other suitable conditions known to the skilled artisan.

Scheme 10:

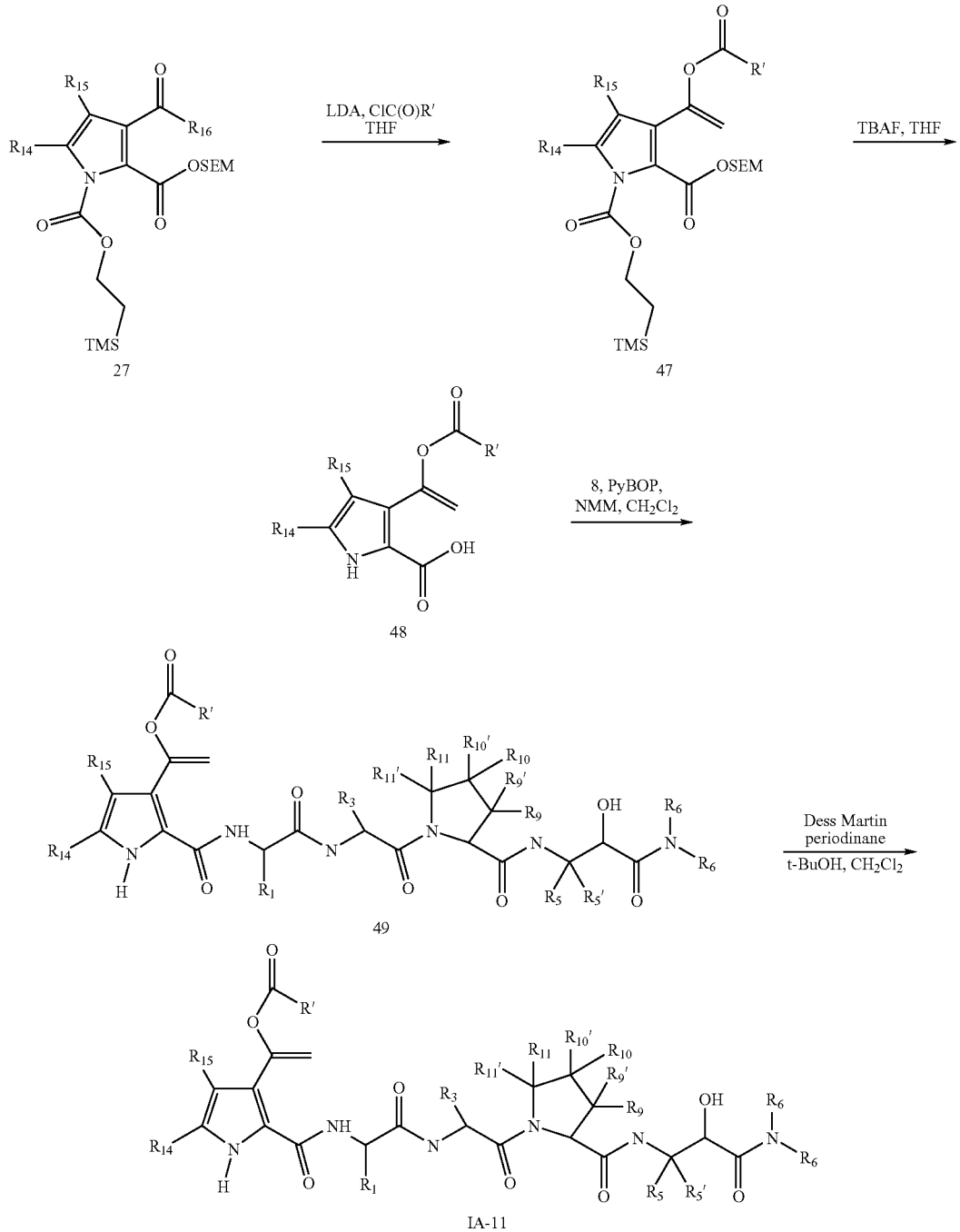

Scheme 10 above provides a general route for the preparation of compounds of formula I and IA-11 wherein V is —C(O), W is —C(O)C(O)—N($R_6$)$_2$, $R_{18}$ is absent and $R_{18'}$ is =$CH_2$, U is oxygen, $R_{16}$ is —C(O)R', A is hydrogen, $R_2$, $R_4$, and $R_7$ are H, $R_1$, $R_3$, $R_5$, $R_{5'}$, $R_6$, $R_9$, $R_{9'}$, $R_{10}$, $R_{10'}$, $R_{11}$, $R_{11'}$, $R_{12}$, $R_{12'}$, $R_{14}$, $R_{15}$, and $R_{16}$, are as described in any of the embodiments herein. The enolate of protected pyrrole ester 27 (prepared as described in the preceding schemes wherein $R_{16}$ is methyl) is generated with LDA and reacted with a suitable acyl chloride to give enol ester 47. TBAF deprotection of both silyl based protecting groups according to the procedure described in *J. Chem. Soc. Perkin Trans.* (1), pp. 2181-2186 (1986), gives pyrrole acid 48. Final coupling and oxidation are accomplished according to the procedures listed in any of the schemes above. As would be recognized by skilled practitioners, other suitable and commercially available coupling reagents may be used to prepare intermediate 48. Likewise the oxidation of intermediate 48 may be accomplished using other suitable conditions known to the skilled artisan. Enol ethers wherein $R_{18}$ is absent and $R_{18'}$ is =$CH_2$, U is oxygen and $R_{16}$ is —R' may also be prepared according to the methods listed in scheme 10. For instance to prepare the enol ether analog wherein $R_{16}$ is methyl, the pyrrole enolate generated from LDA treatment of 27 could be reacted with dimethyl sulfate and then carried through the same synthetic sequence described above.

$R_3$, $R_5$, $R_{5'}$, $R_6$, $R_9$, $R_{9'}$, $R_{10}$, $R_{10'}$, $R_{11}$, $R_{11'}$, $R_{12}$, $R_{12'}$, $R_{14}$, $R_{15}$, and $R_{16}$, are as described in any of the embodiments herein. The pyrrole nitrogen in intermediate 11 (prepared as described in the preceding schemes) is Boc protected under Scheme 11:

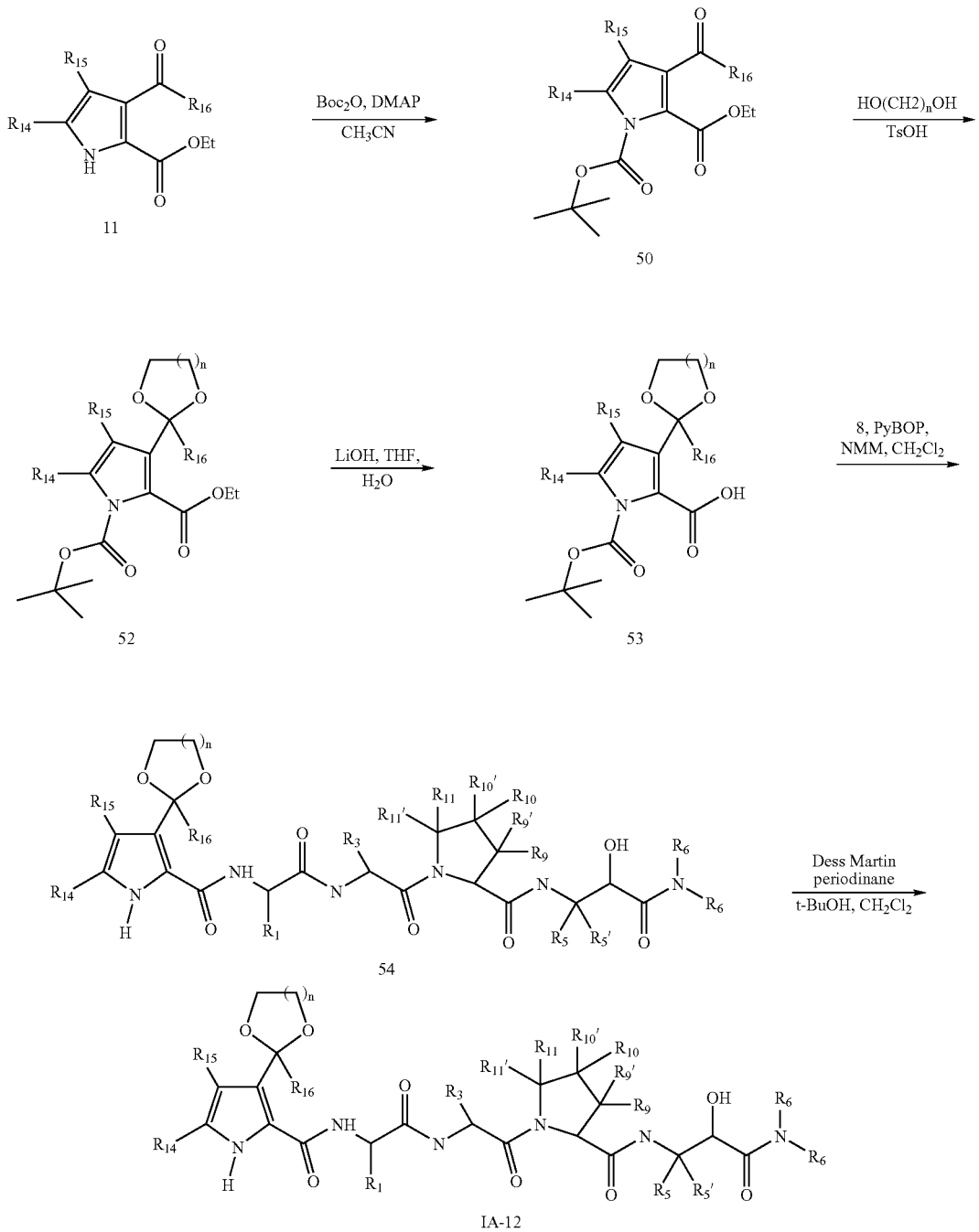

Scheme 11 above provides a general route for the preparation of compounds of formula I and IA-12 wherein V is —C(O), W is —C(O)C(O)—N($R_6$)$_2$, are optionally taken together with the carbon atom to which they are bound to form a 5- to 7-membered saturated ring system; wherein the $R_{18}$ and $R_{18'}$ atoms bound to the carbon atom are O; U is a bond, $R_{16}$ is —R', A is hydrogen, $R_2$, $R_4$, and $R_7$ are H, R', $R_1$, standard conditions to give BOC-protected pyrrole ester 50. Acid catalyzed condensation with an appropriate diol according to the method described in *J. Org. Chem.* pp. 2663-2669 (1984), gives ketal 52 which is hydrolized under basic conditions to give the pyrrole acid 53. Final coupling and oxidation are accomplished according to the procedures listed in any of the schemes above. As would be recognized by skilled practitioners, other suitable and commercially available coupling reagents may be used to prepare intermediate 54. Likewise the oxidation of intermediate 54 may be accomplished using other suitable conditions known to the skilled artisan.

Scheme 12:

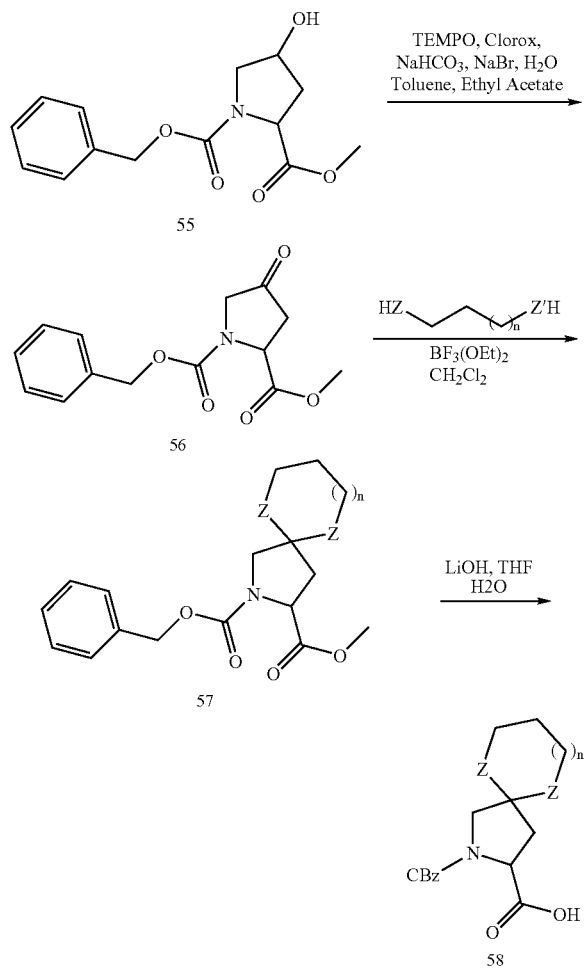

formula I and IH wherein V is —C(O), W is —C(O)C(O)—N($R_6$)$_2$, $R_2$, $R_4$, and $R_7$ are H, and $R_1$, $R_3$, $R_5$, $R_{5'}$, $R_6$, $R_9$, $R_{9'}$, $R_{11}$, $R_{11'}$, $R_{12}$, $R_{12'}$, $R_{14}$, $R_{15}$, $R_{16}$, $R_{18}$, $R_{18'}$, n, A, U, Z, and Z' are as described in any of the embodiments herein. Scheme 12 above in combination with scheme 1 also provides a general route for the preparation of compounds of formula I and IK using modifications (e.g. other appropriate commercially available starting materials) known to those skilled in the art.

Scheme 13:

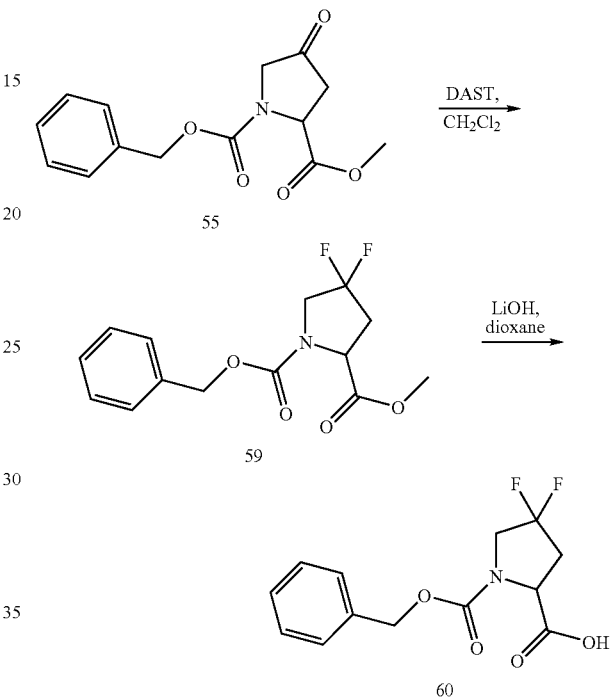

Scheme 12 above in combination with scheme 1 above provides a general route for the preparation of compounds of Scheme 13 above in combination with scheme 1 above provides a general route for the preparation of compounds of formula I and IK wherein V is —C(O), W is —C(O)C(O)—N($R_6$)$_2$, $R_2$, $R_4$, and $R_7$ are H, $R_{10}$, and $R_{10'}$ are fluoro, and $R_1$, $R_3$, $R_5$, $R_{5'}$, $R_6$, $R_9$, $R_{9'}$, $R_{11}$, $R_{11'}$, $R_{12}$, $R_{12'}$, $R_{14}$, $R_{15}$, $R_{16}$, $R_{18}$, $R_{18'}$, A, and U, are as described in any of the embodiments herein.

Scheme 14:

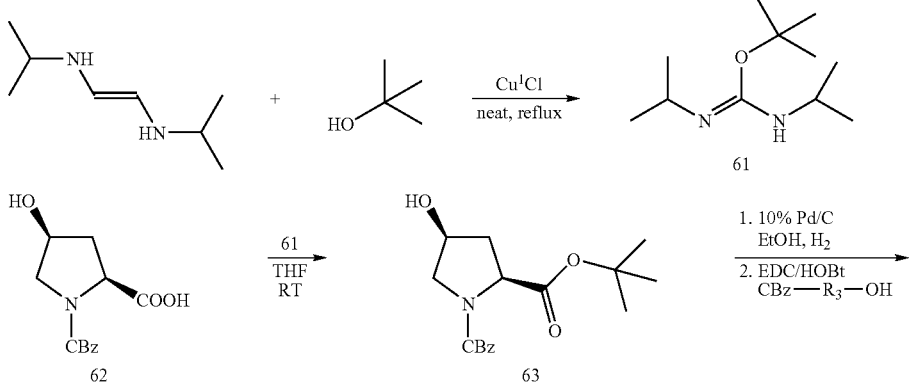

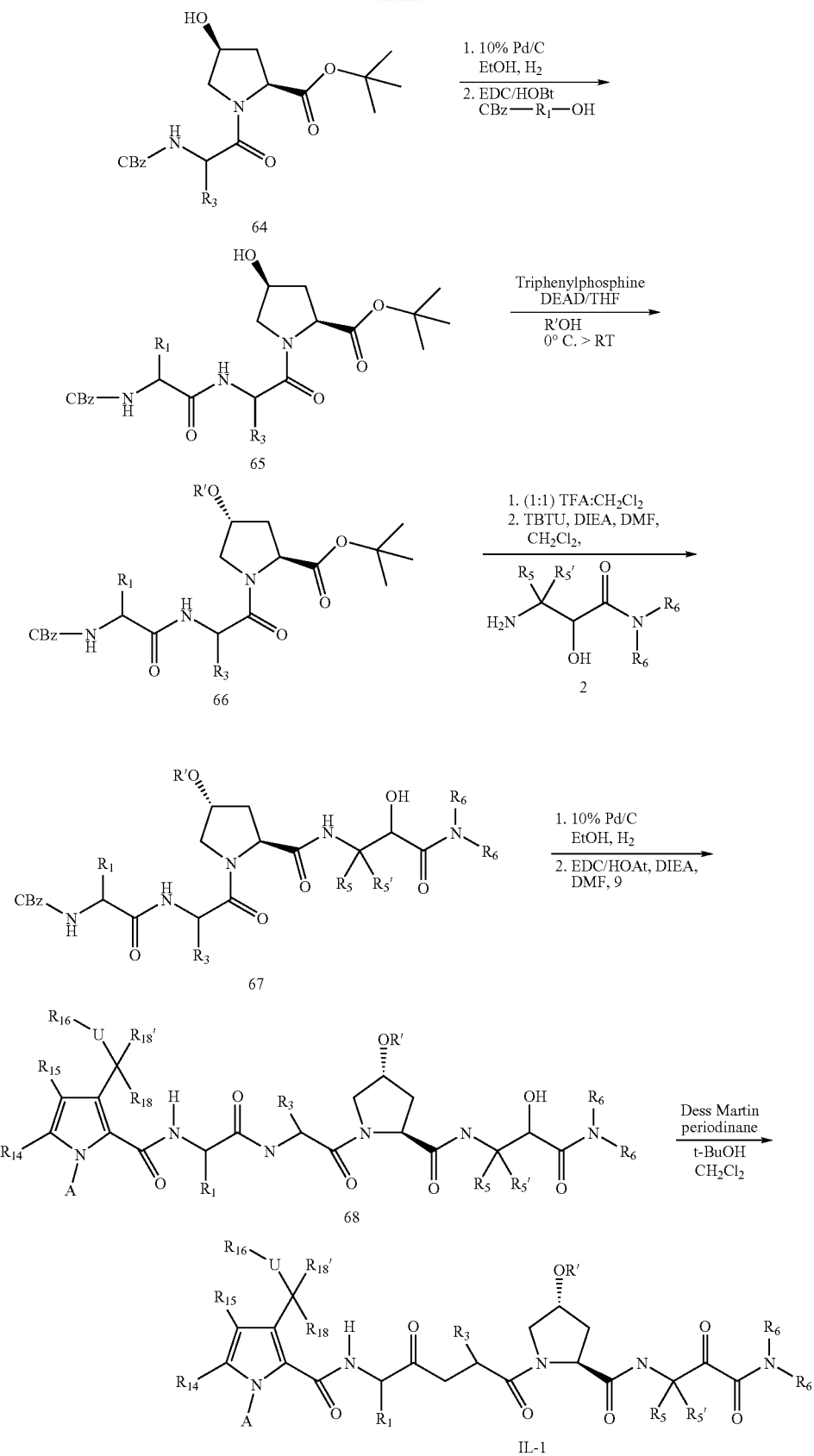

Scheme 14 above provides a general route for the preparation of compounds of formula I, IL, and IL-1 wherein V is —C(O), W is —C(O)C(O)—N(R$_6$)$_2$, R$_2$, R$_4$, R$_7$, R$_9$, R$_9'$, R$_{10'}$, R$_{11}$, and R$_{11'}$, are H, R$_{10'}$ is OR', and R$_1$, R$_3$, R$_5$, R$_{5'}$, R$_6$, R$_{14}$, R$_{15}$, R$_{16}$, R$_{18}$, R$_{18'}$, A, and U, are as described in any of the embodiments herein. As would be appreciated by any skilled practitioner, compound 67 may be carried on to compounds of formula IL-1 by routine methods. Additionally, other suitable and commercially available coupling reagents may be used to prepare intermediates 64, 65, 67, and 68. Likewise, the oxidation of intermediate 68 to compounds of formula IL-1 may be accomplished using other suitable conditions known to the skilled artisan.

Scheme 15:

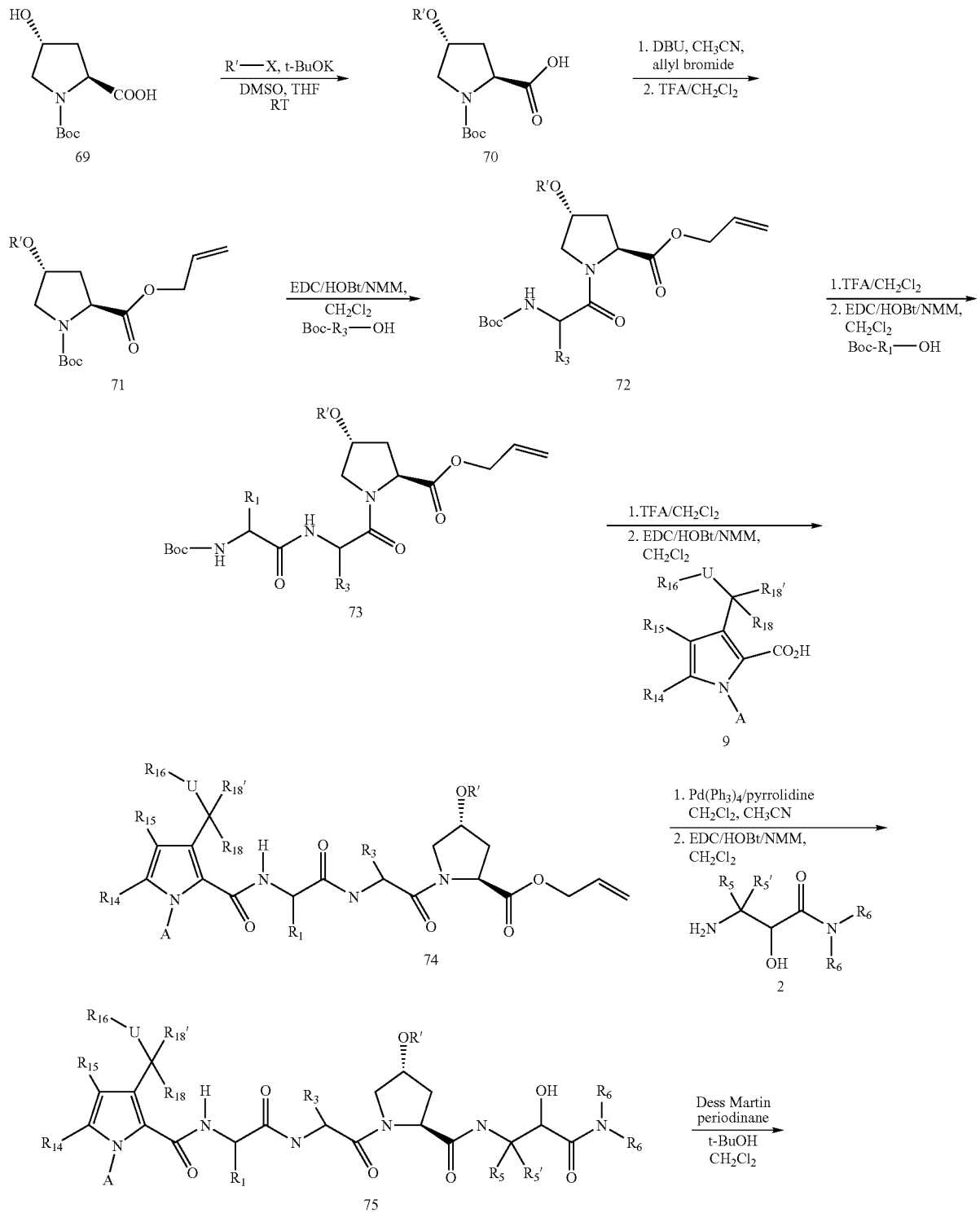

-continued

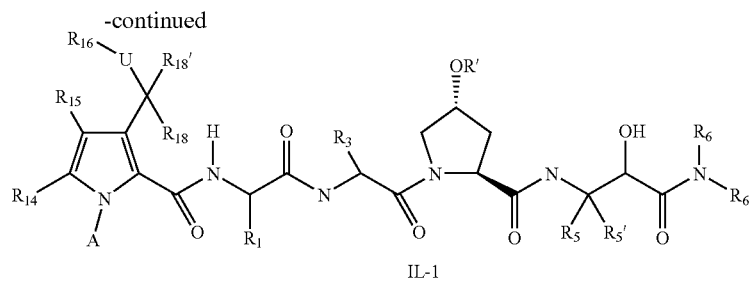

IL-1

Scheme 15 above, depicts an alternative approach to preparing compounds of formula IL and IL-1 of this invention wherein V is —C(O), W is —C(O)C(O)—N($R_6$)$_2$, $R_2$, $R_4$, $R_7$, $R_9$, $R_{9'}$, $R_{10}$, $R_{11'}$, and $R_{11}$, are H, $R_{10'}$ is OR', and $R_1$, $R_3$, $R_5$, $R_{5'}$, $R_6$, $R_{14}$, $R_{15}$, $R_{16}$, $R_{18}$, $R_{18'}$, A, and U, are as described in any of the embodiments herein. In this approach, a 4-hydroxyproline derivative 69 is reacted with a commercially available R'-halide (such an aryl chloride), represented by R'—X, in the presence of a suitable base (such as potassium t-butoxide) to provide a compound 70. As would be appreciated by any skilled practitioner, compound 70 may be carried on to compounds of formula IE-1 by routine methods. Additionally, other suitable and commercially available coupling reagents may be used to prepare intermediates 72, 73, 74, and 75. Likewise, the oxidation of intermediate 75 to compounds of formula IL-1 may be accomplished using other suitable conditions known to the skilled artisan.

Scheme 16 in combination with scheme 1 above provides a general route for the preparation of compounds of formula IM, and IM-1 wherein V is —C(O), W is —C(O)C(O)—N($R_6$)$_2$, $R_2$, $R_4$, $R_7$, $R_9$, $R_{9'}$, $R_{10'}$, and $R_{11'}$, are H, $R_{10}$ and $R_{11}$ are taken together with the ring atoms to which they are bound to form a ring system as defined in any of the embodiments and $R_1$, $R_3$, $R_5$, $R_{5'}$, $R_6$, $R_{14}$, $R_{15}$, $R_{16}$, $R_{18}$, $R_{18'}$, A, and U, are as described in any of the embodiments herein. Bicyclic starting materials such as compound 76 may be any commercially available reagents of interest or may be synthesized according to literature methods known to the skilled artisan. After coupling of 76 to intermediate 2, resulting intermediate 80 may be carried on to compounds of formula IM-1 by the methods described in scheme 1. Scheme 16 in combination with scheme 1

Compounds of this invention represented by formula IN may also be prepared from commercially available amino Scheme 16:

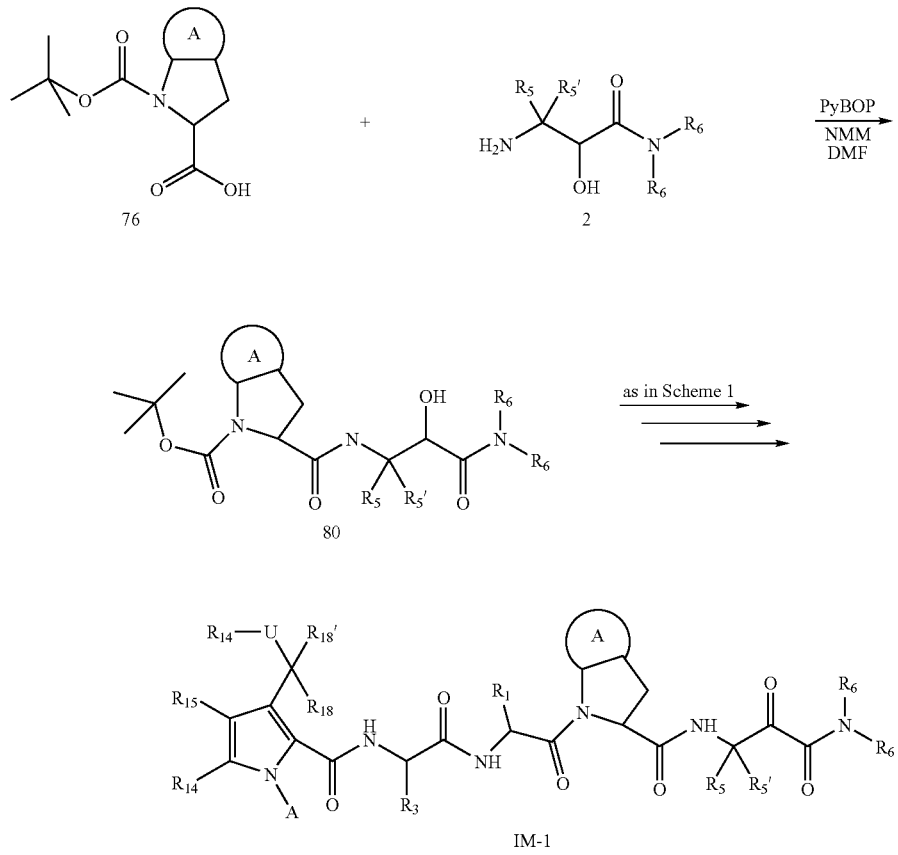

IM-1 acid derivatives by the route described in schemes 1 and 16 above. If a starting amino acid analogue of interest is not commercially available it may be prepared according to literature methods known to those skilled in the art.

Scheme 17:

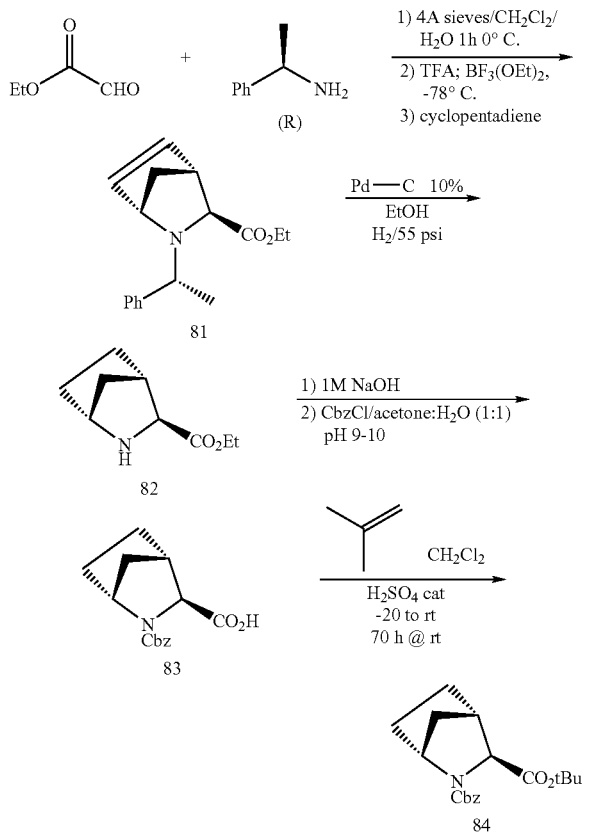

Scheme 17 above provides a synthetic route for the preparation of Cbz-protected azabicyclo[2.2.1]heptane-3-carboxylic acid, compound 83 and the corresponding t-butyl ester, compound 84. The free acid 83 may be further elaborated by the route defined in scheme 1 above to prepare compounds of formula I and IO.

The preparation of various other optionally substituted multicyclic azaheterocyclyls intermediates to prepare compounds of formulae I and IN via schemes 1, 14 or 15 above, may be accomplished by the methods described in PCT publication No. WO 02/18369 and references cited therein.

Various 3, 4, and 5-substituted proline analogues may either be purchased commercially or prepared according to known literature procedures. For instance, for compounds of formula I wherein $R_{9'}$ is (C1-C12)-aliphatic-, the starting 3-substituted proline analogues may be prepared according to the method of Holladay, M. W. et al., *J. Med. Chem.*, 34, pp. 457-461 (1991). For compounds of formula I wherein either $R_{9'}$, $R_{10'}$, or $R_{11'}$ are cyclohexyl and $R_9$, $R_{10}$, or $R_{11}$ are hydrogen, the cyclohexyl proline intermediates may be prepared by platinum oxide reduction of the commercially available phenyl substituted proline analogues. Such reduction conditions are well known to those skilled in the art. For compounds of formula I wherein $R_{9'}$ is (C1-C12)-aliphatic- and $R_{10'}$ is (C1-C12)-aliphatic-, the starting 3,4-disubstituted proline analogues may be prepared according to the method of Kanamasa, S. et al., *J. Org. Chem.*, 56, pp. 2875-2883 (1991). In each of the syntheses involving 3, 4, or 5-substituted prolines or 3,4-disubstituted prolines, the intermediates may be further elaborated by the routes defined above in schemes 1, 14, or 15 to prepare compounds of formula I.

Accordingly, one embodiment of this invention provides a process for preparing a compound of formula I, as defined in any of the embodiments herein, comprising the step of: reacting a compound of formula VII in the presence of a compound of formula VIII to provide a compound of formula IX:

wherein:

$R_{21}$ is an amine protecting group, a P3-residue of an HCV protease inhibitor described herein, or a P4-P3-residue of an HCV protease inhibitor as described herein, and wherein the P3 and the P4-P3 residues are optionally protected with an amino-terminal capping group;

$R_{20}$ is a carboxy protecting group or a P1 residue of an HCV protease inhibitor described herein, wherein the P1 residue is optionally protected with a carboxy terminal protecting group or with W. R' is as defined in any of the embodiments herein. X is an appropriate leaving group. As would be appreciated by skilled practitioners, an appropriate leaving group may be generated in situ.

In an alternative embodiment, the 4-hydroxy group in formula VII may be converted to a leaving group. In such an embodiment, X is a nucleophilic oxygen which reacts with VII to provide IX.

As used herein, P1, P3, P4 refer to the residues of an HCV protease inhibitor as defined in the art and as are well known to skilled practitioners.

The compound of formula IX may be carried on to a compound of formula I according to the methods described herein.

Although certain exemplary embodiments are depicted and described below, it will be appreciated that compounds of this invention can be prepared according to the methods described generally above using appropriate starting materials generally available to one of ordinary skill in the art.

Another embodiment of this invention provides a pharmaceutical composition comprising a compound of formula I or a pharmaceutically acceptable salt thereof. According to a preferred embodiment, the compound of formula I is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In one embodiment, the compositions of this invention additionally comprise another agent, preferably a cytochrome P-450 inhibitor. Such cytochrome P-450 inhibitors include, but are not limited to, ritonavir.

In another embodiment, the compositions of this invention additionally comprise another anti-viral agent, preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10-90% $CH_3CN/H_2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

3-Acetyl-4,5-dimethyl-2-pyrrole carboxylic acid (35)

A solution of sodium nitrite (36.9 g, 0.534 mol) in 70 mL of water was added dropwise to a stirred solution of ethylacetoacetate (70 g, 0.538 mol) in 1401 mL of glacial acetic acid at 0° C. After the addition was complete, the light yellow reaction mixture was allowed to warm to room temperature. After 30 minutes, all the starting material had been consumed, the reaction was quenched with 350 mL of water and extracted with ethyl acetate (2×125 mL). The organic extracts were combined and washed with water (2×125 mL) and saturated sodium hydrogen carbonate aqueous solution (2×105 mL). The organic layer was dried with sodium sulfate and concentrated in vacuo to give 84.2 g (98%) of ethyl-2-hydroxyimino-3-oxobutanoate 31 as a pale yellow oil. $^1$H NMR (CDCl$_3$) δ 10.3 (s, 1H), 4.2 (q, 2H), 2.3 (s, 3H), 1.3 (t, 3H) ppm.

Crushed sodium (12.4 g, 0.540 mol) was added to a solution of 2-butanone (48.2 mL, 0.538 mol) and ethyl formate (43.47 mL, 0.538 mol) in dry ether (540 mL) with vigorous mechanical stirring over a period of 1 h, during which time the mixture was chilled in an ice-salt bath. The mixture was then stirred at room temp. for 14 h. After cooling the reaction mixture to 4° C. for a few hours, the precipitated sodium salt was obtained by filtration and washed thoroughly with cold, dry ether to afford 49.3 g (75%) of the desired sodium salt of 2-Methyl-3-oxobutyraldehyde 32. $^1$H NMR (DMSO-d$_6$) δ 9.1 (s, 1H), 1.9 (s, 3H), 1.3 (s, 3H) ppm.

Sodium salt 32 (49.3 g, 0.404 mol) and oxime 31 (64.23, 0.404 mol) were stirred in 300 mL of 70% acetic acid/30% water and warmed to 50° C. Zinc powder (42.21 g, 0.646 mol) was added portion-wise over 30 minutes maintaining the temperature below 100° C. When the addition was complete, the suspension was refluxed for 15 minutes, then poured into 4 L of ice-water. After a short time, the product precipitated out to give, after filtration, 30.1 g (45%) of the desired ethyl-4,5-dimethyl-2-pyrrole carboxylate 33. $^1$H NMR (CDCl$_3$) δ 9.0 (bs, 1H), 6.7 (s, 1H), 4.3 (q, 2H), 2.3 (s, 3H), 2.0 (s, 3H), 1.3 (t, 3H) ppm.

To a solution of aluminum chloride (50.19 g, 0.376 mol) in dry dichloroethane (580 mL) at 25° C. was added slowly acetic anhydride (17.75 mL, 0.188 mol). The resulting mixture was stirred at room temp. for 10 minutes, then a solution of pyrrole 33 (10.49 g, 0.0627 mol) in dichloroethane (30 mL) was added and the reaction mixture was stirred at room temp. for 2 h. After an additional 3 h at 80° C., the mixture was poured into ice water and extracted with dichloromethane. The organic layer was dried with anhy. sodium sulfate and concentrated in vacuo to an orange residue. Short plug filtration over silica gel (30% ethyl acetate/70% hexanes) gave 7.5 g (60%) of ethyl-3-acetyl-4,5-dimethyl-2-pyrrole carboxylate 34. $^1$H NMR (CDCl$_3$) δ 9.0 (bs, 1H), 4.3 (q, 2H), 2.7 (s, 3H), 2.1 (s, 3H), 1.9 (s, 3H), 1.3 (t, 3H) ppm.

A mixture of pyrrole ester 34 (8.2 g, 0.0392 mol), in ethanol and 100 mL of 10% potassium hydroxide were refluxed for 1 h. The mixture was cooled and concentrated in vacuo to an oil. Water was added to the oil, the mixture acidified with dilute HCl and extracted with ether. The organic phase was dried with anhy. sodium sulfate and concentrated in vacuo to a solid residue. The compound was recrystallized in 80 mL of ethanol to give 5.8 g of pure 3-acetyl-4,5-dimethyl-2-pyrrole carboxylic acid 35 as a solid. $^1$H NMR (DMSO-d$_6$) δ 2.5 (s, 3H), 2.2 (s, 3H), 2.0 (s, 3H) ppm.

We claim:
1. A pharmaceutical composition comprising a compound of formula I:

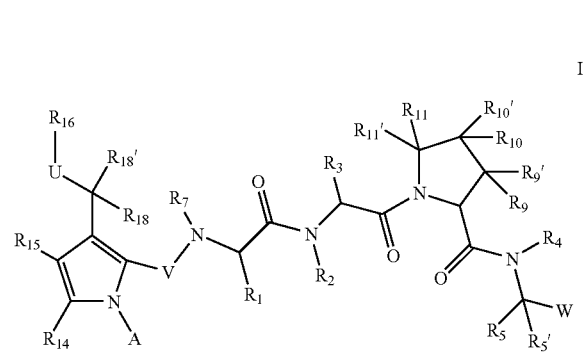

or a pharmaceutically acceptable salt thereof,
wherein:
$R_9$ and $R_{9'}$ are each independently:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-, (C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein up to three aliphatic carbon atoms in each of $R_9$ and $R_{9'}$ are optionally replaced by O, N, NH, S, SO, or $SO_2$ in a chemically stable arrangement;
wherein each of $R_9$ and $R_{9'}$ is independently and optionally substituted with up to 3 substituents independently selected from J;
J is halogen, —OR', —NO₂, —CN, —CF₃—OCF₃, —R', oxo, thioxo, =N(R'), =N(OR'), 1,2-methylenedioxy, 1,2-ethylenedioxy, —N(R')₂, —SR', —SOR', —SO₂R', —SO₂N(R')₂, —SO₃R', —C(O)R', —C(O)C(O)R', —C(O)C(O)OR', —C(O)C(O)N(R')₂, —C(O)CH₂C(O)R', —C(S)R', —C(S)OR', —C(O)OR', —OC(O)R', —C(O)N(R')₂, —OC(O)N(R')₂, —C(S)N(R')₂, —(CH₂)₀₋₂NHC(O)R', —N(R')N(R')COR', —N(R')N(R')C(O)OR', —N(R')N(R')CON(R')₂, —N(R')SO₂R', —N(R')SO₂N(R')₂, —N(R')C(O)OR', —N(R')C(O)R', —N(R')C(S)R', —N(R')C(O)N(R')₂, —N(R')C(S)N(R')₂, —N(COR')COR', —N(OR')R', —C(=NH)N(R')₂, —C(O)N(OR')R', —C(=NOR')R', —OP(O)(OR')₂, —P(O)(R')₂, —P(O)(OR')₂, or —P(O)(H)(OR');
wherein;
each R' is independently selected from the group consisting of:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom optionally form a 5- to 6-membered aromatic or a 3- to 7-membered saturated or partially unsaturated ring system having up to 3 heteroatoms independently selected from the group consisting of N, NH, O, S, SO, and SO₂, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;
$R_{10}$, $R_{10'}$, $R_{11}$, and $R_{11'}$ are each independently:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein any ring is optionally fused to a (C6-C10)aryl, (C5-C10)heteroaryl, (C3-C10)cycloalkyl, or (C3-C10)heterocyclyl;
wherein up to 3 aliphatic carbon atoms in each of $R_{10}$, $R_{10'}$, $R_{11}$, and $R_{11'}$ are optionally replaced by a heteroatom selected from O, NH, S, SO, or $SO_2$ in a chemically stable arrangement;
wherein each of $R_{10}$, $R_{10'}$, $R_{11}$, and $R_{11'}$ is independently and optionally substituted with up to 3 substituents independently selected from J; or
$R_{10}$ is —OR' and $R_{10'}$ is H, or
$R_{10}$ and $R_{10'}$ are both —OR' or —SR'; or
$R_{10}$ and $R_{10'}$ are both fluorine; or
$R_{10}$ and $R_{10'}$ are optionally taken together with the carbon atom to which they are bound to form a 5- to 7-membered saturated or partially unsaturated ring system;
wherein the $R_{10}$ and $R_{10'}$ atoms bound to the carbon atom are independently C(H), N, NH, O, S, SO, or $SO_2$;
wherein said ring optionally contains up to 4 heteroatoms independently selected from the group consisting of N, NH, O, S, SO, and $SO_2$;
wherein any atom is optionally singly or multiply substituted with up to 2 substituents selected independently from J; and
wherein said ring is optionally fused to a second ring selected from the group consisting of (C6-C10)aryl, (C5-C10)heteroaryl, (C3-C10)cycloalkyl, and a (C3-C10)heterocyclyl, wherein said second ring has up to 3 substituents selected independently from J; or
$R_9$ and $R_{10}$ are optionally taken together with the ring atoms to which they are bound to form a 5- to 6-membered aromatic or a 3- to 7-membered saturated or partially unsaturated ring system up to 3 heteroatoms independently selected from N, NH, O, S, SO, or $SO_2$; wherein said ring system is optionally substituted with up to 3 substituents selected independently from J; or
$R_{10}$ and $R_{11}$ are optionally taken together with the ring atoms to which they are bound to form a 5- to 6-membered aromatic or a 3- to 7-membered saturated or partially unsaturated ring system having up to 3 heteroatoms independently selected from N, NH, O, S, SO, or $SO_2$; wherein said ring is optionally substituted with up to 3 substituents selected independently from J; or
$R_9$ and $R_{11}$ are optionally taken together with the ring atoms to which they are bound to form a bridged bicyclic saturated or partially unsaturated carbocyclic or heterocyclic ring system containing up to 10 atoms; wherein said ring system is optionally substituted with up to 3 substituents selected independently from J; wherein each heteroatom in the heterocyclic ring system is selected from the group consisting of N, NH, O, S, SO, and $SO_2$;
$R_1$ and $R_3$ are each independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in each of $R_1$ and $R_3$ are optionally replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;
$R_2$, $R_4$ and $R_7$ are each independently:
hydrogen-,
(C1-C12)-aliphatic-,
(C3-C10)-cycloalkyl-(C1-C12)-aliphatic-, or (C6-C10)-aryl-(C1-C12)-aliphatic-;
wherein up to two aliphatic carbon atoms in each of $R_2$, $R_4$ and $R_7$ are optionally replaced by a heteroatom selected from the group consisting of O, N, NH, S, SO, and $SO_2$ in a chemically stable arrangement;
wherein each of $R_2$, $R_4$ and $R_7$ is optionally substituted with up to 3 substituents independently selected from J;
$R_5$ and $R_{5'}$ are each independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or
$R_5$ and $R_{5'}$ together with the atom to which they are bound optionally form a 3- to 6-membered saturated or partially unsaturated ring having up to 2 heteroatoms selected from the group consisting of N, NH, O, SO, and $SO_2$; wherein said ring is optionally substituted with up to 2 substituents selected independently from J;
W is:

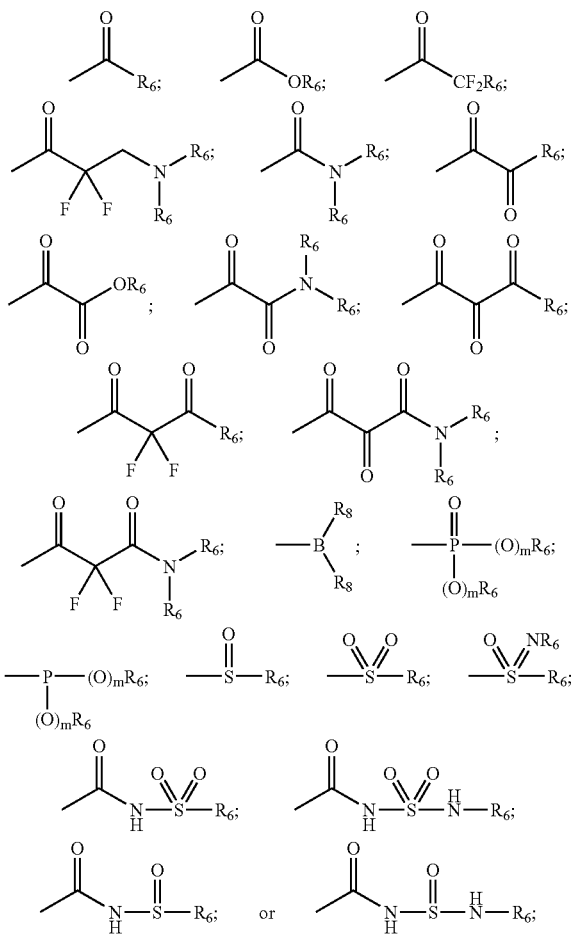

wherein m is 0 or 1;
wherein each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,

[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
wherein up to 3 aliphatic carbon atoms in each $R_6$ is optionally replaced by a heteroatom selected from O, NH, S, SO, or $SO_2$, in a chemically stable arrangement;
wherein $R_6$ is optionally substituted with up to 3 J substituents; or
two $R_6$ groups, together with the nitrogen atom to which they are bound, optionally form a 5- to 6-membered aromatic or a 3- to 7-membered saturated or partially unsaturated ring system having up to 3 heteroatoms independently selected from the group consisting of N, NH, O, S, SO, and $SO_2$, wherein said ring is optionally fused to a (C6-C10)aryl, (C5-C10)heteroaryl, (C3-C10) cycloalkyl, or a (C3-C10)heterocyclyl, wherein any ring has up to 3 substituents selected independently from J;
wherein each $R_8$ is independently —OR'; or the $R_8$ groups together with the boron atom, is a (C3-C10)-membered heterocyclic ring having in addition to the boron up to 3 additional heteroatoms selected from the group consisting of N, NR', O, SO, and $SO_2$;
V is —C(O)—, —C(S)—, —S(O)—, or —S(O)$_2$—;
A is hydrogen or —C($R_{12}$)($R_{12'}$)-T-$R_{13}$;
T is oxygen or a bond;
$R_{12}$ and $R_{12'}$ are each independently:
hydrogen-, or
(C1-C6)-aliphatic-;
wherein up to two aliphatic carbon atoms in each of $R_{12}$ and $R_{12'}$ are optionally replaced by a heteroatom selected from the group consisting of O, N, NH, S, SO, and $SO_2$ in a chemically stable arrangement; or
$R_{12}$ is absent and $R_{12'}$ is =O;
$R_{13}$ is —C(O)R', —P(O)(OR')$_2$, —SO$_3$R', —R', or $R_{19}$;
$R_{19}$ is:
hydrogen,
(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in each $R_{19}$ is optionally replaced by a heteroatom selected from O, NR$_{19}$, S, SO, or $SO_2$ in a chemically stable arrangement;
wherein up to 3 aliphatic carbon atoms in each $R_{19}$ is optionally replaced with —C(O)—;
wherein $R_{19}$ is optionally substituted with up to 3 J substituents;
wherein any NR$_{19}$, taken together with the nitrogen and a carbon adjacent to the nitrogen, optionally forms a 5- to 7-membered ring system, wherein said ring system optionally contains up to three additional heteroatoms selected from the group consisting of O, N, NH, S, SO, and $SO_2$ in a chemically stable arrangement;
$R_{14}$ and $R_{15}$ are independently halogen, —OR', —OC(O)N(R')$_2$, —NO$_2$, —CN, —CF$_3$, —OCF$_3$, —R', 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O) OR', —OC(O)R', —C(O)N(R')$_2$, —OC(O)N(R')$_2$, —C(S)N(R')$_2$, or —(CH$_2$)$_{0-2}$NHC(O)R';
$R_{16}$ is R', —C(O)R', —P(O)(OR')$_2$ or —SO$_3$R';
U is O, N, or a bond; and
$R_{18}$ and $R_{18'}$ are optionally taken together with the carbon atom to which they are bound to form a 5- to 7-membered saturated or partially unsaturated ring system;

wherein the $R_{18}$ and $R_{18'}$ atoms bound to the carbon atom are independently O or N;

wherein said ring optionally contains up to 1 additional heteroatom selected from the group consisting of N, NH, O, S, SO, and $SO_2$;

wherein any substitutable atom is optionally singly or multiply substituted with up to 2 substituents selected independently from J;

wherein said ring is optionally fused to a second ring selected from the group consisting of (C6-C10)aryl, (C5-C10)heteroaryl, (C3-C10)cycloalkyl, and a (C3-C10)heterocyclyl, wherein said second ring has up to 3 substituents selected independently from J;

provided that when $R_{18}$ and $R_{18'}$ are optionally taken together with the carbon atom to which they are bound to form a 5- to 7-membered saturated or partially unsaturated ring system, then $R_{16}$ is R'; or $R_{18'}$ is =O, $=CH_2$, =N(R'), or =N(OR') and $R_{18}$ is absent, provided that when $R_{18}$ is absent and $R_{18'}$ is $=CH_2$, then U is oxygen; and provided that when $R_{18}$ is absent and $R_{18'}$ is =O, =N(R') or =N(OR'), then U is a bond and $R_{16}$ is R'; and provided that when $R_{18}$ is absent, $R_{18'}$ is =O, U is a bond and $R_{16}$ is R', then A is $—C(R_{12})(R_{12})$-T-$R_{13}$;

and a acceptable carrier, adjuvant or vehicle, wherein said composition is formulated for administration to a patient.

2. The composition according to claim 1, wherein said composition comprises an additional agent selected from an immunomodulatory agent; an antiviral agent; a second inhibitor of HCV protease; an inhibitor of another target in the HCV life cycle; and a cytochrome P-450 inhibitor; or combinations thereof.

3. The composition according to claim 1, wherein said immunomodulatory agent is α-, β-, or γ-interferon or thymosin; said antiviral agent is ribavirin, amantadine, or telbivudine; or said inhibitor of another target in the HCV life cycle is an inhibitor of HCV helicase, polymerase, or metalloprotease.

4. The composition according to claim 2, wherein said cytochrome P-450 inhibitor is ritonavir.

* * * * *